United States Patent
Jendrisak et al.

(10) Patent No.: US 9,005,930 B2
(45) Date of Patent: Apr. 14, 2015

(54) KITS AND METHODS FOR GENERATING 5' CAPPED RNA

(71) Applicant: Cellscript, LLC, Madison, WI (US)

(72) Inventors: Jerome Jendrisak, Middleton, WI (US); Ronald Meis, Fitchburg, WI (US); Gary Dahl, Madison, WI (US)

(73) Assignee: Cellscript, LLC, Madison, WI (US)

( * ) Notice: Subject to any disclaimer, the term of this patent is extended or adjusted under 35 U.S.C. 154(b) by 0 days.

(21) Appl. No.: 14/471,649

(22) Filed: Aug. 28, 2014

(65) Prior Publication Data

US 2014/0363876 A1 Dec. 11, 2014

Related U.S. Application Data

(63) Continuation of application No. 14/185,384, filed on Feb. 20, 2014, now Pat. No. 8,846,348, which is a continuation of application No. 11/787,352, filed on Apr. 16, 2007, now abandoned.

(60) Provisional application No. 60/792,220, filed on Apr. 14, 2006.

(51) Int. Cl.
*C12P 19/34* (2006.01)
*C12P 21/06* (2006.01)

(52) U.S. Cl.
CPC ........................................ *C12P 19/34* (2013.01)

(58) Field of Classification Search
None
See application file for complete search history.

(56) References Cited

U.S. PATENT DOCUMENTS

| | | | |
|---|---|---|---|
| 5,021,335 A | 6/1991 | Tecott | |
| 5,168,038 A | 12/1992 | Tecott | |
| 5,514,545 A | 5/1996 | Eberwine | |
| 5,545,522 A | 8/1996 | Van Gelder | |
| 5,712,127 A | 1/1998 | Malek | |
| 5,716,785 A | 2/1998 | Van Gelder | |
| 5,831,068 A | 11/1998 | Nair | |
| 5,853,719 A | 12/1998 | Nair | |
| 5,891,636 A | 4/1999 | Van Gelder | |
| 5,958,688 A | 9/1999 | Eberwine | |
| 6,291,170 B1 | 9/2001 | Van Gelder | |
| 6,306,388 B1 | 10/2001 | Nair | |
| 6,387,701 B1 | 5/2002 | Nair | |
| 6,511,832 B1 | 1/2003 | Guarino et al. | |
| 6,670,186 B1 | 12/2003 | Nair | |
| 7,074,596 B2 | 7/2006 | Darzynkiewicz et al. | |
| 7,601,343 B2 | 10/2009 | Nair | |
| 2002/0018769 A1 | 2/2002 | Nair | |
| 2003/0186237 A1 | 10/2003 | Ginsberg | |
| 2004/0171041 A1 | 9/2004 | Dahl | |
| 2004/0197802 A1 | 10/2004 | Dahl | |
| 2005/0153333 A1 | 7/2005 | Sooknanan | |
| 2007/0281336 A1 | 12/2007 | Jendrisak | |
| 2014/0221248 A1 | 8/2014 | Jendrisak et al. | |

FOREIGN PATENT DOCUMENTS

| | | |
|---|---|---|
| EP | 2010659 | 1/2009 |
| WO | 00/75356 | 12/2000 |
| WO | 02/065093 | 8/2002 |
| WO | 2006/004648 | 1/2006 |
| WO | 2007/120863 | 10/2007 |

OTHER PUBLICATIONS

Shatkin "Capping of eucaryotic mRNAs" 1976 Cell 9:645-653.
Shatkin "mRNA cap binding proteins: essential factors for initiating translation" 1985 Cell 40: 223-4.
Shuman "Capping enzyme in eukaryotic mRNA synthesis" 1995 Prog. Nucleic Acid Res. Mol. Biol. 50: 101-129.
Shuman "Catalytic activity of vaccinia mRNA capping enzyme subunits coexpressed in *Escherichia coli*" 1990 J Biol Chem 265: 11960-11966.
Shuman "Structure, mechanism, and evolution of the mRNA capping apparatus" 2001 Prog. Nucleic Acid Res. Mol. Biol. 66: 1-40.
Shuman et al. "Purification and characterization of a GTP-pyrophosphate exchange activity from vaccinia virions. Association of the GTP-pyrophosphate exchange activity with vaccinia mRNA guanylyltransferase. RNA (guanine-7-)methyltransferase complex (capping enzyme)" 1980 J. Biol. Chem. 255: 11588.
Shuman, et al. "Domain structure of vaccinia virus mRNA capping enzyme. Activity of the Mr 95,000 subunit expressed in *Escherichia coli*" 1990 265: 11967-11972.
Sonenberg "Cap-binding proteins of eukaryotic messenger RNA: functions in initiation and control of translation" 1988 Prog. Nuc. Acid Res. 35: 173-207.
Stepinski, et al. "Synthesis and Properties of P1, P2-, P1, P3- and P1, P4-Dinucleoside Di-, Tri- and Tetraphosphate mRNA 5'-Cap Analogues" 1995 Nucleosides and Nucleotides 14: 717-721.

(Continued)

*Primary Examiner* — Suzanne M Noakes
*Assistant Examiner* — Jae W Lee
(74) *Attorney, Agent, or Firm* — Casimir Jones S.C.

(57) ABSTRACT

The present invention relates to kits and methods for efficiently generating 5' capped RNA having a modified cap nucleotide and for use of such modified-nucleotide-capped RNA molecules. In particular, the present invention provides kits and methods for capping RNA using a modified cap nucleotide and a capping enzyme system, such as poxvirus capping enzyme. The present invention finds use for in vitro production of 5'-capped RNA having a modified cap nucleotide and for in vitro or in vivo production of polypeptides by in vitro or in vivo translation of such modified-nucleotide-capped RNA. The invention also provides methods and kits for capturing or isolating uncapped RNA comprising primary RNA transcripts or RNA having a 5'-diphosphate, and methods and kits for using a capping enzyme system and modified cap nucleotides for labeling uncapped RNA comprising primary RNA transcripts or RNA having a 5'-diphosphate with detectable dye or enzyme moieties.

21 Claims, No Drawings

(56) References Cited

OTHER PUBLICATIONS

Su, et al. "Immunological and clinical responses in metastatic renal cancer patients vaccinated with tumor RNA-transfected dendritic cells" 2003 Cancer Res. 63: 2127-2133.
Van Gelder, et al. "Amplified RNA synthesized from limited quantities of heterogeneous cDNA" 1990 Proc. Natl. Acad. Sci. USA 87:1663-1667.
Wang, et al. "Phylogeny of mRNA capping enzymes" 1997 Proc. Natl. Acad. Sci. USA 94: 9573-8.
Westman, et al. "The antiviral drug ribavirin does not mimic the 7-methylguanosine moiety of the mRNA cap structure in vitro" 2005 RNA 11: 1505-1513.
Wilusz, et al. "A 64 kd nuclear protein binds to RNA segments that include the AAUAAA polyadenylation motif" 1988 Cell 52: 221-8.
Yan et al. "Ribavirin is not a functional mimic of the 7-methyl guanosine mRNA cap" 2005 RNA 11: 1238-1244.
Yisraeli, et al. "Synthesis of long, capped transcripts in vitro by SP6 and T7 RNA polymerases" 1989 Meth. Enzymol. 180: 42-50.
Yu, et al "Mutational analysis of the RNA triphosphatase component of vaccinia virus mRNA capping enzyme" 1996 Virology 70: 6162-6168.
Lockless et al., "Recognition of Capped RNA Substrates by VP39, the Vaccinia Virus-Encoded mRNA Cap-Specific 2'-O-Methyltransferase," Biochemistry, 1998, 37:8564-8574.
Murthy, et al. "A macromolecular delivery vehicle for protein-based vaccines: acid-degradable protein-loaded microgels," Proc Natl Acad Sci U S A. Apr. 29, 2003;100(9):4995-5000.
Banerjee "5'-terminal cap structure in eucaryotic messenger ribonucleic acids" 1980 Microbiol. Rev. 44: 175-205.
Bisaillon and Lemay "Viral and cellular enzymes involved in synthesis of mRNA cap structure" 1997 Virology 236: 1-7.
Boczkowski et al., "Dendritic cells pulsed with RNA are potent antigen-presenting cells in vitro and in vivo" 1996 J. Exp. Med. 184: 465-472.
Bougie and Bisaillon "The broad spectrum antiviral nucleoside ribavirin as a substrate for a viral RNA capping enzyme" 2004 J. Biol. Chem. 279: 22124-22130.
Carralot et al. "Production and characterization of amplified tumor-derived cRNA libraries to be used as vaccines against metastatic melanomas" Genetic Vaccines and Therapy 3: 6, 2005.
Contreras et al., "Simple, efficient in vitro synthesis of capped RNA useful for direct expression of cloned eukaryotic genes" 1982 Nucl. Acids Res. 10: 6353-62.
Drummond et al. "The effect of capping and polyadenylation on the stability, movement and translation of synthetic messenger RNAs in *Xenopus* oocytes" 1985 Nucleic Acids Res. 13: 7375-94.
Eberwine et al. "Analysis of gene expression in single live neurons" 1992 Proc. Natl. Acad. Sci. USA 89:3010-3014.
Edery et al. "Cap-dependent RNA splicing in a HeLa nuclear extract" 1985 Proc. Natl. Acad. Sci. USA 82: 7590-7594.
Edmonds "Polyadenylate polymerases" 1990 Methods Enzymol., 181; 161-70.
Filipowicz "Functions of the 5,-terminal m7G cap in eukaryotic mRNA" FEBS Lett., vol. 96, pp. 1-11 (1978).
Fischer, et al. "Diversity in the signals required for nuclear accumulation of U snRNPs and variety in the pathways of nuclear transport" 1991 J. Cell Biol. 113: 705-714.
Fresco and Buratowski "Conditional mutants of the yeast mRNA capping enzyme show that the cap enhances, but is not required for, mRNA splicing" 1996 RNA 2: 584-596.
Furuichi et al., "5'-Terminal structure and mRNA stability" 1977 Nature 266: 235-9.
Furuichi, et al. "Synthesis and translation of mRNA containing 5'-terminal 7-ethylguanosine cap" 1979 J. Biol. Chem., 254: 6732-6738.
Gershon "(A)-tail of two polymerase structures" 2000 Nature Structural Biol. 7: 819-821.
Gilboa, et al. "Cancer immunotherapy with mRNA-transfected dendritic cells" 2004 J. Immunol. Rev. 199: 251-263.
Gingras et al. "eIF4 initiation factors: effectors of mRNA recruitment to ribosomes and regulators of translation" 1999 Ann. Rev. Biochem. 68: 913-963.
Ginsberg, et al. "Predominance of neuronal mRNAs in individual Alzheimer's disease senile plaques" 1999 Ann. Neurol. 45:174-181.
Ginsberg, et al. "Expression profile of transcripts in Alzheimer's disease tangle-bearing CA1 neurons" 2000 Ann. Neurol. 48:77-87.
Green, et al. "Human beta-globin pre-mRNA synthesized in vitro is accurately spliced in *Xenopus* oocyte nuclei" 1983 Cell 32: 681-694.
Grudzien et al. "Differential inhibition of mRNA degradation pathways by novel cap analogs" 2006 J. Biol. Chem. 281: 1857-1867.
Grudzien, et al. "Novel cap analogs for in vitro synthesis of mRNAs with high translational efficiency" 2004 RNA 10: 1479-1487.
Hamm et al. "The trimethylguanosine cap structure of U1 snRNA is a component of a bipartite nuclear targeting signal" 1990 Cell 62: 569-577.
Harris et al. "An improved RNA amplification procedure results in increased yield of autologous RNA transfected dendritic cell-based vaccine" 2005 BBA 1724: 127-136.
Heiser et al. "Autologous dendritic cells transfected with prostate-specific antigen RNA stimulate CTL responses against metastatic prostate tumors" 2002 J. Clinical Investigation 109: 409-417.
Higman et al. "The mRNA (guanine-7-)methyltransferase domain of the vaccinia virus mRNA capping enzyme. Expression in *Escherichia coli* and structural and kinetic comparison to the intact capping enzyme" 1994 J. Biol. Chem. 269: 14974-14981.
Higman et al. "The vaccinia virus mRNA (guanine-N7-)-methyltransferase requires both subunits of the mRNA capping enzyme for activity" 1992 J. Biol. Chem. 267: 16430-7.
Jemielity et al. "Novel "anti-reverse" cap analogs with superior translational properties" 2003 RNA 9: 1108-1122.
Kalek et al. "Enzymatically Stable 5' mRNA Cap Analogs: Synthesis and Binding Studies with Human DcpS Decapping Enzyme" 2006 Bioorganic & Medicinal Chemistry vol. 14 pp. 3223-3230.
Konarska et al. "Recognition of cap structure in splicing in vitro of mRNA precursors" 1984 Cell 38: 731-736.
Krieg et al. "Functional messenger RNAs are produced by SP6 in vitro transcription of cloned cDNAs" 1984 Nucleic Acids Res. 12: 7057-70.
Kuge et al. "Cap ribose methylation of c-mos mRNA stimulates translation and oocyte maturation in *Xenopus laevis*" 1998 Nucleic Acids Res. 26: 3208-14.
Maroney et al. "Most mRNAs in the nematode *Ascaris lumbricoides* are trans-spliced: a role for spliced leader addition in translational efficiency" 1995 RNA 1: 714-723.
Martin et al. "Purification of mRNA guanylyltransferase and mRNA (guanine-7-) methyltransferase from vaccinia virions" 1975 J Biol Chem 250: 9322-9329.
Mattaj "Cap trimethylation of U snRNA is cytoplasmic and dependent on U snRNP protein binding" 1986 Cell 46: 905-911.
Melton et al. "Efficient in vitro synthesis of biologically active RNA and RNA hybridization probes from plasmids containing a bacteriophage SP6 promoter" 1984 Nucleic Acids Res. 12: 7035-56.
Mockey et al. "mRNA transfection of dendritic cells: synergistic effect of ARCA mRNA capping with Poly(A) chains in cis and in trans for a high protein expression level" 2006 Biochem. Biophys. Res. Comm. 340: 1062-1068.
Murakawa et al. "Direct detection of HIV-1 RNA from AIDS and ARC patient samples" 1988 DNA 7:287-295.
Myette et al. "Domain structure of the vaccinia virus mRNA capping enzyme. Expression in *Escherichia coli* of a subdomain possessing the RNA 5'-triphosphatase and guanylyltransferase activities and a kinetic comparison to the full-size enzyme" 1996 J. Biol. Chem. 271: 11936-44.
Ozawa et al. "Amplification and analysis of cDNA generated from a single cell by 5'-RACE: application to isolation of antibody heavy and light chain variable gene sequences from single B cells" Biotechniques. Apr. 2006;40(4):469-70, 472, 474.
Pasquinelli et al. "Reverse 5' caps in RNAs made in vitro by phage RNA polymerases" 1995 RNA 1: 957-967.
Paterson, et al. "Efficient translation of prokaryotic mRNAs in a eukaryotic cell-free system requires addition of a cap structure" 1979 Nature 279: 692-6.

(56) References Cited

OTHER PUBLICATIONS

Peng et al. "Synthesis and application of a chain-terminating dinucleotide mRNA cap analog" 2002 Organic Letters 4: 161-164.

Phillips, et al. "Antisense RNA Amplification: A Linear Amplification Method for Analyzing the mRNA Population from Single Living Cells" 1996 Methods in Enzymol. Suppl. 10:283-288.

Rhoads "Signal transduction pathways that regulate eukaryotic protein synthesis" 1999 J. Biol. Chem. 274: 30337-40.

Ross "Messenger RNA turnover in eukaryotic cells" 1988 Mol. Biol. Med. 5: 1-14.

Saha et al. "Yeast-based genetic system for functional analysis of poxvirus mRNA cap methyltransferase" 2003 J. Virology 77: 7300-7307.

Schwer et al. "Accelerated mRNA decay in conditional mutants of yeast mRNA capping enzyme" 1998 Nucleic Acids Res. 26: 2050-2057.

Schwer, et al. "Conditional inactivation of mRNA capping enzyme affects yeast pre-mRNA splicing in vivo" 1996 RNA 2: 574-583.

KITS AND METHODS FOR GENERATING 5' CAPPED RNA

The present invention is a continuation of U.S. patent application Ser. No. 14/185,384, filed Feb. 20, 2014, which is a continuation of U.S. patent application Ser. No. 11/787,352, filed Apr. 16, 2007, which claims priority U.S. Provisional Patent Application Ser. No. 60/792,220, filed Apr. 14, 2006, each of which are herein incorporated by reference in their entireties.

FIELD OF THE INVENTION

The present invention relates to kits and methods for efficiently generating 5' capped RNA having a modified cap nucleotide and uses of such modified-nucleotide-capped RNA molecules. The invention can be used to obtain novel compositions of such modified-nucleotide-capped RNA molecules. In particular, the present invention provides kits and methods for capping RNA using a modified cap nucleotide and a capping enzyme system, such as vaccinia virus capping enzyme. The present invention finds use for in vitro production of 5'-capped RNA having a modified cap nucleotide and for in vitro or in vivo production of polypeptides by in vitro or in vivo translation of such modified-nucleotide-capped RNA for a variety of research, therapeutic, and commercial applications. The invention also provides methods and kits for capturing or isolating uncapped RNA comprising primary RNA transcripts or RNA having a 5'-diphosphate, such as RNA synthesized in vitro or obtained from a biological source, including prokaryotic mRNA that is in a mixture with other prokaryotic and/or eukaryotic nucleic acids. The method for capturing modified-nucleotide-capped RNA also provides methods and kits for obtaining only type-specific or condition-specific modified-nucleotide-capped RNA by cap-dependent subtraction of that portion of the captured modified-nucleotide-capped RNA in cells of one type or condition that is the same as RNA in cells of another type or condition. The invention further provides methods and kits for using a capping enzyme system and modified cap nucleotides for labeling uncapped RNA comprising primary RNA transcripts or RNA having a 5'-diphosphate with detectable dye or enzyme moieties.

BACKGROUND OF THE INVENTION

Most eukaryotic cellular mRNA transcripts and most eukaryotic viral mRNA transcripts are blocked or "capped" at their 5' terminus. In addition to mRNA, some other forms of eukaryotic RNA, such as but not limited to, small nuclear RNA ("snRNA") and pre-micro RNA (i.e. "pre-miRNA", the primary transcripts that are processed to miRNA) are also capped.

A "cap" is a guanine nucleoside that is joined via its 5'-carbon to a triphosphate group that is, in turn, joined to the 5'-carbon of the most 5'-nucleotide of the primary mRNA transcript, and in most eukaryotes, the nitrogen at the 7 position of guanine in the cap nucleotide is methylated. Such a capped transcript can be represented as $m^7G(5')ppp(5')N_1(pN)_x$—OH(3'), or more simply, as $m^7GpppN_1(pN)_x$, where $m^7G$ represents the 7-methylguanosine cap nucleoside, ppp represents the triphosphate bridge between the 5' carbons of the cap nucleoside and the first nucleotide of the primary RNA transcript, and $N_1(pN)_x$—OH(3') represents the primary RNA transcript, of which $N_1$ is the most 5'-nucleotide.

The 5' caps of eukaryotic cellular and viral mRNAs (and some other forms of RNA) play important roles in RNA stability and processing. For example, the cap plays a pivotal role in mRNA metabolism, and is required to varying degrees for processing and maturation of an RNA transcript in the nucleus, transport of mRNA from the nucleus to the cytoplasm, mRNA stability, and efficient translation of the mRNA to protein.

The 5' cap structure is involved in the initiation of protein synthesis of eukaryotic cellular and eukaryotic viral mRNAs and in mRNA processing and stability in vivo (e.g., see, Cell 9: 645-653, 1976; Furuichi, et al., Nature 266: 235, 1977; Federation of Experimental Biologists Society Letter 96: 1-11, 1978; Prog. Nuc. Acid Res. 35: 173-207, 1988). Specific cap binding proteins exist that are components of the machinery required for initiation of translation of an mRNA (e.g., see Cell 40: 223-24, 1985; Prog. Nuc. Acid Res. 35: 173-207, 1988). The cap of mRNA is recognized by the translational initiation factor eIF4E (Gingras, et al., Ann. Rev. Biochem. 68: 913-963, 1999; Rhoads, R E, J. Biol. Chem. 274: 30337-3040, 1999). Thus, RNA prepared (e.g., in vitro) for introduction into eukaryotic cells (e.g., via microinjection into oocytes or transfection into cells) should be capped.

Also, many viral RNAs are infectious only when capped, and uncapped RNAs introduced into cells via transfection or microinjection are rapidly degraded by cellular RNases (e.g., see Krieg, and Melton, Nucleic Acids Res. 12: 7057, 1984; Drummond, et al. Nucleic Acids Res. 13: 7375, 1979).

The 5' cap structure provides resistance to 5'-exonuclease activity and its absence results in rapid degradation of the mRNA (e.g., see Mol. Biol. Med. 5: 1-14, 1988; Cell 32: 681-694, 1983). Since the primary transcripts of many eukaryotic cellular genes and eukaryotic viral genes require processing to remove intervening sequences (introns) within the coding regions of these transcripts, the benefit of the cap also extends to stabilization of such pre-mRNA. This was demonstrated using mutants of capping enzymes in the budding yeast *Saccharomyces cerevisiae*. For example, it was shown that the presence of a cap on pre-mRNA enhanced in vivo splicing of pre-mRNA in yeast, but was not required for splicing, either in vivo or using in vitro yeast splicing systems (Fresco, L D and Buratowski, S, RNA 2: 584-596, 1996; Schwer, B et al., Nucleic Acids Res. 26: 2050-2057, 1998; Schwer, B and Shuman, S, RNA 2: 574-583, 1996). The enhancement of splicing was primarily due to the increased stability of the pre-mRNA since, in the absence of a cap, the pre-mRNA was rapidly degraded by 5' exoribonuclease (Schwer, B, Nucleic Acids Res. 26: 2050-2057, 1998). Thus, it is also beneficial that transcripts synthesized for in vitro RNA splicing experiments are capped.

In vitro, capped RNAs have been reported to be translated more efficiently than uncapped transcripts in a variety of in vitro translation systems, such as rabbit reticulocyte lysate or wheat germ translation systems (e.g., see Paterson and Rosenberg, Nature 279: 692, 1979). This effect is also believed to be due in part to protection of the RNA from exoribonucleases present in the in vitro translation system, as well as other factors. Therefore the importance of the cap can vary with the particular translation system and its method of preparation. In any case, the use of capped transcripts can be beneficial in many cases.

The synthesis of capped RNA transcripts in vitro provides considerable value and importance for a variety of functions and applications, such as for in vitro and in vivo protein synthesis. In addition to being capped, most eukaryotic cellular and viral mRNAs have poly(A) tails on their 3' termini. There appears to be a synergy between the 3' poly(A) tail and the 5'-cap in increasing mRNA stability and translation. Without being bound by theory, this synergy is believed to involve an interaction between the poly(A) binding protein and the N-terminal part of the eIF4G cap binding protein, leading to mRNA circularization via a complex between the cap, the cap binding protein, the poly(A) binding protein, and the poly(A) tail. Some aspects and applications of this synergy are presented and discussed by Mockey, M et al. (Biochem. Biophys. Res. Comm. 340: 1062, 2006).

While capped mRNA remains in the cytoplasm after being exported from the nucleus, some other RNAs, such as some snRNAs have caps that are further methylated and then imported back into the nucleus, where they are involved in splicing of pre-mRNA (Mattaj, Cell 46: 905-911, 1986; Hamm et al., Cell 62: 569-577, 1990; Fischer, et al., J. Cell Biol. 113: 705-714, 1991). Transcripts with trimethylated caps have been shown to be translated with higher efficiency using *Ascaris lumbicoides* extracts in vitro (Maroney et al., RNA 1: 714-723, 1995).

In vivo, capping of a 5'-triphosphorylated primary mRNA transcript occurs via several enzymatic steps (e.g., see Martin, S A et al., J. Biol. Chem. 250: 9322, 1975; Myette, J R and Niles, E G, J. Biol. Chem. 271: 11936, 1996; M A Higman, et al., J. Biol. Chem. 267: 16430, 1992).

The following enzymatic reactions are involved in capping of eukaryotic mRNA:

(1) RNA triphosphatase cleaves the 5'-triphosphate of mRNA to a diphosphate,

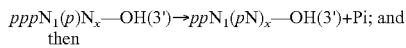

then (2) RNA guanyltransferase catalyzes joining of GTP to the 5'-diphosphate of the most 5' nucleotide ($N_1$) of the mRNA,

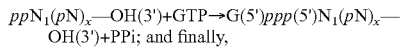

(3) guanine-7-methyltransferase, using S-adenosyl-methionine (AdoMet) as a co-factor, catalyzes methylation of the 7-nitrogen of guanine in the cap nucleotide,

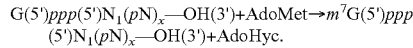

RNA that results from the action of the RNA triphosphatase and the RNA guanyltransferase enzymatic activities, as well as RNA that is additionally methylated by the guanine-7-methyltransferase enzymatic activity, is referred to as "5' capped RNA" or "capped RNA", and the combination of one or more polypeptides having the enzymatic activities that result in "capped RNA" are referred to as "capping enzyme systems" or, more simply, as "capping enzymes" herein. Capping enzyme systems, including cloned forms of such enzymes, have been identified and purified from many sources and are well known in the art (e.g., see Shuman, S, Prog. Nucleic Acid Res. Mol. Biol. 66: 1-40, 2001; Shuman, S, Prog. Nucleic Acid Res. Mol. Biol. 50: 101-129, 1995; and Banerjee, A K, Microbiol. Rev. 44: 175, 1980). The capped RNA that results from the addition of the cap nucleotide to the 5'-end of primary RNA by a capping enzyme system has been referred to as capped RNA having a "cap 0 structure" (e.g., see Higman, M A et al., J. Biol. Chem. 269: 14974-14981, 1994; Myette, J R and Niles, E G, J. Biol. Chem. 271: 11936-11944, 1996). Capping enzyme systems have been used to synthesize capped RNA having a cap 0 structure in vitro (e.g., see Shuman, S et al., J. Biol. Chem. 255: 11588, 1980; Wang, S P et al., Proc. Natl. Acad. Sci. USA 94: 9573, 1997; Higman M. A. et al., J. Biol. Chem. 267: 16430, 1992; Higman M. A. et al., J. Biol. Chem. 269: 14974, 1994; Myette, J. R. and Niles, E. G., J. Biol. Chem. 271: 11936, 1996; and references therein).

Capped RNA having a cap 0 structure can be further transformed in vivo or in vitro to a "cap I" structure by the action of an enzyme with mRNA (nucleoside-2'-O—) methyltransferase activity (e.g., see Higman, M A et al., J. Biol. Chem. 269: 14974-14981, 1994; Myette, J R and Niles, E G, J. Biol. Chem. 271: 11936-11944, 1996). A capped RNA with a "cap I" structure, in addition to having a 7-methyl-G cap nucleotide as the 5' ultimate cap nucleotide, also has a 2'-O-methyl group on the 5'-penultimate nucleotide. For example, vaccinia mRNA (nucleoside-2'-O) methyltransferase can catalyze methylation of the 2'-hydroxyl group of the 5'-penultimate nucleotide of 5'-capped RNA having a cap 0 structure, as follows:

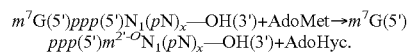

Dimethylated capped RNAs having a cap I structure have been reported to be translated more efficiently than 7-methylguanosine-capped RNAs having a cap 0 structure (e.g., see Kuge, H et al., Nucleic Acids Res. 26: 3208, 1998).

Most commonly, the RNA that has been used for in vitro capping reactions has been obtained using a T7, T3 or SP6 RNA polymerase for in vitro transcription of a template that is downstream of the respective RNA polymerase promoter, but primary RNA from other sources can also be used.

During the 1970s and early 1980s, capping enzymes were used as reagents for capping of RNAs. However, in the mid-1980s, this method for synthesis of capped transcripts was supplanted by the use of a dinucleotide cap analog to prime in vitro transcription with phage RNA polymerases (Melton, D et al., Nucleic Acids Res. 12: 7035, 1984). Since that time, post-transcriptional capping of RNA in an in vitro reaction using a capping enzyme system has not been widely used except by laboratories studying capping enzymes, and the most frequently used in vitro method to make capped RNAs having a cap 0 structure has been transcription of a DNA template with either a bacterial RNA polymerase or a bacteriophage RNA polymerase in the presence of all four ribonucleoside triphosphates and a "dinucleotide cap analog", also referred to as a "cap analog." A cap analog, such as $m^7G(5')ppp(5')G$ (also referred to as "$m^7GpppG$"), is a dinucleotide consisting of an outer cap nucleoside, such as 7-methyl-guanosine ($m^7G$), and the nucleotide corresponding to the first nucleotide of the primary transcript (e.g., in this case, G). This cap analog is often used because the primary nucleotide (i.e., the most 5' nucleotide) of most, but not all, primary RNA transcripts synthesized using phage RNA polymerase transcription systems is guanosine ribonucleotide.

Most commonly, capped RNAs are synthesized using this method by cell-free transcription of DNA templates (e.g., Contreras, R. et al., Nucl. Acids Res. 10: 6353, 1982; Yisraeli J. et al., Meth. Enzymol. 180: 42-50, 1989; and Melton, D. et al., Nucl. Acids Res. 12: 7035-7056, 1984). When capping is carried out using a cap analog in such an in vitro transcription reaction, the RNA polymerase initiates transcription by extension of the 3'-OH of the cap analog, rather than by extension of the 3'-OH of an initiating nucleoside triphosphate. Thus, if the $m^7GpppG$ cap analog is used, the initial product is expected to be $m^7GpppGpN$. The alternative, GTP-initiated product pppGpN is suppressed by setting the ratio of $m^7GpppG$ to GTP between about 4-to-1 to about 10-to-1 in the transcription reaction mixture.

However, when using a cap analog in an in vitro transcription reaction to make capped RNA, Pasquinelli, A. et al. (RNA 1: 957-967, 1995) found that, in addition to obtaining the expected $m^7GpppGpN$ product, approximately one-third to one-half of the capped RNA products made with this m⁷GpppG cap analog actually had the "reverse cap" Gpppm⁷GpN, demonstrating that bacteriophage RNA polymerases can also use the 3'-OH of the 7-methylguanosine moiety of m⁷GpppG to initiate transcription. Such reverse-capped RNA molecules behaved abnormally. For example, Pasquinelli et al. reported that when reverse-capped pre-U1 RNA transcripts were injected into *Xenopus laevis* nuclei, they were exported more slowly than natural transcripts. Similarly, cytoplasmic reverse-capped U1 RNAs in the cytoplasm were not properly imported into the nucleus. Because the resulting capped RNAs contain about one-third to one-half reverse caps, the overall translational activity of such in vitro-synthesized mRNA is reduced and other functional properties of the mRNA may also be affected. Thus, translation of in vitro-synthesized mRNAs having such reverse caps is impaired.

To address the problem of dinucleotide cap analogs being incorporated in the reverse orientation during in vitro transcription reactions, Stepinski et al. (Nucleosides and Nucleotides 14: 717-721, 1995) and Peng et al. (Organic Letters 4: 161-164, 2002) synthesized dinucleotide cap analogs which could only be incorporated in the correct orientation because the 3'-OH of the cap nucleotide was eliminated or blocked by substitution. Since they could not be incorporated in the reverse orientation, Stepinski et al. referred to these dinucleotide cap analogs as "anti-reverse cap analogs" or "ARCAs". Using RNA transcripts made in vitro in the presence of several different ARCAs, including $m_2^{7,3'-O}GpppG$, it has been demonstrated that ARCA-capped RNAs result in higher translational efficiencies than RNA transcripts made in the presence of the standard m⁷GpppG cap analog, both for RNA transcripts translated in a rabbit reticulocyte lysate in vitro (Stepinski et al., Nucleosides and Nucleotides 14: 717-721, 1995; U.S. Patent Application No. 200301945759; Jemielity et al., RNA 9: 1108-1122, 2003; Grudzien et al., RNA 10: 1479-1487; 2004) and for RNA transcripts electroporated into mouse mammary epithelial (MM3MG) cells and translated in vivo (Grudzien et al., J. Biol. Chem. 281: 1857-1867, 2006). Mockey et al. (Biochem. Biophys. Res. Comm. 340: 1062-1068, 2006) also found that lipofection of mouse dendritic cells with a luciferase mRNA having a 3'-poly(A) tail of defined length was translated with higher efficiency if the mRNA used was capped using the $m_2^{7,3'-O}GpppG$ ARCA than if it was capped using the standard m⁷GpppG cap analog. The dinucleotide cap analog $m_2^{7,2'-O}GpppG$ is also incorporated only in the correct orientation and is therefore an ARCA (Jemielity et al., RNA 9: 1108-1122, 2003; Grudzien et al., RNA 10: 1479-1487; 2004). RNA capped with $m_2^{7,2'-O}GpppG$ was also translated in vitro with higher efficiency than the standard m⁷GpppG cap analog (Jemielity et al., RNA 9: 1108-1122, 2003; Grudzien et al., RNA 10: 1479-1487; 2004). Thus, mRNA having a cap nucleotide that is methylated in the 2' or 3'-position was beneficial for improving translational efficiency of mRNA in vitro and in vivo.

However, although RNA can be capped by in vitro transcription of a DNA template in the presence of an ARCA, this approach has several drawbacks. First, the chemical syntheses of ARCAs (e.g., see Jemielity, J et al., RNA: 1108, 2003) are difficult (~6 synthetic steps), time-consuming (~12 weeks) and expensive. Also, once the ARCA is obtained, the in vitro transcription reaction is wasteful and inefficient. Due to the limiting amount of GTP in the reaction (since 80% or more of the GTP is typically substituted by ARCA), the RNA yield of the in vitro transcription with a cap analog is at best 33% of the RNA yield obtained without cap analog. Not only is the RNA yield lower using a cap analog, but also <80% of the RNA obtained is capped. Still further, the fact that the cap analog can never be incorporated to 100% limits the purity of the capped RNA product, necessitating more work to purify the product and increasing the risk that the capped RNA product will still be contaminated with impurities, including unincorporated cap analog. This is particularly detrimental if the capped RNA is to be used for medical applications, such as for therapeutics, or for clinical research, since the contaminants may produce undesired effects. Thus, there is a need for compositions and methods that provide consistent 5' capping of RNA in a correct orientation and that increase incorporation efficiency, such as in order to improve the stability of in vitro-generated RNA transcripts (e.g., thereby increasing translational efficiency).

Also, little was known about the possibility of using a modified cap nucleotide as a substrate for a capping enzyme system to make RNA with improved properties. Published work related to use of a modified nucleotide as a substrate for a capping enzyme discouraged this approach. For example, the data of Shuman et al. (J. Biol. Chem. 255: 11588, 1980) indicated that only GTP was a good substrate for the RNA guanyltransferase activity of the vaccinia capping enzyme system; UTP, CTP, ATP, ITP, GDP, GMP and N⁷-methyl-GTP could not be used in place of GTP in an in vitro capping reaction. They found that 2'-dGTP seemed to have slight activity in a [³²P]-PPi exchange assay in the presence of permeabilized vaccinia virions, indicating that it might be a substrate for capping, but it was only approximately 6% as active as GTP in this assay. Thus, 2'-dGTP appeared to be incorporated into capped RNA, but inefficiently. Bougie, I and Bisaillon, M (J. Biol. Chem. 279: 22124, 2004) found that the intracellular triphosphate metabolite of the antiviral nucleoside ribavirin, a nucleoside with a monocyclic base analog, was of ribavirin, was a substrate for viral capping enzyme; the ribavirin-capped RNA was more stable than uncapped RNA, but was not a functional mimic of the N⁷-methyl-guanosine cap with respect to translation (Yan, Y et al., RNA 11: 1238-1244, 2005; Westman, B et al., RNA 11: 1505-1513, 2005).

It would be highly desirable if there was an easier, faster, less expensive, higher yield way to make capped RNA transcripts, including modified nucleotide-capped RNA transcripts, particularly transcripts that are of a higher purity, for a variety of applications, including medical applications.

Still further, in vitro transcription in the presence of an ARCA results in RNA having a cap 0 structure. However, a capped RNA with a cap I structure could not be synthesized using an m⁷Gpppm²'-OG cap analog (Pasquinelli, RNA 1: 957, 1995). Also, ARCA-capped RNA has not been used as a substrate for methylation of the 5'-penultimate nucleotide of the capped RNA using mRNA (nucleoside-2'-O—) methyltransferase to obtain capped RNA having a cap I structure, which is unfortunate because 2'-O-methylation has been shown to significantly enhance translation compared to capped RNA having a type 0 structure. Therefore, it would also be highly desirable if there was a way to make modified-nucleotide-capped RNA having a cap I structure for a variety of applications, including medical applications.

DEFINITIONS

To facilitate an understanding of the present invention, a number of terms and phrases are defined below:

"Affinity binding molecules" or "specific binding pair" herein means two molecules that have affinity for and "bind" to each other under certain conditions, referred to as "binding conditions. Biotin and streptavidin or avidin are examples of a "specific binding pair" or "affinity binding molecules", but the invention is not limited to use of this particular specific binding pair. In many embodiments of the present invention, one member of a particular specific binding pair is referred to as the "affinity tag molecule" or the "affinity tag" and the other as the "affinity-tag-binding molecule" or the "affinity tag binding molecule". For example, but without limitation, in some embodiments, biotin is referred to as the affinity tag or affinity tag molecule, and a streptavidin or avidin molecule, whether it is free, attached to a surface, attached to another molecule, or labeled with a detectable molecule such as a dye, is referred to as the affinity-tag-binding molecule. In other embodiments, streptavidin is the affinity tag and biotin is the affinity-tag-binding molecule, since streptavidin and binding function together as a specific binding pair or as affinity binding molecules. A wide variety of other specific binding pairs or affinity binding molecules, including both affinity tag molecules and affinity-tag-binding molecules, are known in the art (e.g., see U.S. Pat. No. 6,562,575), which can be used in the present invention. For example, an antigen (which itself may be an antibody) and an antibody, including a monoclonal antibody, that binds the antigen is a specific binding pair. Also, an antibody and an antibody binding protein, such as *Staphylococcus aureus* Protein A, can be employed as a specific binding pair. Other examples of specific binding pairs include, but are not limited to, a carbohydrate moiety which is bound specifically by a lectin and the lectin; a hormone and a receptor for the hormone; and an enzyme and an inhibitor of the enzyme. Usually, molecules that comprise a specific binding pair interact with each other only through non-covalent bonds such as hydrogen-bonding, hydrophobic interactions (including stacking of aromatic molecules), van der Waals forces, and salt bridges. Without being bound by theory, it is believed in the art that these kinds of non-covalent bonds result in binding, in part due to complementary shapes or structures of the molecules involved in the binding pair. The term "binding" according to the invention refers to the interaction between an affinity binding molecules or specific binding pairs (e.g., between biotin as an affinity tag molecule and streptavidin as an affinity-tag-binding molecule) as a result of non-covalent bonds, such as, but not limited to, hydrogen bonds, hydrophobic interactions, van der Waals bonds, and ionic bonds. Based on the definition for "binding," and the wide variety of affinity binding molecules or specific binding pairs, it is clear that "binding conditions" vary for different specific binding pairs. Those skilled in the art can easily determine conditions whereby, in a sample, binding occurs between the affinity binding molecules. In particular, those skilled in the art can easily determine conditions whereby binding between affinity binding molecules that would be considered in the art to be "specific binding" can be made to occur. As understood in the art, such specificity is usually due to the higher affinity between the affinity binding molecules than for other substances and components (e.g., vessel walls, solid supports) in a sample. In certain cases, the specificity might also involve, or might be due to, a significantly more rapid association of affinity binding molecules than with other substances and components in a sample.

In some embodiments of the invention, an "affinity tag reagent" or and "affinity tag having a reactive moiety" is used, by which we mean herein, a molecule that comprises both an affinity tag and a reactive chemical group or moiety that is capable of reacting with one or more atoms or groups of the molecule with which it reacts to form one or more covalent chemical bonds between the molecule comprising the affinity tag and the molecule with which it reacts. By way of example, but without limitation, in some embodiments, the affinity tag reagent is an acylating reagent (e.g., an N-hydroxysuccinimidyl ester), wherein the affinity tag is chemically joined to an atom in the molecule with which it reacts via an acyl linkage. In other embodiments, the affinity tag reagent is an alkylating reagent, group, wherein the affinity tag is chemically joined to an atom in the molecule with which it reacts via an alkyl linkage. In other embodiments, the affinity tag reagent reacts via an electrocyclic type of chemical reaction, such as a 1,3-dipolar cycloaddition (e.g., cycloaddition of an alkyne with an azide). Thus, the term "reactive" moiety with respect to, for example, an "affinity tag reagent" or "affinity tag having a reactive moiety" is used to refer to a moiety or group that is involved in or responsible for the chemical reaction whereby a molecule comprising the affinity tag reacts chemically to form a covalent chemical bond with one or more atoms in the molecule with which it reacts, rather than to the binding that results between affinity binding molecules due to non-covalent forces and bonds.

When we refer to attaching the "affinity-tag-binding molecule" or the "affinity tag binding molecule", such as streptavidin or avidin, directly to the surface, we usually, but not always mean that the affinity-tag-binding molecule is covalently attached to the surface by means of a chemical linker that is joined to the surface and to the affinity-tag-binding molecule. When we refer to attaching the "affinity-tag-binding molecule" or the "affinity tag binding molecule", such as streptavidin or avidin, indirectly to the surface, we mean that the affinity-tag-binding molecule is bound to another molecule with which it has affinity (e.g., an anti-streptavidin antibody) that is in turn bound to the surface. In some embodiments, the affinity-tag-binding molecule, such as streptavidin or avidin, is not attached to a surface, but is bound by another molecule, such as an antibody or Protein A, and the biotinylated modified-nucleotide-capped RNA is recovered by precipitation or by binding to a second antibody or other molecule using methods and compositions known in the art.

A "cap nucleotide" of the present invention means a nucleoside-5'-triphosphate that, under suitable reaction conditions, is used as a substrate by a capping enzyme system and that is thereby joined to the 5'-end of an uncapped RNA comprising primary RNA transcripts or RNA having a 5'-diphosphate. The nucleotide that is so joined to the RNA is also referred to as a "cap nucleotide" herein.

A "capping enzyme system" or a "capping enzyme" of the present invention means the combination of one or more polypeptides having enzymatic activities that, in the presence of a cap nucleotide, including a modified cap nucleotide, and suitable reaction conditions, results in synthesis of capped RNA, including a modified-nucleotide-capped RNA, having a cap 0 structure. In general, a capping enzyme system or capping enzyme of the invention comprises RNA triphosphatase and RNA guanyltransferase enzymatic activities, and optionally, the capping enzyme system can also comprise RNA guanine-7-methyltransferase enzymatic activity. Capping enzyme systems that can be used for the present invention are well known in the art (e.g., see Shuman, S, Prog. Nucleic Acid Res. Mol. Biol. 66: 1-40, 2001; Shuman, S, Prog. Nucleic Acid Res. Mol. Biol. 50: 101-129, 1995; Bisaillon, M and Lemay, G, Virology 236: 1-7, 1997; Banerjee, A K, Microbiol. Rev. 44: 175-205, 1980). Without limiting the invention, vaccinia virus capping enzyme and poxvirus capping enzymes having these enzymatic activities are known in the art that can be used as a capping enzyme system of the invention, including both full-length and enzymatically active portions thereof, which capping enzymes have been identified, purified, characterized, cloned, and expressed from a clone (e.g., see Martin S A et al., J Biol Chem 250:

9322-9329, 1975; Shuman, J Biol Chem 265: 11960-11966, 1990; Shuman and Morham, 265: 11967-11972, 1990; M A Higman, et al., J. Biol. Chem. 267: 16430, 1992; Myette, J R and Niles, E G, J. Biol. Chem. 271: 11936, 1996). Thus, in some embodiments, the capping enzyme, such as vaccinia virus capping enzyme or capping enzyme encoded by a poxvirus capping enzyme gene known in the art, is purified from a clone that expresses a nucleic acid or polynucleotide sequence encoding the full-length gene or an enzymatically active portion thereof. The present invention is not limited by the type of capping enzyme utilized. For example, in some embodiments in which vaccinia virus capping enzyme is used, the capping enzyme is purified from vaccinia virus, whereas in other embodiments, the vaccinia capping enzyme is a purified recombinant vaccinia virus capping enzyme. In some embodiments, the vaccinia virus capping enzyme is a mutant or variant of the wild-type enzyme (e.g., that exhibits greater enzymatic activity compared to wild-type capping enzyme). Variants, including allelic variants, muteins, analogs and fragments capable of functioning as the provided capping enzyme are known in the art and are also contemplated by this invention. The active sites for the RNA triphosphatase, RNA guanyltransferase and guanine-7-methyltransferase enzymatic activities can be on single-component polypeptides, 2-component polypeptides (typically having RNA triphosphatase and RNA guanyltransferase activities), or on a 3-component polypeptide, from a cloned or a wild-type source. In view of the fact that genes encoding RNA triphosphatase, RNA guanyltransferase and guanine-7-methyltransferase from one source can complement deletions in one or all of these genes from another source (e.g., see reference to unpublished work of Schwer et al. on p. 3 of Shuman, S, Prog. Nucleic Acid Res. Mol. Biol. 66: 1-40, 2001 with respect to *Saccharomyces cerevisiae, Schizosaccharomyces pombe* and *Candida albicans*), the capping enzyme system can originate from one wild type source, or one or more of the RNA triphosphatase, RNA guanyltransferase, and/or guanine-7-methyltransferase activities can comprise a polypeptide from a different source, which polypeptides can each be encoded by a DNA sequence originating from the same biological source or by a DNA sequence originating from a different biological source. In preferred embodiments, the RNA triphosphatase component of the capping enzyme comprises a divalent cation-dependent RNA triphosphatase encoded by a DNA virus or fungus having conserved motifs A, B, and C. In some preferred embodiments, the RNA triphosphatase is encoded by a poxvirus gene. In some preferred embodiments, the RNA triphosphatase is encoded by a vaccinia virus gene. However, the invention is not limited to a divalent cation-dependent RNA triphosphatase encoded by a DNA virus or fungus having conserved motifs A, B, and C (see Shuman, S, Prog. Nucleic Acid Res. Mol. Biol. 66: 1-40, 2001); in some embodiments the RNA triphosphatase comprises a divalent cation-independent RNA triphosphatase encoded by a DNA derived from a nematode, mammalian or other metazoan source, so long as the RNA triphosphatase removes a gamma phosphate of a triphosphate-terminated RNA to form an RNA with a 5'-diphosphate terminus. In view of the fact that vaccinia virus RNA triphosphatase-defective mutants can transfer GMP to 5'-triphosphate RNA ends to produce a cap with a tetraphosphate linkage (Yu, L and Shuman, S, J. Virology 70: 6162-6168, 1996) and that RNA with tetraphosphate caps can be translated with good efficiency (e.g., Grudzien et al., RNA 10: 1479, 2004), the capping enzyme system can lack RNA triphosphatase activity in some embodiments. RNA guanyltransferases of capping enzyme systems are structurally and mechanistically conserved among fungi, metazoans, protozoa, and DNA viruses (Shuman, S, Prog. Nucleic Acid Res. Mol. Biol. 66: 1-40, 2001). In some embodiments of the invention, the capping enzyme has a conserved motif I consisting of the amino acid sequence KxDGxx (SEQ ID NO:1). In some embodiments, the sixth (6th) position of said motif I is not arginine. Motif I contains the active site of covalent attachment of GMP to the capping enzyme within the RNA guanyltransferase portion of capping enzyme. In some embodiments, motif I of the capping enzyme has the amino acid sequence KTDG(I/V)(P/G) (SEQ ID NO:2). In some embodiments, motif I of the capping enzyme has the amino acid sequence KTDG(I/V)x (SEQ ID NO:3), wherein the 6th amino acid of said motif I is an amino acid selected from the group consisting of phenylalanine, serine, and leucine. Another conserved motif within the capping enzyme is motif III, which is also within the RNA guanyltransferase portion of the capping enzyme. In some embodiments, the first position of motif III is valine, isoleucine, or tyrosine, the sixth position of motif III is glutamic acid, and the fourth position of motif III is phenylalanine, tyrosine or tryptophan. In one embodiment of the capping enzyme, motif III has the amino acid sequence VVVFGEAV (SEQ ID NO:4). In some embodiments, motif III has the amino acid sequence YRLWCEAV (SEQ ID NO:5). In some embodiments, motif III has the amino acid sequence VT(L/I)YGEA(I/V) (SEQ ID NO:6). In some embodiments, motif III has the amino acid sequence (V/I)YLYAEMR (SEQ ID NO:7). In some embodiments, motif III has the amino acid sequence (V/I)xL(Y/F)GEA(I/V) (SEQ ID NO:8). In some embodiments, the RNA guanyltransferase is encoded by a poxvirus gene. In some embodiments, the RNA guanyltransferase is encoded by a vaccinia virus gene. Whereas the RNA guanyltransferase reaction step is reversible, the methylation step catalyzed by the guanine-7-methyltransferase activity of the capping enzyme is essentially irreversible. Therefore, 7-methylation of the guanine is useful because this step drives the reaction to completion in the direction of cap formation. Methylation of the cap is also useful for enhancing translation of the RNA. The amino acid sequence and structure of guanine-7-methyltransferase enzymes of capping enzymes are highly conserved from DNA viruses to yeast to humans and other metazoans. This is shown by the fact that full-length and some truncated guanine-7-methyltransferase genes that encode *S. pombe, C. albicans* and human capping enzymes can complement deletions of the *S. cerevisiae* capping enzyme guanine-7-methyltransferase, by the fact that the guanine 7-methyltransferase domain of vaccinia virus capping enzyme can function in vivo in lieu of the yeast methyltransferase enzyme (Saha, N et al., J. Virology 77: 7300-7307, 2003), and also by the concordance of mutational effects between the yeast, human and vaccinia enzymes (Shuman, S, Prog. Nucleic Acid Res. Mol. Biol. 66: 1-40, 2001). Therefore, the guanine-7-methyltransferase portion of a capping enzyme of the invention can comprise a wild-type or recombinant enzyme from any of a wide variety of sources. In some embodiments, the guanine-7-methyltransferase is encoded by a poxvirus gene. In some embodiments, the guanine-7-methyltransferase is encoded by a vaccinia virus gene. In some embodiments, the guanine 7-methyltransferase has a conserved IHF amino acid motif. In some embodiments, the guanine 7-methyltransferase has a motif consisting of the amino acid sequence VL(D/E)xGxGxG (SEQ ID NO:9).

By "condition-specific" RNA is meant an RNA sample that, relative to unfractionated condition-derived RNA, has a higher content of RNA that is preferentially present in the condition-specific cell compared with a cell without the condition, wherein a "condition" means a mode or state of being of the organism or cells from which the biological sample is derived (e.g., a cancer condition versus a non-cancerous condition, or a pathogen-infected condition versus an uninfected condition). For example, but without limitation, in some embodiments, the subtracted and amplified RNA can comprise RNA from a condition (e.g., a tumor cell condition) from which RNA that is also present in a normal cell of the same type has been removed by subtractive hybridization and digestion, and then the remaining RNA is amplified using an RNA amplification reaction. In some embodiments of the invention, the uncapped RNA comprising primary RNA transcripts or RNA having a 5'-diphosphate used for synthesizing the modified-nucleotide-capped RNA comprises primary RNA transcripts or RNA having a 5'-diphosphate obtained using the subtractive hybridization and digestion, and RNA amplification methods described in U.S. Pat. No. 5,712,127. In some embodiments, the uncapped RNA comprising primary RNA transcripts or RNA having a 5'-diphosphate used for synthesizing the modified-nucleotide-capped RNA is obtained using the "Cap-Dependent Subtraction" ("CDS") method of the present invention described herein. In some embodiments, the RNA amplification method is an RNA amplification reaction or method as defined herein, such as, but not limited to the terminal tagging method described in U.S. Patent Application No. 20050153333 of Sooknanan. Modified-nucleotide-capped RNA made using the uncapped RNA comprising primary RNA transcripts or RNA having a 5'-diphosphate from such subtractive hybridization and digestion, and RNA amplification reactions is referred to as "condition-specific" (e.g., "tumor-specific"), and, if the modified-nucleotide-capped RNA is subsequently used to synthesize polypeptides (or antigenic epitopes of the polypeptides) by in vitro translation or used to transfect a cell, wherein the modified-nucleotide-capped RNA is translated in vivo, the in vitro-synthesized polypeptides or the polypeptides expressed in vivo in the cells are also called "condition-specific." Similarly, any responses that are expressed in any other cells or organisms that are exposed to the condition-specific modified-nucleotide-capped RNA or condition-specific polypeptides, antigens, or immune responses derived therefrom are referred to as "condition-specific." For example, but without limitation, an antigen-presenting cell (APC) that is loaded with a tumor-specific modified-nucleotide-capped RNA or polypeptides translated therefrom, the APC cell (and any antigenic epitopes presented on its surface) is referred to as tumor-specific. The invention is not limited by the particular condition. For example, but without limitation, in some embodiments, the uncapped RNA is derived from a condition comprising a tumor or cancer condition and the condition-specific uncapped RNA is referred to as "tumor-specific" or "cancer-specific." In other embodiments, the uncapped RNA is derived from a pathogen, such as a bacterial, viral or fungal pathogen, or from a eukaryotic cell that is infected by a bacterial, viral or fungal pathogen, and the uncapped RNA is referred to as "pathogen-specific."

A "modified cap nucleotide" of the present invention means a cap nucleotide comprising: (a) a modified 2'- or 3'-deoxyguanosine-5'-triphosphate, wherein the 2'- or 3'-deoxy position of the sugar moiety is substituted by a group other than a hydroxyl group or a hydrogen, or wherein the O6 oxygen of the guanine base is replaced by a thiol (or mercapto) group or a methylthio (or methylmercapto) group; or (b) a modified guanosine-5'-triphosphate, wherein the 2'- or 3'-hydroxyl group of the ribose is substituted by an alkyl group or, wherein the N1 nitrogen or the O6 oxygen of the guanine base is substituted by an alkyl group or, wherein the O6 oxygen of the guanine base is replaced by a thiol (or mercapto) group or a methylthio (or methylmercapto) group; or (c) 3'-deoxyguanosine. In some preferred embodiments of the invention, the modified cap nucleotide comprises: (i) a modified 2'- or 3'-deoxyguanosine-5'-triphosphate (or guanine 2'- or 3'-deoxyribonucleic acid-5'-triphosphate) wherein the 2'- or 3'-deoxy position of the deoxyribose sugar moiety is substituted with a group comprising an amino group, an azido group, a fluorine group, a methoxy group, a thiol (or mercapto) group or a methylthio (or methylmercapto) group; or (ii) a modified guanosine-5'-triphosphate, wherein the N1 nitrogen or the O6 oxygen of the guanine base is substituted with a methyl group, or wherein the O6 oxygen is replaced by a thiol (or mercapto) group or methylthio (or methylmercapto) group; or (iii) 3'-deoxyguanosine. For the sake of clarity, it will be understood herein that an "alkoxy-substituted deoxyguanosine-5'-triphosphate" can also be referred to as an "O-alkyl-substituted guanosine-5'-triphosphate"; by way of example, but without limitation, 2'-methoxy-2'-deoxyguanosine-5'-triphosphate (2'-methoxy-2'-dGTP) and 3'-methoxy-3'-deoxyguanosine-5'-triphosphate (3'-methoxy-3'-dGTP) can also be referred to herein as 2'-O-methylguanosine-5'-triphosphate (2'-OMe-GTP) and 3'-O-methylguanosine-5'-triphosphate (3'-OMe-GTP), respectively. Following joining of the modified cap nucleotide to the 5'-end of the uncapped RNA comprising primary RNA transcripts or RNA having a 5'-diphosphate, the portion of said modified cap nucleotide that is joined to the uncapped RNA comprising primary RNA transcripts or RNA having a 5'-diphosphate is usually referred to herein as a "modified cap nucleoside" (i.e., without referring to the phosphate groups to which it is joined), but sometimes it is referred to herein as a "modified cap nucleotide".

A "modified-nucleotide-capped RNA" of the present invention is a capped RNA molecule that is synthesized using a capping enzyme system and a modified cap nucleotide, wherein the cap nucleotide on its 5' terminus comprises the modified cap nucleotide.

As used herein, "poxviruses" (or Poxyiridae) means a member of a family of brick-shaped or ovoid viruses that contains a double-stranded DNA genome. For example, but without limitation, poxviruses include vaccinia virus, variola virus, rabbitpox virus, monkeypox virus, ectromelia virus, camelpox virus, cowpox virus, muledeerpox virus, myxoma virus, rabbit fibroma virus, swinepox virus, lumpy skin disease virus, sheeppox virus, canarypox virus, fowlpox virus, orf virus, and bovine papular stomatitis virus, as well as relatives, descendents, variants, and derivatives of such poxviruses.

A "primary RNA" or "primary RNA transcript" means the RNA molecule that is newly synthesized by an RNA polymerase in vivo or in vitro and which RNA molecule has a triphosphate on the 5'-carbon of its most 5' nucleotide.

"Transcription" means the formation or synthesis of an RNA molecule by an RNA polymerase using a DNA molecule as a template.

"Replication" means the formation or synthesis of an RNA molecule by an RNA-dependent RNA polymerase (or "replicase") using an RNA molecule as a template.

An "RNA amplification reaction" or an "RNA amplification method" means a method for increasing the amount of RNA corresponding to one or multiple desired RNA sequences in a sample. For example, in some embodiments, the RNA amplification method comprises: (a) synthesizing first-strand cDNA complementary to the one or more desired RNA molecules by RNA-dependent DNA polymerase extension of one or more primers that anneal to the desired RNA molecules; (b) synthesizing double-stranded cDNA from the first-strand cDNA using a process wherein a functional RNA polymerase promoter is joined thereto; and (c) contacting the double-stranded cDNA with an RNA polymerase that binds to said promoter under transcription conditions whereby RNA corresponding to the one or more desired RNA molecules is obtained. Unless otherwise stated related to a specific embodiment of the invention, an RNA amplification reaction according to the present invention means a sense RNA amplification reaction, meaning an RNA amplification reaction that synthesizes sense RNA (e.g., RNA having the same sequence as an mRNA or other primary RNA transcript, rather than the complement of that sequence). Sense RNA amplification reactions known in the art, which are encompassed within this definition include, but are not limited to, the methods which synthesize sense RNA described in U.S. Patent Application No. 20050153333 of Sooknanan; U.S. Patent Application No. 20030186237 of Ginsberg, Stephen; U.S. Patent Application No. 20040197802 of Dahl and Jendrisak; and U.S. Patent Application No. 20040171041 of Dahl et al, and in Ozawa, T et al. (Biotechniques 40: 469-478, 2006).

A "poly(A) polymerase" ("PAP") means a template-independent RNA polymerase found in most eukaryotes, prokaryotes, and eukaryotic viruses that selectively uses ATP to incorporate AMP residues to 3'-hydroxylated ends of RNA. Since PAP enzymes that have been studied from plants, animals, bacteria and viruses all catalyze the same overall reaction (e.g., see Edmonds, M, Methods Enzymol., 181; 161-180, 1990), are highly conserved structurally (e.g., see Gershon, P, Nature Structural Biol. 7: 819-821, 2000), and lack intrinsic specificity for particular sequences or sizes of RNA molecules if the PAP is separated from proteins that recognize AAUAAA polyadenylation signals (Wilusz, J and Shenk, T, Cell 52: 221, 1988), purified wild-type and recombinant PAP enzymes from any of a variety of sources can be used in the kits and methods of the present invention.

As used herein, a "T7-type" RNA polymerase (RNAP) means T7 RNA polymerase (e.g., see Studier, F W et al., pp. 60-89 in Methods in Enzymology, Vol. 185, ed. by Goeddel, D V, Academic Press, 1990) or an RNAP derived from a "T7-type" bacteriophage, meaning a bacteriophage that has a similar genetic organization to that of bacteriophage T7. Examples of T7-type bacteriophages according to the invention include, but are not limited to *Escherichia coli* phages T3, phi I, phi II, W31, H, Y, A1, 122, cro, C21, C22, and C23; *Pseudomonas putida* phage gh-1; *Salmonella typhimurium* phage SP6; *Serratia marcescens* phages IV; *Citrobacter* phage ViIII; and *Klebsiella* phage No. 11 (Hausmann, Current Topics in Microbiology and Immunology 75:77-109, 1976; Korsten et al., J. Gen. Virol. 43:57-73, 1975; Dunn, et al., Nature New Biology 230:94-96, 1971; Towle, et al., J. Biol. Chem. 250:1723-1733, 1975; Butler and Chamberlin, J. Biol. Chem. 257:5772-5778, 1982), as well as mutant forms of such RNAPs (e.g., Sousa et al., U.S. Pat. No. 5,849,546; Padilla, R and Sousa, R, Nucleic Acids Res., 15: e138, 2002; Sousa, R and Mukherjee, S, Prog Nucleic Acid Res Mol Biol., 73: 1-41, 2003).

With respect to the use of the word "derived", such as for an RNA (including a modified-nucleotide-capped RNA) or a polypeptide that is "derived" from a condition, biological sample, sample, tumor, pathogen, or the like, it is meant that the RNA or polypeptide either was present in the condition, biological sample, sample, tumor, or pathogen, or was made using the RNA in the condition, biological sample, sample, tumor, or pathogen by a process such as, but not limited to, an RNA amplification reaction, wherein the RNA or polypeptide is either encoded by or a copy of all or a portion of the RNA or polypeptide molecules in the original condition, biological sample, sample, tumor, or pathogen. By way of example, but without limitation, such RNA can be from an in vitro transcription or an RNA amplification reaction, with or without cloning of cDNA, rather than being obtained directly from the condition, biological sample, sample, tumor, or pathogen, so long as the original RNA used for the in vitro transcription or an RNA amplification reaction was from the condition, biological sample, sample, tumor, or pathogen.

As used herein, the term "purified" or "to purify" refers to the removal of components (e.g., contaminants) from a sample. For example, nucleic acids are purified by removal of contaminating cellular proteins or other undesired nucleic acid species. The removal of contaminants results in an increase in the percentage of desired nucleic acid in the sample.

As used herein, the term "in vitro" refers to an artificial environment and to processes or reactions that occur within an artificial environment. In vitro environments can consist of, but are not limited to, processes or reactions that occur in a test tube. The term "in vivo" refers to the natural environment and to processes or reactions that occur within a natural environment (e.g., in an animal or a cell).

DESCRIPTION OF THE INVENTION

The description below provides exemplary embodiments of the present invention. It should be understood that the invention is not limited to these exemplary embodiments.
Utility of the Invention Exemplary uses of the invention are provided below. The present invention is not limited to these particular exemplary uses.

In some embodiments, the present invention provides a method comprising: providing an uncapped RNA comprising primary RNA transcripts or RNA having a 5'-diphosphate, a capping enzyme system, and a modified cap nucleotide; and contacting the uncapped RNA with the capping enzyme system and the modified cap nucleotide under conditions wherein modified-nucleotide-capped RNA is synthesized. In other embodiments, the invention provides a kit comprising a capping enzyme system and a modified cap nucleotide.

The invention finds use in research, including clinical research, as well as in commercial and therapeutic applications, particularly with respect to in vitro and in vivo production of RNA and polypeptides, and for capture or isolation of uncapped RNA comprising primary RNA transcripts or RNA having a 5'-diphosphate in a mixed population that also includes other RNA molecules.

During development of embodiments of the present invention, it was determined that vaccinia virus capping enzyme or a poxvirus capping enzyme that has similar enzymatic activities can utilize modified cap nucleotides as substrates to cap uncapped RNA comprising primary RNA transcripts or RNA having a 5'-diphosphate. Thus, in some embodiments, the present invention provides a method for catalyzing formation of a modified-nucleotide-capped RNA comprising the step of contacting an RNA transcript with a capping enzyme system, such as poxvirus capping enzyme, and modified cap nucleotide under conditions permissive to the formation of the modified-nucleotide-capped RNA. In some embodiments of the method, the uncapped RNA comprising primary RNA transcripts or RNA having a 5'-diphosphate is in a biological sample. In some embodiments, the uncapped RNA is mRNA in the biological sample. In some embodiments, the uncapped RNA in the biological sample comprises small primary RNA transcripts that are not mRNA. In some embodiments, the uncapped RNA in the biological sample comprises small nuclear RNA (snRNA), micro RNA (miRNA), or another primary RNA transcript. In some embodiments, the uncapped RNA comprising primary RNA transcripts or RNA having a 5'-diphosphate is synthesized by an RNA polymerase in an in vitro transcription reaction or RNA amplification reaction, or by a replicase in an in vitro replication reaction. In some cases, up to essentially 100% of the uncapped RNA comprising primary RNA transcripts or RNA having a 5'-diphosphate in a population of RNA molecules is capped (e.g., see Examples). Thus, the present invention provides compositions, kits and methods for significantly improving synthesis of capped RNA transcripts (e.g., mRNA). The present invention provides a method, and kits for performing the method, which use a capping enzyme, such as vaccinia capping enzyme or poxvirus capping enzyme, and a modified cap nucleotide to synthesize modified-nucleotide-capped RNA with higher efficiency (e.g., with a capping efficiency approaching 100%) and in higher yields than is obtained by co-transcriptional capping using a dinucleotide cap analog. In some embodiments, the capping efficiency is greater than 80%. In some embodiments, the capping efficiency is greater than 85%. In some embodiments, capping efficiency is greater than 90%. In some embodiments, capping efficiency is greater than 97%. In some embodiments, capping efficiency is greater than of 99%. Thus, the present invention provides compositions, kits and methods for significantly improving synthesis of capped RNA transcripts (e.g., mRNA).

The methods and kits of embodiments of the invention result in a modified-nucleotide-capped RNA with the modified cap nucleotide in the correct orientation. In some embodiments, the method yields novel modified-nucleotide-capped RNA compositions having a cap 0 structure that have improved translational efficiency in vitro and/or in vivo compared to RNA compositions having the same sequence but which are uncapped or which are capped with an unmodified $m^7G$ cap nucleotide. In some embodiments, the method yields novel modified-nucleotide-capped RNA compositions having a cap I structure, which further improves translational efficiency. In some embodiments, the modified nucleotide-capped RNA has a 3' poly(A) tail. In still other embodiments, the method of the invention is used to selectively label uncapped RNA comprising a primary RNA transcript or RNA having a 5'-diphosphate with an affinity tag (e.g., biotin), or with a fluorescent dye or other detectable molecule, thereby permitting selective capture, isolation, detection, quantification and/or assay of the modified-nucleotide-capped RNA molecules in a population of other molecules. In some embodiments of the invention, the method uses the modified-nucleotide-capped RNA, in a population that also comprises other RNA molecules, to selectively capture or isolate the modified-nucleotide-capped RNA without capturing or isolating the RNA molecules that do not comprise a modified cap nucleotide. For example, but without limitation, methods of the invention can be used to isolate prokaryotic mRNA in a mixture of prokaryotic total RNA or in a mixture of prokaryotic and eukaryotic total RNA, such as from a eukaryotic cell infected by a prokaryotic pathogen (e.g., *Mycobacterium*) or from a eukaryotic cell in symbiosis with a prokaryote (e.g., *Rhizobium* in a legume root nodule). The invention further provides kits that use the novel methods of the invention for obtaining modified-nucleotide-capped RNA molecules, including novel compositions of such molecules that have improved in vivo and/or in vitro translational efficiencies or other properties that are useful for other applications described herein. Thus, the invention provides novel methods, kits and compositions with significant benefits and advantages over the prior art for a variety of research, commercial, and therapeutic applications.

Methods and Kits for Capping Uncapped RNA

Embodiments of the present invention provide methods and kits for obtaining a modified-nucleotide-capped RNA and compositions comprising modified-nucleotide-capped RNA molecules not previously known in the art.

In one embodiment, the invention is a kit comprising a capping enzyme system and a modified cap nucleotide. A method of the invention for obtaining modified-nucleotide-capped RNA comprises: (a) providing an uncapped RNA comprising primary RNA transcripts or RNA having a 5'-diphosphate, a capping enzyme system, and a modified cap nucleotide; and contacting the uncapped RNA with the capping enzyme system and the modified cap nucleotide under conditions wherein modified-nucleotide-capped RNA is synthesized.

In some embodiments of the invention, the kit further comprises S-adenosyl-methionine or, in some embodiments, S-adenosyl-ethionine, in view of the finding that 7-ethylguanosine-containing capped RNA synthesized in vitro by reovirus capping enzyme in the presence of S-adenosyl-ethionine was equally active in translation and binding to ribosomes as 7-methylated capped RNA (Furuichi, Y et al., J. Biol. Chem., 254: 6732-6738, 1979). In some embodiments of the method, the method further comprises providing S-adenosyl-methionine or S-adenosyl-ethionine. In some embodiments of the method, the capping enzyme system comprises guanine-7-methyltransferase activity and the uncapped RNA is contacted with the capping enzyme system and the modified cap nucleotide is synthesized in the presence of S-adenosyl-methionine or S-adenosyl-ethionine, whereby the modified-nucleotide-capped RNA synthesized has a methyl group or an ethyl group, respectively, on the N7 position of the guanine in the modified cap nucleotide. In some embodiments of the method, the modified-nucleotide-capped RNA is synthesized in the absence of S-adenosyl-methionine or S-adenosyl-ethionine, wherein the modified cap nucleotide does not have a methyl group on the nitrogen at the 7 position of the guanine.

In some embodiments of the invention, the kit comprising a capping enzyme system, a modified cap nucleotide, and S-adenosyl-methionine further comprises an enzyme having mRNA (nucleoside-2'-O—) methyltransferase activity. In some embodiments of the invention, the method of contacting the uncapped RNA transcript with the capping enzyme system and the modified cap nucleotide under conditions wherein modified-nucleotide-capped RNA is synthesized further comprises the step of contacting the modified-nucleotide-capped RNA with an mRNA (nucleoside-2'-O—) methyltransferase and S-adenosyl-methionine under conditions wherein a modified-nucleotide-capped RNA having a cap I structure (i.e., having a methylated 2'-hydroxyl group in the penultimate nucleotide at the 5-end of the RNA) is obtained. In some embodiments, the step of contacting the primary RNA transcript with the capping enzyme system and the modified cap nucleotide under conditions wherein modified-nucleotide-capped RNA is synthesized and the step of contacting the modified-nucleotide-capped RNA with an mRNA (nucleoside-2'-O—) methyltransferase and S-adenosyl-methionine are carried out concurrently in the same reaction mixture. In some embodiments, the enzyme having mRNA (nucleoside-2'-O—) methyltransferase activity is encoded by poxvirus DNA. In some embodiments, the enzyme having mRNA (nucleoside-2'-O—) methyltransferase activity is encoded by vaccinia virus DNA. In some embodiments, the mRNA (nucleoside-2'-O—) methyltransferase is purified from virions. In other embodiments, the mRNA (nucleoside-2'-O—) methyltransferase is purified from a recombinant source. In some embodiments, the mRNA (nucleoside-2'-O—) methyltransferase is purified from E. coli cells that express the poxvirus gene that is cloned in a plasmid or other vector. In some embodiments, the mRNA (nucleoside-2'-O—) methyltransferase is purified from E. coli cells that express the vaccinia gene that is cloned in a plasmid or other vector. In some embodiments, the enzyme having mRNA (nucleoside-2'-O—) methyltransferase activity is encoded by a yeast or fungal gene. In other embodiments, the enzyme is encoded by a nematode, mammalian or other metazoan gene, whether from a wild-type or recombinant source. The invention is not limited by the particular source of the enzyme, so long as it is active in methylating the 2'-position of the penultimate nucleotide at the 5-end of modified-nucleotide-capped RNA.

In some embodiments, the method further comprises the step of contacting the modified-nucleotide-capped RNA with an mRNA (nucleoside-2'-O—) methyltransferase in the presence of S-adenosyl-methionine under conditions wherein a modified-nucleotide-capped RNA with a cap I structure (i.e., having a methyl group on the 2'-hydroxyl of the penultimate nucleotide at the 5-end) is obtained. In some embodiments of the method, the modified-nucleotide-capped RNA having a cap I structure is synthesized in the presence of the capping enzyme system and the mRNA (nucleoside-2'-O—) methyltransferase in the same reaction mixture. In some embodiments, the enzyme having mRNA (nucleoside-2'-O—) methyltransferase activity is encoded by a poxvirus DNA. In some embodiments, the mRNA (nucleoside-2'-O—) methyltransferase is purified from poxvirus virions, whereas in other embodiments, the mRNA (nucleoside-2'-O—) methyltransferase is purified from a recombinant source, such as, from E. coli cells which express the gene that encodes the enzyme and which is cloned in a plasmid or other vector. In some embodiments, the enzyme having mRNA (nucleoside-2'-O—) methyltransferase activity is encoded by vaccinia virus DNA. In some embodiments, the mRNA (nucleoside-2'-O—) methyltransferase is purified from vaccinia virions, whereas in other embodiments, the mRNA (nucleoside-2'-O—) methyltransferase is purified from a recombinant source, such as from E. coli cells which express the vaccinia gene for the enzyme that is cloned in a plasmid or other vector.

During the course of the investigations related to the development of embodiments of the present invention, we found that an enzyme with mRNA (nucleoside-2'-O—) methyltransferase activity can methylate the 2'-hydroxyl group of the penultimate nucleotide at the 5-end of said 5'-capped RNA, including modified-nucleotide-capped RNA, irrespective of whether the $N^7$-position of the guanine base of the cap nucleotide, including a modified cap nucleotide, is methylated. Therefore, with respect to the present invention, when we refer to "capped RNA having a cap 0 structure", including a "modified-nucleotide-capped RNA having a cap 0 structure", we mean the RNA that results from the addition of the cap nucleotide to the 5'-end of primary RNA by the capping enzyme system, whether or not the cap nucleotide or the modified cap nucleotide has a methyl group on the $N^7$-position of the guanine base, and when we refer to "capped RNA having a cap I structure", including a "modified-nucleotide-capped RNA having a cap I structure", we mean the 5'-capped RNA that has a methyl group on the 2'-hydroxyl group of the penultimate nucleotide at the 5-end of said 5'-capped RNA, in most cases, but not exclusively, by the action of an enzyme with mRNA (nucleoside-2'-O—) methyltransferase activity.

In some embodiments, the kits and methods for synthesizing modified-nucleotide-capped RNA having a cap 0 or cap I structure, with or without a poly(A) tail, and the compositions comprising a modified-nucleotide-capped RNA having a cap 0 or cap I structure, with or without a poly(A) tail, are further used for in vitro or in vivo translation of proteins or polypeptides. For example, some embodiments of the invention comprise kits, methods and compositions, not previously known in the art, that provide modified-nucleotide-capped RNAs that are translated into proteins with equal or higher efficiency in cells in vivo and/or in cell-free extracts in vitro compared to unmodified $m^7G$-capped RNA molecules having the same sequence. In some embodiments in which translation efficiency is equal to unmodified $m^7G$-capped RNA, the modified-nucleotide-capped RNA has benefits in particular applications, cells, or conditions. The present inventors found that some compositions of modified-nucleotide capped RNA synthesized using the methods and kits of the invention were translated in vivo or in vitro with higher efficiency than the same RNA molecules with an unmodified $m^7G$-cap, whether the caps had a cap 0 or a cap I structure (e.g., see Examples). Thus, in some experiments, modified-nucleotide-capped RNA comprising an $N^7$-Me-2'-amino-2'-dG-capped RNA or an $N^7$-Me-$O^6$-Me-G-capped RNA with caps having either a cap 0 or a cap I structure and poly(A) tails on their 3'-termini were translated in vivo or in vitro with higher efficiency than the corresponding RNA molecules with an unmodified $m^7G$-cap. In other experiments wherein a different primary RNA transcript was used to synthesize modified-nucleotide-capped RNA, a different spectrum of modified cap nucleotides (e.g., $O^6$-Me-GTP, 2'-F-2' dGTP, 2'-O-Me-GTP, and 2'-azido-dGTP) resulted in synthesis of modified-nucleotide-capped RNAs that exhibited higher levels of in vivo or in vitro translation (e.g., in some cases, higher than with the corresponding RNA molecules with an unmodified $m^7G$-cap) and the relative translation levels varied with different types of cells or cell-free translation systems.

In other embodiments of the kits and method for synthesizing a modified-nucleotide-capped RNA for in vitro or in vivo translation of proteins or polypeptides, the modified cap nucleotide is 3'-O-methylguanosine-5'-triphosphate or 2'-O-methylguanosine-5'-triphosphate, in which embodiments, the modified-nucleotide-capped RNA synthesized using the kit and method should be the same as the capped RNA obtained in an in vitro transcription reaction using the respective $m_2^{7,3'\text{-}O}$GpppG or $m_2^{7,2'\text{-}O}$GpppG ARCA. The present invention is beneficial because such modified-nucleotide-capped RNA molecules having a modified cap nucleoside with a 3'- or 2'-O-methyl group can be synthesized with higher efficiency and in higher yields using a method or kit of the invention than the molecules synthesized by in vitro transcription reaction using the respective ARCA that have been reported to be translated in vitro and in vivo, with higher efficiency than unmodified $m^7G$-capped RNA. In other embodiments in which the modified cap nucleotide is 3'-deoxyguanosine-5'-triphosphate, the modified-nucleotide-capped RNA obtained using the kit or method of the invention is identical to the capped RNA obtained by in vitro transcription in the presence of the $m^7(3')$dGpppG ARCA, which has also been reported to be translated in vitro with higher efficiency. Thus, the kits and methods of the invention are more desirable in terms of yield, purity, cost and/or time compared to existing techniques for obtaining such capped RNA molecules using a dinucleotide ARCA in an in vitro transcription reaction.

The present inventors also found that capped RNA molecules obtained by in vitro transcription of a DNA template in the presence of a dinucleotide cap analog, such as but not limited to an $m_2^{7,3'-O}$GpppG or $m_2^{7,2'-O}$GpppG ARCA, can be 2'-O-methylated by mRNA (nucleoside-2'-O—) methyltransferase in an in vitro reaction containing S-adenosyl-methionine. Thus, one other embodiment of the present invention is a method for synthesizing a modified-nucleotide-capped RNA with a cap I structure (i.e., having a methylated 2'-hydroxyl group in the penultimate nucleotide at the 5-end), said method comprising: providing a capped RNA molecule having a cap 0 structure that was obtained using a dinucleotide cap analog in an in vitro transcription reaction (e.g., $m_2^{7,3'-O}$G-capped RNA or $m_2^{7,2'-O}$G-capped RNA); and contacting the modified-nucleotide-capped RNA having a cap 0 structure with mRNA (nucleoside-2'-O—) methyltransferase and S-adenosyl-methionine under conditions wherein a modified-nucleotide-capped RNA with a cap I structure is synthesized.

The invention also provides kits and methods for obtaining modified-nucleotide-capped RNA that has a poly(A) tail. This can be beneficial because capped RNA that has a poly (A) tail is more stable and is translated with higher efficiency in vivo, and sometimes in vitro, than the same RNA that lacks a poly(A) tail. Thus, in some embodiments, the kit further comprises poly(A) polymerase. In some embodiments of the invention, the method further comprises the step of contacting the modified-nucleotide-capped RNA, having either a cap 0 or a cap I structure, with poly(A) polymerase and ATP under conditions wherein modified-nucleotide-capped RNA having a poly(A) tail is synthesized. In some embodiments, the length of the poly(A) tail synthesized is about 30 nucleotides. In other embodiments, the length of the poly(A) tail synthesized is about 30 nucleotides to at about 100 nucleotides. In other embodiments, the length of the poly(A) tail synthesized is about 100 nucleotides to at about 200 nucleotides. In still other embodiments, the length of the poly(A) tail synthesized is about 200 nucleotides to about 400 nucleotides. In some embodiments, the length of the poly(A) tail synthesized is greater than 400 nucleotides. In some embodiments wherein the modified-nucleotide-capped RNA is translated in vitro in cell-free extracts, the modified-nucleotide-capped RNA lacks a poly(A) tail. Without limitation, the poly(A) polymerase can be selected from the group consisting of *Escherichia coli* poly(A) polymerase and yeast poly(A) polymerase. In some embodiments the poly(A) polymerase is recombinant poly (A) polymerase encoded by the *E. coli* pcnB gene. Methods for polyadenylating RNA using a poly(A) polymerase are well known in the art and kits for such purpose are commercially available. For example, RNA can be polyadenylated using A-Plus™ poly(A) polymerase tailing kit (EPICENTRE Biotechnologies, Madison, Wis., USA) according to the directions provided with the kit.

In some cases, an uncapped RNA is more difficult to cap if the sequence of nucleotides at the 5'-terminus of the uncapped RNA to be capped is complementary to and anneals with another sequence that is within the same RNA molecule or that is in a second RNA molecule present in the capping enzyme reaction. For example, but without limitation, the uncapped RNA is more difficult or impossible to cap using a capping enzyme system and a cap nucleotide if the sequence at the 5'-terminus of the uncapped RNA anneals to form a stable duplex, such as a hairpin, dimer or another duplex structure that involves at least the 5'-terminal nucleotide. The inventors found certain conditions for carrying out the capping reaction using capping enzyme and a cap nucleotide wherein the efficiency of capping uncapped RNA that forms such a duplex involving the 5'-terminus is increased by at least 25 percent. Without being bound by theory, it is believed that the capping efficiency increases using such conditions because the conditions disrupt or interfere with formation of the duplex involving the 5'-terminus, either by decreasing the melting temperature (Tm) of the duplex, or by competitively binding to nucleotides in close proximity to the 5'-terminus of the uncapped RNA (e.g., within about 3 to about 30 bases of the 5'-terminus of the uncapped RNA). Thus, one embodiment of the present invention is a reaction mixture comprising a component that improves the efficiency of capping uncapped RNA that forms a duplex involving at least the 5'-terminal nucleotide, said reaction mixture comprising a capping enzyme system and a cap nucleotide, and additionally comprising at least one of the following: (i) dimethylglycine (betaine) at, for example, a final concentration of at least 0.5 M; (ii) a single-stranded binding protein at, for example, a concentration of at least 0.1 micrograms per microliter; (iii) an RNA helicase at, for example, a concentration of at least 0.1 micrograms per microliter; (iv) an RNA polymerase at, for example, a concentration of at least 0.1 micrograms per microliter; or (v) a DNA polymerase at, for example, a concentration of at least 0.1 micrograms per microliter, or functionally equivalent components. One embodiment is a kit comprising a capping enzyme system and a cap nucleotide, and additionally comprising at least one of the following: (i) dimethylglycine (betaine); (ii) a single-stranded binding protein; (iii) an RNA helicase; (iv) an RNA polymerase; or (v) a DNA polymerase. One embodiment of a method comprises contacting the uncapped RNA with capping enzyme system and the cap nucleotide in a reaction mixture comprising at least one of the following: (i) dimethylglycine (betaine) at a final concentration of at least 0.5 M; (ii) a single-stranded binding protein at a concentration of at least 0.1 micrograms per microliter; (iii) an RNA helicase at a concentration of at least 0.1 micrograms per microliter; (iv) an RNA polymerase at a concentration of at least 0.1 micrograms per microliter; or (v) a DNA polymerase at a concentration of at least 0.1 micrograms per microliter. The above embodiments of the reaction mixture, the kit, or the method are not limited to use of a modified cap nucleotide. Any cap nucleotide that is a substrate for the capping enzyme system can be used. In some preferred embodiments, the cap nucleotide is a modified cap nucleotide. In some preferred embodiments, the cap nucleotide is GTP. In embodiments of the reaction mixture, kit or method that comprise dimethylglycine (betaine), the compound is used as a zwitterion and is not used as a salt and the final concentration in the reaction mixture can be up to about 5 M. In some embodiments of the reaction mixture, kit or method, the single-stranded binding protein is bacteriophage T4 gene 32 protein or a Thermus single-stranded binding protein; however, the invention also contemplates use of another suitable single-stranded binding protein that binds to nucleotides in close proximity to the 5'-terminus of the uncapped RNA (e.g., within about 3 to about 30 bases of the 5'-terminus of the uncapped RNA). In some embodiments of the reaction mixture, kit or method, the RNA polymerase used is a T7-type RNA polymerase; in some embodiments, it is selected from the group consisting of T7 RNA polymerase, T3 RNA polymerase, and SP6 RNA polymerase. In embodiments of the reaction mixture, kit or method, that comprise DNA polymerase, the DNA polymerase is the large fragment of *Bacillus* DNA polymerase (i.e., equivalent to the enzyme obtained by subtilisin digestion of the DNA polymerase holoenzyme or the clone thereof). In some embodiments of the reaction mixture, kit or method, the component is titrated in the reaction mixture to determine the optimal concentration for capping using the capping enzyme system, the cap nucleotide, and the particular uncapped RNA. In some embodiments, the method additionally comprises the step of heating the uncapped RNA in water at a temperature of at least 10 degrees above the melting temperature (i.e., Tm) of the duplex for at least two minutes and then cooling rapidly on ice, prior to using it in the capping reaction.

Types and Sources of Uncapped RNA

Exemplary types and sources of uncapped RNA useful in the methods and compositions of embodiments of the invention are described below.

In some embodiments, the uncapped RNA is a primary RNA transcript, meaning an RNA having a 5'-triphosphate group from an in vivo or an in vitro source, and the method comprises contacting the primary RNA transcript with the capping enzyme system and the modified cap nucleotide under conditions wherein modified-nucleotide-capped RNA is synthesized. For example, but without limitation, in some embodiments, the primary RNA transcript is uncapped mRNA from a prokaryotic source or the primary RNA transcript is synthesized by in vitro or in vivo transcription of a DNA template using an RNA polymerase, or by in vitro or in vivo replication of an RNA template using a replicase (e.g., Q-beta replicase). In some embodiments, the primary RNA transcript is synthesized in an in vitro transcription reaction using a T7-type RNA polymerase. Without limitation, in some embodiments, the T7-type RNA polymerases that is used to synthesize the primary RNA transcript is selected from the group consisting of T7 RNA polymerase, T3 RNA polymerase and SP6 RNA polymerase. In some embodiments, the primary RNA transcript is obtained from an in vitro transcription reaction that is part of an RNA amplification reaction. In some preferred embodiments, the RNA amplification reaction results in synthesis of sense RNA. In some embodiments, the RNA amplification reaction results in synthesis of anti-sense RNA. The primary RNA transcript can also be pre-miRNA or pre-snRNA from an in vivo source, or any other primary RNA transcript having a 5'-triphosphate from an in vivo or in vitro source.

In some embodiments, the uncapped RNA is RNA having a 5'-diphosphate group rather than a primary RNA transcript having a 5'-triphosphate group, and the method comprises contacting the RNA having a 5'-diphosphate group with the capping enzyme system and the modified cap nucleotide under conditions wherein modified-nucleotide-capped RNA is synthesized. In some embodiments in which uncapped RNA that has a 5'-diphosphate group is used rather than a primary RNA transcript having a 5'-triphosphate group, the capping enzyme system is a capping enzyme system having RNA triphosphatase activity, even though such enzymatic activity is not required. In other embodiments in which the RNA has a 5'-diphosphate group is used, the method comprises use of a capping enzyme system that lacks RNA triphosphatase activity. Thus, whenever a method of the present invention described herein uses a primary RNA transcript to synthesize a modified-nucleotide-capped RNA, it should be understood that the invention also includes the same method in which an RNA having a 5'-diphosphate group is used in place of a primary RNA transcript having a 5'-triphosphate group. In some embodiments, the RNA that has a 5'-diphosphate group is from an in vivo or an in vitro source. The invention is not limited with respect to the source of the RNA that has a 5'-diphosphate. For example, but without limitation, in some embodiments, the RNA that has a 5'-diphosphate is obtained by using a nucleoside-5'-diphosphate ("NDP") to prime in vitro transcription of DNA templates using an RNA polymerase. For example, in one embodiment, the RNA that has a 5'-diphosphate is synthesized using a T7-type RNA polymerase, such as T7, T3 or SP6 RNA polymerase, in an in vitro transcription reaction, except that, instead of using only the four ribonucleoside-5'-triphosphates (i.e., collectively, "NTPs", or individually, "ATP", "CTP", "GTP" and "UTP", each of which is generically referred to as an "NTP") at appropriate concentrations known in the art for such in vitro transcription (e.g., see Method 1), the NTP corresponding to the first-transcribed or initiating nucleotide of the RNA in the reaction is replaced by a mixture of the NDP (i.e., the "nucleoside-5'-diphosphate") and the NTP corresponding to the first-transcribed nucleotide. The ratio of NDP to NTP is set at between about 4-to-1 to about 10-to-1, or, in other embodiments, even to about 20-to-1, or more, in the in vitro transcription reaction mixture so that there is a higher probability that the RNA polymerase initiates transcription by extension of the 3'-OH of the NDP, rather than by extension of the 3'-OH of the NTP. In other embodiments, the RNA that has a 5'-diphosphate is obtained by contacting a primary RNA transcript having a 5'-triphosphate with an RNA triphosphatase under suitable reaction conditions. In other embodiments, the RNA having a 5'-diphosphate is obtained by contacting an RNA having a 5'-cap with a decapping enzyme (e.g., *Saccharomyces cerevisiae* or human decapping enzyme) under suitable reaction conditions. In other embodiments, the RNA that has a 5'-diphosphate is obtained from an in vivo source, i.e., from a biological sample.

In some embodiments, the uncapped RNA comprising primary RNA transcripts or RNA having a 5'-diphosphate group for synthesizing a modified-nucleotide-capped RNA lacks a poly(A) tail on the 3'-terminus, such as is the case for most mRNA molecules from a prokaryotic bacterial source. In some embodiments, the uncapped RNA comprising a primary RNA transcript or RNA that has a 5'-diphosphate group has a poly(A) tail on the 3'-terminus, which uncapped RNA is obtained from an in vivo source, such as an uncapped primary RNA transcript from a eukaryotic cell, or in some cases, which uncapped RNA is obtained from a prokaryotic cell, or from an in vitro source. In some embodiments the primary RNA transcript with the poly(A) tail is obtained by in vitro transcription of a DNA template that encodes the poly(A) tail. In other embodiments, the primary RNA transcript with the poly(A) tail is obtained by in vitro polyadenylation of a primary RNA transcript without a poly(A) tail using ATP and poly(A) polymerase. Thus, in some embodiments, the kit of the invention further comprises poly(A) polymerase. In some embodiments wherein the modified-nucleotide-capped RNA that is synthesized using a method of the invention lacks a poly(A) tail, the method further comprises the step of contacting the modified-nucleotide-capped RNA with poly(A) polymerase and ATP under conditions wherein a modified-nucleotide-capped RNA having a poly(A) tail is synthesized.

In some embodiments of the invention, the uncapped RNA comprising primary RNA transcripts or RNA having a 5'-diphosphate that is used to synthesize modified-nucleotide-capped RNA is from an in vitro transcription reaction or an RNA amplification reaction that produces sense RNA (e.g., but without limitation, by amplification of RNA from one or a small number of cancer cells from a patient). In some embodiments, the RNA amplification reaction used to synthesize the sense RNA comprises the terminal tagging method described in U.S. Patent Application No. 20050153333 of Sooknanan. In preferred embodiments of the invention, the uncapped RNA comprising primary RNA transcripts or RNA having a 5'-diphosphate that is used to synthesize modified-nucleotide-capped RNA is prepared from a biological source by subtractive hybridization, digestion and RNA amplification, whereby the uncapped RNA comprising primary RNA transcripts or RNA having a 5'-diphosphate obtained is "condition-specific", as defined elsewhere herein. In some preferred embodiments, the condition-specific RNA is obtained using the "cap-dependent subtraction" ("CDS") method of the present invention, as described herein. In preferred embodiments, the condition-specific uncapped RNA obtained using the CDS method is further amplified using a sense RNA amplification reaction. Thus, in some embodiments, the uncapped RNA comprising primary RNA transcripts or RNA having a 5'-diphosphate is condition-specific, and the method comprises contacting the condition-specific uncapped RNA comprising primary RNA transcripts or RNA having a 5'-diphosphate with the capping enzyme system and the modified cap nucleotide under conditions wherein condition-specific modified-nucleotide-capped RNA is synthesized. In different embodiments, the condition-specific modified-nucleotide-capped RNA that is synthesized is selected from the group consisting of: cap 0 modified-nucleotide-capped RNA with a poly(A) tail; cap I modified-nucleotide-capped RNA with a poly(A) tail; cap 0 modified-nucleotide-capped RNA lacking a poly(A) tail; and cap I modified-nucleotide-capped RNA lacking a poly(A) tail.

Capping Enzyme System

Embodiments of the present invention utilize a capping enzyme system in methods to synthesize modified-nucleotide-capped RNA, and in kits that also contain a modified cap nucleotide for use in the method. The present invention is not limited by the type of capping enzyme utilized. Indeed, a variety of capping enzymes can be used in the present invention. In some embodiments, the capping enzyme system is purified from cells that express the capping enzymes from genes cloned in one or more recombinant vectors. In some embodiments, the capping enzyme system is purified from a natural source. In some embodiments, the capping enzyme system is a poxvirus capping enzyme system. In some preferred embodiments, the capping enzyme system is vaccinia virus capping enzyme. In some embodiments, the vaccinia virus capping enzyme system is purified from vaccinia virions. In other embodiments, the vaccinia virus capping enzyme system is purified from a recombinant source. In a preferred embodiment, the capping enzyme system used in the method or in a kit of the invention comprises RNA guanyltransferase activity. In one preferred embodiment, the capping enzyme system comprises RNA triphosphatase and RNA guanyltransferase activity. In some preferred embodiments, the capping enzyme system comprises purified RNA guanyltransferase and guanine-7-methyltransferase activities, which activities can be from a native or recombinant source. In some preferred embodiments, the capping enzyme system comprises purified RNA triphosphatase, RNA guanyltransferase, and guanine-7-methyltransferase activities, which activities can be from a native or recombinant source. The capping enzyme system can comprise only one protein having all of these enzyme activities. One such preferred embodiment comprises a poxvirus capping enzyme system. One such preferred embodiment comprises a vaccinia capping enzyme system. Alternatively, the capping enzyme system can comprise two or three different proteins or polypeptides having RNA triphosphatase, RNA guanyltransferase, and guanine-7-methyltransferase activity. Some embodiments of the invention comprise kits or methods, wherein the capping enzyme system used in the kit or method comprises two or three enzymes having RNA triphosphatase, RNA guanyltransferase, and guanine-7-methyltransferase activity, each enzyme can be from the same source or they can be from two or three different sources. For example, but without limitation, in some embodiments, the kits or methods provide a capping enzyme system wherein the polypeptide having RNA triphosphatase activity and/or the polypeptide having guanine-7-methyltransferase activity are from a single source (e.g., from *Saccharomyces cerevisiae*) and the polypeptide having RNA guanyltransferase activity is from another source (e.g., a polypeptide encoded by a poxvirus gene); and in other embodiments, the kits or methods provide a capping enzyme system wherein the polypeptides having each of the three enzymatic activities is from a different natural or recombinant source. If the capping enzyme system comprises two or three different enzymes or polypeptides, the enzymes can be used sequentially or, more preferably, they can be used together in a single reaction mixture. In some embodiments, the capping enzyme system has guanine 7-methyltransferase activity and the method comprises contacting the uncapped RNA with the capping enzyme system in the presence of S-adenosyl-methionine or S-adenosyl-ethionine under conditions wherein the capping enzyme system, including the guanine-7-methyltransferase activity of said capping enzyme system, is active and modified-nucleotide-capped RNA having, respectively, a methyl or an ethyl group on the nitrogen at the 7 position of guanine is synthesized. In some embodiments, the enzyme that has guanine-7-methyltransferase activity is poxvirus guanine-7-methyltransferase. In some embodiments, the enzyme having guanine-7-methyltransferase activity is a component of the vaccinia capping enzyme.

Modified Cap Nucleotides

Exemplary modified cap nucleotides of embodiments of the present invention are described below.

In some preferred embodiments, the modified cap nucleotide used in the method or kit of the invention comprises a modified 2'- or 3'-deoxyguanosine-5'-triphosphate (also called guanine 2'- or 3'-deoxyribonucleoside-5'-triphosphate) wherein the 2'- or 3'-deoxy position of the sugar moiety is substituted with a moiety comprising an amino group, an azido group, a fluorine group, a methoxy group, a thiol (or mercapto) group, or a methylthio (or methylmercapto) group, or wherein the O6 oxygen of the guanine base is replaced by a thiol (or mercapto) group or by a methylthio (or methylmercapto) group. In other preferred embodiments, the modified cap nucleotide comprises modified guanosine-5'-triphosphate (also called guanine ribonucleoside-5'-triphosphate) wherein the N1 nitrogen of the guanine base is modified by being substituted with a methyl group, or wherein the O6 oxygen of the guanine base is modified by being substituted with an alkyl group, or wherein the O6 oxygen of the guanine base is replaced by a thiol (or mercapto) group or by a methylthio (or methylmercapto) group. In one preferred embodiment, the alkyl group on the O6 oxygen of the guanine base of the modified guanosine-5'-triphosphate is a methyl group. In other embodiments of the method or the kit, the modified cap nucleotide is 3'-deoxyguanosine-5'-triphosphate.

In some embodiments, the kit or method comprises a capping enzyme system and a modified cap nucleotide, wherein the modified cap nucleotide comprises a modified guanine nucleoside-5'-triphosphate selected from the group consisting of: 2'-O-methylguanosine-5'-triphosphate (or guanine 2'-O-methyl-ribonucleoside-5'-triphosphate, or 2'-O-methyl-GTP, or 2'-O-Me-GTP); 3'-O-methylguanosine-5'-triphosphate (or guanine 3'-O-methyl-ribonucleoside-5'-triphosphate, or 3'-O-methyl-GTP or 3'-O-Me-GTP); 2'-amino-2'-deoxyguanosine-5'-triphosphate (or guanine 2'-amino-2'-deoxyribonucleoside-5'-triphosphate, or 2'-NH$_2$-2'-dGTP or 2'-amino-2'-dGTP); 3'-amino-3'-deoxyguanosine-5'-triphosphate (or guanine 3'-amino-3'-deoxyribonucleoside-5'-triphosphate, or 3'-NH₂-3'-dGTP or 3'-amino-3'-dGTP); 2'-azido-2'-deoxyguanosine-5'-triphosphate (or guanine 2'-azido-2'-deoxyribonucleoside-5'-triphosphate, or 2'-N₃-dGTP, or 2'-azido-2'-dGTP); 3'-azido-3'-deoxyguanosine-5'-triphosphate (or guanine 3'-azido-3'-deoxyribonucleoside-5'-triphosphate, or 3'-N₃-dGTP, or 3'-azido-3'-dGTP); 2'-fluoro-2'-deoxyguanosine-5'-triphosphate (or guanine 2'-fluoro-2'-deoxyribonucleoside-5'-triphosphate, or 2'-fluoro-2'-dGTP, or 2'-F-2'-dGTP); 3'-fluoro-3'-deoxyguanosine-5'-triphosphate (or guanine 3'-fluoro-3'-deoxyribonucleoside-5'-triphosphate, or 3'-fluoro-3'-dGTP or 3'-F-3'-dGTP); 2'-mercapto-2'-deoxyguanosine-5'-triphosphate (or guanine 2'-mercapto-2'-deoxyribonucleoside-5'-triphosphate or 2'-mercapto-2'-dGTP or 2'-SH-2'-dGTP); 3'-mercapto-3'-deoxyguanosine-5'-triphosphate (or guanine 3'-mercapto-3'-deoxyribonucleoside-5'-triphosphate or 3'-mercapto-3'-dGTP or 3'-SH-3'-dGTP); 2'-amino-2',3'-dideoxyguanosine-5'-triphosphate (or guanine-2'-amino-2',3'-dideoxyribonucleic acid-5'-triphosphate, or 2'-amino-2',3'-ddGTP); 3'-amino-2',3'-dideoxyguanosine-5'-triphosphate (or guanine-3'-amino-2',3'-dideoxyribonucleic acid-5'-triphosphate, or 3'-amino-2',3'-ddGTP); 2'-azido-2',3'-dideoxyguanosine-5'-triphosphate (or guanine-2'-azido-2',3'-dideoxyribonucleic acid-5'-triphosphate, or 2'-azido-2',3'-ddGTP); 3'-azido-2',3'-dideoxyguanosine-5'-triphosphate (or guanine-3'-azido-2',3'-dideoxyribonucleic acid-5'-triphosphate, or 3'-azido-2',3'-ddGTP); 2'-mercapto-2',3'-dideoxyguanosine-5'-triphosphate (or guanine-2'-mercapto-2',3'-dideoxyribonucleic acid-5'-triphosphate, or 2'-mercapto-2',3'-ddGTP, or 2'-SH-2',3'-ddGTP); and 3'-mercapto-2',3'-dideoxyguanosine-5'-triphosphate (or guanine-3'-mercapto-2',3'-dideoxyribonucleic acid-5'-triphosphate, or 3'-mercapto-2',3'-ddGTP or 3'-SH-2',3'-ddGTP).

In other embodiments, wherein the modified cap nucleotide comprises a modified guanine nucleoside-5'-triphosphate in which the guanine base is modified, the modified cap nucleotide is selected from the group consisting of: $N^1$-methylguanosine-5'-triphosphate (or $N^1$-methylguanine ribonucleoside-5'-triphosphate or $N^1$-methyl-GTP or $N^1$-Me-GTP); $O^6$-methylguanosine-5'-triphosphate (or $O^6$-methylguanine ribonucleoside-5'-triphosphate or $O^6$-methyl-GTP or $O^6$-Me-GTP); 6-thioguanosine-5'-triphosphate (or 6-mercapto-guanosine-5'-triphosphate, or 6-thioguanine ribonucleoside-5'-triphosphate, or 6-mercaptoguanine ribonucleoside-5'-triphosphate, or 6-thio-GTP, or 6-SH-GTP); 6-methylthioguanosine-5'-triphosphate (or 6-methylmercapto-guanosine-5'-triphosphate, or 6-methylthioguanine ribonucleoside-5'-triphosphate, or 6-methylmercaptoguanine ribonucleoside-5'-triphosphate, or 6-methylthio-GTP, or 6-methylmercapto-GTP, or 6-CH₃S-GTP); 6-thio-2'-deoxyguanosine-5'-triphosphate (or 6-thioguanine-2'-deoxyribonucleic acid-5'-triphosphate, or 6-thio-2'-dGTP); 6-thio-3'-deoxyguanosine-5'-triphosphate (or 6-thioguanine-3'-deoxyribonucleic acid-5'-triphosphate, or 6-thio-3'-dGTP); 6-methylthio-2'-deoxyguanosine-5'-triphosphate (or 6-methylthioguanine-2'-deoxyribonucleic acid-5'-triphosphate, or 6-methylthio-2'-dGTP); and 6-methylthio-3'-deoxyguanosine-5'-triphosphate (or 6-methylthioguanine-3'-deoxyribonucleic acid-5'-triphosphate, or 6-methylthio-3'-dGTP).

In still other embodiments of the kit or the method, the modified cap nucleotide is 3'-deoxyguanosine-5'-triphosphate (or guanine 3'-deoxyribonucleoside-5'-triphosphate, or 3'-dGTP), but not 2'-deoxyguanosine-5'-triphosphate (or guanine 2'-deoxyribonucleoside-5'-triphosphate, or dGTP or 2'-dGTP).

The invention is not limited to use of the modified cap nucleotides comprising a modified sugar moiety or a modified base described above. The modified cap nucleotide that is used for the method can comprise any modified guanine nucleoside-5'-triphosphate that is compatible with the enzymatic activities of the capping enzyme systems used in the method.

Modified-Nucleotide-Capped RNA Compositions

The present invention also comprises compositions comprising the modified-nucleotide-capped RNA made using kits and methods of the present invention. For example, composition are provided that are made using a kit comprising a capping enzyme and a modified cap nucleotide or a composition made using the method comprising contacting an uncapped RNA comprising a primary RNA transcript or an RNA having a 5'-diphosphate with a modified cap nucleotide and a capping enzyme system, wherein a modified-nucleotide-capped RNA is synthesized. Thus, the present invention includes new compositions of modified-nucleotide-capped RNA not previously known in the art.

Without limitation, the invention comprises a composition of a modified-nucleotide-capped RNA synthesized using a capping enzyme system and a modified cap nucleotide, wherein said modified-nucleotide-capped RNA is synthesized using a modified cap nucleotide comprising a modified 2'- and/or 3'-deoxyguanosine-5'-triphosphate: wherein the respective 2'- or 3'-deoxy position of the sugar moiety is substituted with a moiety comprising an amino group, an azido group, a fluorine group, a thiol (or mercapto) group or a methylthio (or methylmercapto) group, or wherein the O6-oxygen of the guanine base is replaced by a thiol group or by a methylthio group. In other preferred embodiments, the invention comprises a composition of a modified-nucleotide-capped RNA synthesized using a capping enzyme system and a modified cap nucleotide, wherein said modified-nucleotide-capped RNA is synthesized using a modified cap nucleotide comprising a modified guanosine-5'-triphosphate wherein the N1 nitrogen of the guanine base is modified by being substituted with a methyl group or the O6 oxygen of the guanine base is modified by being substituted with an alkyl group (e.g., a methyl group) or the O6 oxygen of the guanine base is replaced by a thiol group or by a methylthio group. In still other embodiments, the invention comprises any of the above compositions of a modified-nucleotide-capped RNA, wherein the modified-nucleotide-capped RNA composition additionally comprises a 2'-O-methyl group on the 5'-penultimate nucleotide, a poly(A) tail on the 3'-terminus, or both a 2'-O-methyl group on the 5'-penultimate nucleotide and a poly(A) tail on the 3'-terminus. The invention also comprises compositions of modified-nucleotide-capped RNA that have a 2'-O-methyl group on the 5'-penultimate nucleotide or both a 2'-O-methyl group on the 5'-penultimate nucleotide and a poly(A) tail on the 3'-terminus wherein said modified-nucleotide-capped RNA is synthesized using a modified cap nucleotide selected from among: (i) 2'-deoxyguanosine-5'-triphosphate; (ii) 3'-deoxyguanosine-5'-triphosphate; and (iii) 2'- or 3'-deoxyguanosine-5'-triphosphate wherein the respective 2'- or 3'-deoxy position is substituted with a methoxy group.

In still other embodiments, the composition comprises a modified-nucleotide-capped RNA wherein the modified cap nucleotide has an amino or an azido group on the 2'- or 3'-position of the sugar or a thiol group in place of the O6-oxygen of the guanine base and said amino, azido, or thiol group is chemically joined to an affinity tag molecule. In other embodiments, the composition of modified-nucleotide-capped RNA that comprises the affinity tag additionally comprises: (i) a 2'-O-methyl group on the 5'-penultimate nucleotide; (ii) a poly(A) tail on the 3'-terminus; or (iii) both a 2'-O-methyl group on the 5'-penultimate nucleotide and a poly(A) tail on the 3'-terminus. In some preferred embodiments, wherein the modified-nucleotide-capped RNA comprises an affinity tag, the composition additionally comprises an affinity-tag-binding molecule that is bound to the affinity tag. Still further, the invention also comprises embodiments of the modified-nucleotide-capped RNA that is bound through the affinity tag to an affinity-tag-binding molecule, whether said affinity-tag-binding molecule is free or attached to a surface. In some preferred embodiments of any of the above compositions comprising an affinity tag molecule, the affinity tag molecule comprises biotin. In some embodiments of any of the above compositions wherein the composition additionally comprises an affinity-tag-binding molecule that is bound to the affinity tag, the affinity-tag-binding molecule is avidin or streptavidin.

In still other embodiments, the composition comprises a modified-nucleotide-capped RNA wherein the modified cap nucleotide has an amino or an azido group on the 2'- or 3'-position of the sugar or a thiol group in place of the O6-oxygen of the guanine base and said amino, azido, or thiol group is chemically joined to a detectable dye (e.g., a fluorescein dye, an alexa dye, a Cy dye, or another dye known in the art) or to a detectable protein, such as, but not limited to, a phycobiliprotein. In other embodiments, the composition of modified-nucleotide-capped RNA that comprises the detectable dye molecule additionally comprises: (i) a 2'-O-methyl group on the 5'-penultimate nucleotide; (ii) a poly(A) tail on the 3'-terminus; or (iii) both a 2'-O-methyl group on the 5'-penultimate nucleotide and a poly(A) tail on the 3'-terminus. In different embodiments of any of the above compositions, the detectable dye or detectable protein can comprise any detectable moiety for such purpose that is known in the art, including, but not limited to, a detectable dyes described in "Handbook of Fluorescent Probes and Research Products", Ninth Edition, by R. P. Hoagland, Molecular Probes, Inc.

The compositions comprising a modified-nucleotide-capped RNA can be used for a variety of applications. For example, but without limitation, a modified-nucleotide-capped RNA can be used as a substrate for in vivo translation, except in cases such as that of a modified-nucleotide-capped RNA comprising an $N^1$-methylguanosine modified cap nucleotide, which is translated poorly or not at all. Therefore, a modified-nucleotide-capped RNA having $N^1$-methylguanosine in the modified cap nucleotide provides a negative control for studies involving in vitro or in vivo translation. Thus, the invention also includes a composition comprising a modified-nucleotide-capped RNA having an $N^1$-methylguanosine in the modified cap nucleotide.

The inventors found that modified-nucleotide-capped RNA comprising the $N^1$-methylguanosine modified cap nucleoside is not methylated by the guanine-7-methyltransferase activity of the capping enzyme system. However, in general, modified-nucleotide-capped RNA comprising other modified cap nucleotides are N7-methylated by the capping enzyme system in the presence of S-adenosyl-methionine. Thus, the invention comprises compositions of modified-nucleotide-capped RNA comprising an N7-methyl group on the modified cap nucleotide, as well as compositions of modified-nucleotide-capped RNA that lack the N7-methyl group (e.g., if the synthesis is carried out in the absence of S-adenosyl-methionine). In some embodiments, the capping reaction is carried out in the presence of S-adenosyl-methionine, in which embodiments, the invention comprises compositions of modified-nucleotide-capped RNA comprising an N7-ethyl group on the modified cap nucleotide. Thus, by way of example, but not of limitation, in some embodiments, the invention comprises novel compositions of a modified-nucleotide-capped RNA with any of the following modified cap nucleosides: $N^1$-methylguanosine; $O^6$-methylguanosine; $N^7$-methyl-$O^6$-methylguanosine (or $N^7,O^6$-dimethylguanosine); 2'-O-methylguanosine; 3'-O-methylguanosine; 2'-amino-2'-deoxyguanosine; $N^7$-methyl-2'-amino-2'-deoxyguanosine; 3'-amino-3'-deoxyguanosine; $N^7$-methyl-3'-amino-3'-deoxyguanosine; 2'-azido-2'-deoxyguanosine; $N^7$-methyl-2'-azido-2'-deoxyguanosine; 3'-azido-3'-deoxyguanosine; $N^7$-methyl-3'-azido-3'-deoxyguanosine; 2'-fluoro-2'-deoxyguanosine; $N^7$-methyl-2'-fluoro-2'-deoxyguanosine; 3'-fluoro-3'-deoxyguanosine; $N^7$-methyl-3'-fluoro-3'-deoxyguanosine; and 3'-deoxyguanosine. In other embodiments, the invention comprises a modified-nucleotide-capped RNA composition, including any of the compositions listed above, that additionally has a methyl group on the 2'-hydroxyl group of the penultimate ribonucleotide at the 5-end (i.e., has a cap I structure). The present invention further comprises a novel composition of a modified-nucleotide-capped RNA having a cap I structure, wherein the modified-nucleotide-capped RNA having a cap I structure has a modified cap nucleoside selected from the group consisting of: $N^7$-methyl-2'-O-methylguanosine; $N^7$-methyl-3'-O-methylguanosine; $N^7$-methyl-2'-deoxyguanosine; and $N^7$-methyl-3'-deoxyguanosine, wherein the 2'-hydroxyl of the 5'-penultimate nucleotide is also methylated. In still other embodiments, the invention comprises any and all of the modified-nucleotide-capped RNA compositions above having either a cap 0 or a cap I structure, wherein the modified-nucleotide-capped RNA additionally has a poly(A) tail on the 3' terminus.

Methods and Kits for Using Modified-Nucleotide-Capped RNA for In Vitro and In Vivo Translation In some embodiments, the present invention provides methods that comprise the step of translating the modified-nucleotide-capped RNA having either a cap 0 or a cap I structure into protein. Although an understanding of the mechanism is not necessary to practice the present invention and the present invention is not limited to any particular mechanism of action, in some embodiments, compositions and methods of the present invention produce modified-nucleotide-capped RNA (e.g., mRNA) that is translated more efficiently in vitro or in vivo due to the efficiency at which the capping enzyme system is able to cap uncapped RNA comprising primary RNA transcripts or RNA having a 5'-diphosphate, and/or because of the characteristics of the modified-nucleotide-capped RNA to serve as a substrate for translation.

In preferred embodiments, the modified-nucleotide-capped RNA that is used for translation has either a cap 0 or a cap I structure and is polyadenylated. However, since the presence and length of a 3'-poly(A) tail has a greater effect on in vivo translation of modified-nucleotide-capped RNA in a eukaryotic cell than on in vitro translation of the modified-nucleotide-capped RNA in cell-free extracts, the poly(A) tail length varies in different embodiments. In some embodiments, the poly(A) tail has a length of about 30 nucleotides. In other embodiments, the poly(A) tail has a length of about 30 nucleotides to at about 100 nucleotides. In other embodiments, the poly(A) tail has a length of about 100 nucleotides to at about 200 nucleotides. In still other embodiments, the poly(A) tail has a length of about 200 nucleotides to about 400 nucleotides. In some embodiments, the poly(A) tail has a length of greater than 400 nucleotides. In some embodiments wherein the modified-nucleotide-capped RNA is translated in vitro in cell-free extracts, the modified-nucleotide-capped RNA lacks a poly(A) tail.

In some embodiments, the kits and methods use a modified cap nucleotide to synthesize a modified-nucleotide-capped RNA with improved in vitro or in vivo translation properties compared to capped RNA comprising the same sequence but which is uncapped or which comprises the $N^7$-methyl-G cap nucleotide. For example, but without limitation, in some embodiments, the method or kit uses $O^6$-Me-GTP to synthesize modified-nucleotide-capped RNA that results in improved translation, especially in vivo. In other embodiments, a method or kit of the invention uses another modified cap nucleotide that results in levels of in vitro or in vivo translation which are either similar to or higher than what is obtained with capped RNA comprising the standard $N^7$-methyl-G cap nucleotide, in some cases, depending on the cell and other factors. In some embodiments, the modified cap nucleotide provides other benefits in addition to being translated efficiently, such as a method to capture or label the modified-nucleotide-capped RNA (e.g., using a modified cap nucleotide that comprises an amino, azido, or thiol group).

Thus, in some embodiments, compositions and methods of the present invention are used for synthesis of a modified-nucleotide-capped RNA for use in in vitro translation reactions, or for in vivo translation following transformation or transfection of eukaryotic cells with the modified-nucleotide-capped RNA.

In some embodiments, compositions and methods of the present invention produce modified-nucleotide-capped RNA for use in in vitro splicing reactions (e.g., see, Konarska et al., Cell 38: 731-736, 1984; Edery et al., Proc. Natl. Acad. Sci. USA 82: 7590-7594, 1985). In some embodiments, the modified-nucleotide-capped RNAs of the present invention are used for functional studies of heterogeneous nuclear RNAs and viral RNAs.

Cell-Free In Vitro Translation of Modified-Nucleotide-Capped RNA

In some embodiments, the invention provides methods for improved cell-free production of proteins or polypeptides for a variety of applications. Without limitation, in some embodiments, cell-free translation of modified-nucleotide-capped RNA is used to produce proteins or polypeptides for industrial use (e.g., as enzymes for use for food processing or in cleaning products, such as laundry cleaning products), for use for pharmaceutical bioprocessing, for use for molecular diagnostic enzymes, or for therapeutic use (e.g., for use in vaccines that are administered directly to a patient by intradermal injection or another suitable route, or for use in loading an antigen-presenting cell (APC), such as a dendritic cell, with the polypeptide).

In some embodiments of the invention, a kit for translating modified-nucleotide-capped RNA, besides comprising a capping enzyme system and a modified cap nucleotide, additionally comprises an in vitro translation system. Also, one embodiment of the method of the invention further comprises the step of incubating the modified-nucleotide-capped RNA having either a cap 0 or a cap I structure in an in vitro translation system under conditions wherein protein encoded by the modified-nucleotide-capped RNA is obtained. In some embodiments of the kit or method, the in vitro translation system comprises a cell-free extract selected from the group consisting of a plant, an animal, and a yeast or fungal cell-free extract. In some embodiments of the kit or method, the cell-free extract is selected from the group consisting of a wheat germ lysate, a rabbit reticulocyte lysate, a *drosophila* embryo lysate, and a human reticulocyte lysate, wherein the human reticulocytes are derived from human stem cells in culture. In some embodiments, the human reticulocytes are prepared from embryonic stem cells. In other embodiments, the human reticulocytes are prepared from adult stem cells from a patient with a condition. In other embodiments, the human reticulocytes are prepared from adult stem cells from a donor.

The present invention further provides a method for coupled formation of modified-nucleotide-capped RNA and translation of the modified-nucleotide-capped RNA in a cell-free extract. For example, in some embodiments, this coupled formation comprises: (a) contacting an uncapped RNA comprising a primary RNA transcript or RNA having a 5'-diphosphate with a modified cap nucleotide and a capping enzyme system, such as a poxvirus capping enzyme, under conditions permissive to the formation of modified-nucleotide-capped RNA, thereby forming a modified-nucleotide-capped RNA transcript; and (b) incubating the modified-nucleotide-capped RNA transcript formed in step (a) with a cell-free extract under conditions permissive for protein translation.

In some embodiments, the present invention provides a method for coupling catalyzed formation of modified-nucleotide-capped RNA and translation of the modified-nucleotide-capped RNA in a cell-free extract comprising: (a) contacting an uncapped RNA comprising a primary RNA transcript or RNA having a 5'-diphosphate with a capping enzyme system and modified cap nucleotide under conditions wherein a modified-nucleotide-capped RNA is formed; and (b) incubating the modified-nucleotide-capped RNA formed in step (a) with a cell-free extract under conditions such that protein translation of the modified-nucleotide-capped RNA occurs.

In some embodiments, the present invention provides a method for sequentially coupling RNA transcription and catalyzed formation of a modified-nucleotide-capped RNA and translation of the modified-nucleotide-capped RNA in a cell-free extract comprising: (a) contacting a DNA template with RNA polymerase in a reaction buffer under conditions such that an uncapped RNA transcript is formed; (b) contacting the RNA transcript with a capping enzyme system and modified cap nucleotide under conditions wherein a modified-nucleotide-capped RNA is formed; and (c) incubating the modified-nucleotide-capped RNA formed in step (b) with a cell-free extract under conditions wherein protein translation of the modified-nucleotide-capped RNA occurs.

Methods and Kits for Using Polypeptides Obtained by In Vitro Translation of Modified-Nucleotide-Capped RNA for Making Vaccines or Immunotherapeutic Products In some embodiments, the present invention provides methods that comprise using the polypeptide obtained from cell-free translation of modified-nucleotide-capped RNA to make vaccine for a human or animal patient in order to prevent or treat a condition. In some embodiments in which the modified-nucleotide-capped RNA obtained from capping of uncapped RNA comprising a primary RNA transcript or RNA having a 5'-diphosphate using a capping enzyme system and a modified cap nucleotide is translated in vitro, the method further comprises the step of using the polypeptides obtained as antigens for loading of an antigen-presenting cell (APC), such as a dendritic cell, a macrophage, an epithelial cell, or an artificially generated APC from a human or an animal, thereby producing a "polypeptide-loaded" (or an "antigen-loaded") APC that presents on its surface antigenic epitopes encoded by the modified-nucleotide-capped RNA, wherein the epitope is capable of inducing T cell proliferation. Thus, in some embodiments, the method additionally comprises the step of contacting the polypeptide obtained from cell-free translation of modified-nucleotide-capped RNA with an APC, selected from the group consisting of a dendritic cell, a macrophage, an epithelial cell, and an artificially generated APC, whereby a polypeptide-loaded APC is obtained. Thus, the invention also comprises a method for producing a polypeptide-loaded antigen presenting cell (APC), said method further comprising introducing the polypeptides obtained from in vitro translation of polyadenylated modified-nucleotide-capped RNA into or in contact with an APC, thereby producing a polypeptide-loaded APC. In some embodiments, the method further comprises using the polypeptide-loaded APC to make a vaccine to prevent a condition or as an immunotherapy to treat a condition in a human or animal patient.

In some embodiments the modified-nucleotide-capped RNA used for in vitro translation and for loading the APC is derived from a biological specimen from the patient with the condition (e.g., from the tumor of the patient who has the tumor). In some embodiments, the modified-nucleotide-capped RNA used for in vitro translation is derived from a biological specimen from another person with the condition, such as from a tumor of a donor. In some embodiments, the modified-nucleotide-capped RNA used for in vitro translation is prepared from uncapped RNA comprising primary RNA transcripts or RNA having a 5'-diphosphate that is obtained following fractionation by subtractive hybridization and RNA amplification. In some embodiments of the method, the uncapped RNA comprising a primary RNA transcript or RNA having a 5'-diphosphate that is used to obtain the modified-nucleotide-capped RNA for in vitro translation is from an in vitro transcription reaction or an RNA amplification reaction that produces sense RNA (e.g., but without limitation, by amplification of RNA from one or a small number of cancer cells from a patient). In preferred embodiments of the invention, the modified-nucleotide-capped RNA is prepared from uncapped RNA comprising primary RNA transcripts or RNA having a 5'-diphosphate that is obtained following fractionation of RNA from a biological source by subtractive hybridization and digestion, whereby the uncapped RNA is condition-specific. In a preferred embodiment, the subtractive hybridization and digestion method used is the cap-dependent subtraction method of the present invention. In some embodiments, the condition-specific RNA is further amplified using a sense RNA amplification reaction.

The invention also comprises kits for making such polypeptide-loaded (or antigen-loaded) APC, including the cells used therefor. By way of example, but without limitation, the kit can comprise media and reagents for incubating the APC with the polypeptides and growing the cells. In some embodiments, the kit additionally comprises one or more adjuvants or other compositions for enhancing or modulating the immune response.

The invention also includes compositions comprising the polypeptide-loaded (or antigen-loaded) APCs, as well as kits that additionally comprise such polypeptide-loaded (or antigen-loaded) APCs, and which may also contain one or more adjuvants or other compositions for enhancing or modulating the immune response. Thus, the present invention comprises an APC that is loaded with an antigenic polypeptide obtained by in vitro translation of a modified-nucleotide-capped RNA having a cap 0 or a cap I structure, either with or without a poly(A) tail, and which APC is capable of producing antigenic epitopes encoded by said modified-nucleotide-capped RNA on its surface. The APC is selected from the group consisting of a dendritic cell, a macrophage, an epithelial cell, or an artificially generated APC from a human or an animal. In some embodiments, the APC is from the patient with the condition. In some embodiments, the APC is from a donor who is not the patient. The invention further provides a method for treating or preventing a condition, such as a cancer condition or a pathogen-induced condition, said method comprising administering to the patient a therapeutically effective amount of the polypeptide-loaded APC, which polypeptide is obtained by in vitro translation of said modified-nucleotide-capped RNA derived from one or more primary RNA transcripts of cells having said condition.

The invention also provides a method for producing a cytotoxic T lymphocyte (CTL), said method comprising: providing a T lymphocyte; contacting said T lymphocyte in vitro with the polypeptide-loaded APC comprising the polypeptide obtained by in vitro translation of the modified-nucleotide-capped RNA; and maintaining said T lymphocyte under conditions conducive to CTL proliferation, thereby producing a CTL. Thus, one embodiment of the invention is a composition comprising a CTL obtained by contacting the T lymphocyte with the polypeptide-loaded APC comprising the polypeptide obtained by in vitro translation of the modified-nucleotide-capped RNA, and maintaining said T lymphocyte under conditions conducive to CTL proliferation. In some embodiments, the T lymphocyte is derived from the patient with the condition. In some embodiments, the T lymphocyte is derived from a donor. The invention also includes the CTL produced according to this method. The invention further provides a method for treating or preventing a condition, such as tumor formation or a pathogen infection, in a patient, said method comprising administering to the patient a therapeutically effective amount of the CTL obtained using this method.

In some embodiments in which the modified-nucleotide-capped RNA is translated in vitro, the method further comprises using the polypeptides obtained as antigens to make a vaccine for administration directly to a human or animal patient. In some embodiments, the invention comprises a composition comprising the polypeptides obtained by in vitro translation of the modified-nucleotide-capped RNA. The composition comprising the polypeptides can also comprise other compositions, such as adjuvants or other compositions, in order to enhance or modulate the antigenic and/or therapeutic effect. The composition comprising the polypeptides can be formulated for administration by any route commonly used in the art, such as but not limited to, a formulation for intradermal injection, subcutaneous injection, intravenous injection, transdermal application (e.g., using a "patch"), for use as a nasal spray or for use by another route that is determined to be effective for the particular composition. In some embodiments, the modified-nucleotide-capped RNA for in vitro translation is prepared from uncapped RNA derived from primary RNA transcripts from a patient with a condition, such as a cancer or an infection with a bacterial, viral or fungal pathogen. Thus, these compositions can be used for administering the in vitro-synthesized polypeptides to a human or animal patient as a vaccine or immunotherapy in order to prevent or treat a condition.

In Vivo Translation of Modified-Nucleotide-Capped RNA

In still other embodiments the present invention provides methods wherein the modified-nucleotide-capped RNA obtained from capping of uncapped RNA comprising primary RNA transcripts or RNA having a 5'-diphosphate is translated into protein using a capping enzyme system and a modified cap nucleotide. In some embodiments, the method comprises the step of transforming a living eukaryotic cell with the modified-nucleotide-capped RNA, under conditions whereby translation or expression of protein encoded by the modified-nucleotide-capped RNA occurs in the eukaryotic cell in vivo.

In some embodiments the uncapped RNA comprising primary RNA transcripts or RNA having a 5'-phosphate that is used to synthesize the modified-nucleotide-capped RNA for transforming the eukaryotic cells is derived from a biological specimen. In some preferred embodiments, the uncapped RNA that is used to synthesize the modified-nucleotide-capped RNA for transforming the eukaryotic cells comprises prokaryotic (i.e., bacterial) mRNA. In some embodiments, the uncapped RNA that is used to synthesize the modified-nucleotide-capped RNA for transforming the eukaryotic cells is from a biological specimen from a human or animal patient with a condition (e.g., from the tumor of the patient who has the tumor or from a nematode, or bacterial, viral or fungal pathogen, or from a eukaryotic cell, tissue, organ or organism infected with the pathogen). In some embodiments, the uncapped RNA that is used to synthesize the modified-nucleotide-capped RNA for transforming the eukaryotic cells is from a biological specimen from another human or animal patient with the condition, such as from a tumor of a donor. In some embodiments, the modified-nucleotide-capped RNA used for transforming the eukaryotic cells is synthesized from uncapped RNA comprising primary RNA transcripts or RNA having a 5'-diphosphate that is obtained following fractionation by subtractive hybridization and RNA amplification. In some embodiments of the method, the uncapped RNA comprising a primary RNA transcript or RNA having a 5'-diphosphate that is used to synthesize the modified-nucleotide-capped RNA for transforming the eukaryotic cells is from an in vitro transcription reaction or an RNA amplification reaction. For example, but without limitation, in some embodiments the uncapped RNA is synthesized by amplification of mRNA from one or a small number of cancer cells from a patient. In preferred embodiments of the invention, the modified-nucleotide-capped RNA for transforming the eukaryotic cells is synthesized from uncapped RNA comprising primary RNA transcripts obtained following fractionation of RNA from a biological source by subtractive hybridization and digestion, whereby the uncapped RNA is condition-specific. In a preferred embodiment, the subtractive hybridization and digestion method used is the cap-dependent subtraction method of the present invention, described herein. In some embodiments, the condition-specific RNA is further amplified using a sense RNA amplification reaction.

Without limiting the invention, the eukaryotic cell is selected from the group consisting of a dendritic cell, a macrophage, an epithelial cell, an artificially generated APC from a human or an animal, an oocyte (e.g., a *Xenopus* oocyte), a somatic cell of any type from a human, an animal (e.g., a Chinese hamster ovary cell), a plant, and a fungus, provided that a transformation, transfection, or cell fusion system is known or can be developed for introducing the modified-nucleotide-capped RNA into the cell. In some preferred embodiments, the eukaryotic cell is a dendritic cell from a human or an animal. In some embodiments, the step of transforming the eukaryotic cells comprises microinjection (e.g., into oocytes), transfection, lipofection, electroporation, in vivo transposition with a transposome complex, or transformation of the eukaryotic cells by another means known in the art.

In some embodiments of this aspect of the invention, the modified-nucleotide-capped RNA has a cap 0 structure. In some preferred embodiments, the modified-nucleotide-capped RNA has a cap I structure. In some preferred embodiments, the modified-nucleotide-capped RNA having either a cap 0 or a cap I structure has a poly(A) tail on the 3'-terminus. In some preferred embodiments, the modified-nucleotide-capped RNA used to transform or transfect the eukaryotic cell has a poly(A) tail on the 3'-terminus and a 2'-O-methyl group on the 5'-penultimate nucleotide (i.e., the cap of the modified-nucleotide-capped RNA has a cap I structure). In some embodiments, the modified-nucleotide-capped RNA that is used to transform or transfect the eukaryotic cell comprises uncapped RNA that has been capped with a capping enzyme system using a modified cap nucleotide, including but not limited to a modified cap nucleotide selected from the group consisting of: $O^6$-Me-GTP; 2'-amino-2'-dGTP; 2'-azido-2'-dGTP; 2'-fluoro-2'-dGTP; 2'-OMe-GTP; 3'-amino-3'-dGTP; 3'-azido-3'-dGTP; 3'-fluoro-3'-dGTP; 3'-OMe-GTP; and 3'-dGTP. In some embodiments wherein the modified-nucleotide-capped RNA comprises a poly(A) tail or a cap I structure, the modified-nucleotide-capped RNA is synthesized using a capping enzyme system and 2'-dGTP as the modified cap nucleotide. In one embodiment, the modified-nucleotide-capped RNA has an $N^7$-methyl-$O^6$-methylguanosine modified cap nucleoside, which was found in some experiments to provide higher in vivo translation efficiency than the same RNA with an unmodified $m^7G$ cap nucleotide. In other embodiments, the modified-nucleotide-capped RNA has a different modified cap nucleotide.

Methods and Kits for Using Modified-Nucleotide-Capped RNA for Making Vaccines or Immunotherapeutic Products In some embodiments the present invention provides methods wherein the modified-nucleotide-capped RNA is translated in vivo, the eukaryotic cell is a human or animal cell of a patient and said cell is transformed by the modified-nucleotide-capped RNA having a poly(A) tail by direct injection into the patient, such as by intradermal injection of a human patient as described by Carralot, J-P, et al. (Genetic Vaccines and Therapy 3: 6, 2005). Thus, in some embodiments, the modified-nucleotide-capped RNA comprises a composition for use as a vaccine for treating or preventing a condition, such as a cancer condition or a pathogen-induced condition. In some embodiments, the invention further comprises using the modified-nucleotide-capped RNA having a poly(A) tail to make a composition comprising a vaccine, which vaccine can be administered to patients as one or more injections of a therapeutically effective amount. In some embodiments, the composition comprises polyadenylated modified-nucleotide-capped RNA derived from primary RNA transcripts amplified using cDNA prepared from tumor-specific or pathogen-specific mRNA.

In some other embodiments of the method wherein the modified-nucleotide-capped RNA is translated in vivo in a eukaryotic cell, the modified-nucleotide-capped RNA has either a cap 0 or a cap I structure and is polyadenylated and the eukaryotic cell is an antigen-presenting cell (APC) selected from the group consisting of a dendritic cell, a macrophage, an epithelial cell, or an artificially generated APC from a human or an animal. In some embodiments, the method further comprises the step of using the modified-nucleotide-capped RNA to make an RNA-loaded APC for use as a vaccine. In a preferred embodiment, the RNA-loaded APC is a dendritic cell. With respect to the methods and kits of the present invention for preparing an RNA-loaded APC using a modified-nucleotide-capped RNA, and for using said RNA-loaded APC as a vaccine, methods and compositions known in the art with respect to other RNA molecules can be used, as described in U.S. Patent Application Nos. 20020018769; and 20060057130; and in U.S. Pat. Nos. 6,670,186; 6,387,701; 6,306,388; 5,853,719; and 5,831,068, and in Boczkowski, D et al., J. Exp. Med. 184: 465-472, 1996; Heiser, A et al., J. Clinical Investigation 109: 409-417, 2002; Su, Z et al., Cancer Res. 63: 2127-2133, 2003; Gilboa, E and Vieweg, J, Immunol. Rev. 199: 251-263, 2004; Harris, J et al., BBA 1724: 127-136, 2005; and Mockey, M et al. (Biochem. Biophys. Res. Comm. 340: 1062, 2006).

In some embodiments, the modified-nucleotide-capped RNA encodes a tumor antigen. In some embodiments, the modified-nucleotide-capped RNA encodes an antigen against a pathogen, such as a bacterial, viral or fungal antigen, or an antigen induced in a human or animal upon infection by such pathogen. Thus, some embodiments of the invention comprise a method for producing an RNA-loaded APC that presents on its surface a tumor antigenic epitope or a pathogen antigenic epitope encoded by the RNA, wherein the epitope induces T cell proliferation, said method further comprising the step of introducing the polyadenylated modified-nucleotide-capped RNA encoding the antigens into an antigen-presenting cell. By "RNA-loaded" antigen-presenting cell is meant an APC (e.g., a macrophage or dendritic cell) that was incubated or transfected with RNA (e.g., RNA derived from a tumor or pathogen or from eukaryotic cells infected by a pathogen). Such RNA can be loaded into the APC by using conventional nucleic acid transfection methods, such as lipid-mediated transfection, electroporation, and calcium phosphate transfection. For example, but without limitation, modified-nucleotide-capped RNA can be introduced into an APC by incubating the APC with the modified-nucleotide-capped RNA (or extract) for 1 to 24 hours (e.g., 2 hours) at 37° C., preferably in the presence of a cationic lipid.

In some embodiments of the method, the uncapped RNA comprising primary RNA transcripts or RNA having a 5'-diphosphate used to obtain the polyadenylated modified-nucleotide-capped RNA is transcribed from clones in a cDNA library prepared from amplified tumor mRNA (or from pathogen-specific mRNA). In some embodiments, the modified-nucleotide-capped RNA is transcribed from clones in a cDNA library prepared as described by Carralot J-P, et al. (Genetic Vaccines and Therapy 3: 6, 2005). In preferred embodiments of the invention, the polyadenylated modified-nucleotide-capped RNA is prepared from uncapped RNA comprising primary RNA transcripts or RNA having a 5'-diphosphate obtained following fractionation by subtractive hybridization, digestion and RNA amplification of RNA from a biological source, whereby in vivo translation of the polyadenylated modified-nucleotide-capped RNA in the APC results in presentation of only condition-specific antigens by the APC. In some embodiments, the polyadenylated modified-nucleotide-capped RNA is prepared from RNA obtained by subtractive hybridization and digestion. In some embodiments, the subtractive hybridization, digestion, and RNA amplification is performed as described in U.S. Pat. No. 5,712,127. In other preferred embodiments, the polyadenylated modified-nucleotide-capped RNA is prepared from RNA obtained by subtractive hybridization and digestion using the cap-dependent subtraction method of the present invention. In some embodiments, the uncapped RNA that is used to synthesize the modified-nucleotide-capped RNA is amplified using an in vitro transcription reaction or RNA amplification reaction. In some embodiments, the uncapped RNA is amplified using the RNA amplification method described in U.S. Patent Application No. 20050153333 of Sooknanan. In some embodiments, the subtracted and amplified uncapped RNA comprises RNA from a condition (e.g., a tumor cell condition) from which RNA that is also present in a normal cell of the same type has been removed by subtractive hybridization and the remaining RNA is then amplified using an RNA amplification reaction. Thus, in these embodiments, the polyadenylated modified-nucleotide-capped RNA made using the uncapped RNA comprising primary RNA transcripts or RNA having a 5'-diphosphate from this RNA amplification reaction is condition-specific (e.g., tumor-specific), and the APC (e.g., dendritic cell) also translates or expresses condition-specific (e.g., tumor-specific) polypeptides encoded by this RNA. In some embodiments of the invention, the polyadenylated modified-nucleotide-capped RNA is prepared using RNA derived from cancer cells. In other embodiments of the invention, the polyadenylated modified-nucleotide-capped RNA is prepared using RNA derived from a pathogen, such as a bacterial, viral or fungal pathogen, or from a eukaryotic cell that is infected by a bacterial, viral or fungal pathogen, whereby the APC translates or expresses polypeptides that are pathogen-specific. Thus, the invention also comprises a method for producing an RNA-loaded antigen presenting cell (APC), said method further comprising introducing into the APC the condition-specific polyadenylated modified-nucleotide-capped RNA, thereby producing an RNA-loaded APC. In some embodiments of this method, the condition-specific polyadenylated modified-nucleotide-capped RNA is selected from the group consisting of tumor-specific RNA and pathogen-specific RNA. The invention also comprises kits for performing such methods wherein the modified-nucleotide-capped RNA is translated in vivo following transformation of a living eukaryotic cell. For example, in some embodiments, the kit additionally comprises the eukaryotic cell and, optionally, transformation or transfection reagents (e.g., the cationic lipid DOTAP or 1:1 (w/w) DOTMA:DOPE (i.e., LIPOFECTIN) or other transfection reagents known in the art that are appropriate for the particular cell type). In some embodiments, the eukaryotic cell in the kit is an oocyte (e.g., a *Xenopus* oocyte), or a somatic cell of any type from a human, an animal, a plant, or a fungus. In some embodiments, the eukaryotic cell in the kit is an APC selected from the group consisting of a dendritic cell, a macrophage, an epithelial cell, and an artificially generated APC from a human or an animal. The present invention also comprises a eukaryotic cell that is transformed or transfected with a modified-nucleotide-capped RNA having a cap 0 or a cap I structure, including a polyadenylated modified-nucleotide-capped RNA. In some embodiments, the invention comprises an APC, including a dendritic cell, a macrophage, an epithelial cell, or an artificially generated APC from a human or an animal, that is transformed or transfected with a modified-nucleotide-capped RNA having a cap 0 or a cap I structure, including a polyadenylated modified-nucleotide-capped RNA, and which APC is capable of producing antigenic epitopes encoded by said modified-nucleotide-capped RNA on its surface. The invention further provides a method for treating or preventing a condition in a human or animal, such as a cancer condition or a pathogen-induced condition, said method comprising administering to the patient a therapeutically effective amount of the RNA-loaded APC obtained by introduction into said APC of the polyadenylated modified-nucleotide-capped RNA prepared from uncapped RNA derived from primary RNA transcripts from cells having said condition. In some embodiments, the APC is from the patient with the condition. In some embodiments, the APC is from a donor who is not the patient. In some embodiments the modified-nucleotide-capped RNA is derived from a biological specimen from the patient with the condition (e.g., from the tumor of the patient who has the tumor). In some embodiments, the modified-nucleotide-capped RNA is from a biological specimen from another person with the condition. The invention also provides a method for producing a cytotoxic T lymphocyte (CTL), said method comprising: providing a T lymphocyte; contacting said T lymphocyte in vitro with the RNA-loaded APC comprising the modified-nucleotide-capped RNA; and maintaining said T lymphocyte under conditions conducive to CTL proliferation, thereby producing a CTL. The invention also includes the CTL produced according to this method. In some embodiments, the T lymphocyte is derived from a donor. In some embodiments, the uncapped RNA comprising primary RNA transcripts or RNA having a 5'-diphosphate that is used to make the condition-specific (e.g., tumor-specific or pathogen-specific) modified-nucleotide-capped RNA for loading the APC is derived from the patient with the condition that receives this treatment. In some embodiments, the uncapped RNA comprising primary RNA transcripts or RNA having a 5'-diphosphate that is used to make the condition-specific modified-nucleotide-capped RNA for loading the APC is derived from a donor. The invention further provides a method for treating or preventing a condition, such as tumor formation or a pathogen infection, in a human or animal patient, said method comprising administering to the patient a therapeutically effective amount of the CTL obtained using this method. In some embodiments, the T lymphocyte is derived from the patient with the condition.

Some embodiments of the invention comprise a eukaryotic cell that contains a modified-nucleotide capped RNA synthesized using a method of the present invention, or a eukaryotic cell that contains a peptide that is translated from the modified-nucleotide capped RNA. In some embodiments, the eukaryotic cell that contains the modified-nucleotide-capped RNA having either a cap 0 or a cap I structure, or with our without a poly(A) tail, is an oocyte (e.g., a *Xenopus* oocyte), or a somatic cell of any type from a human, an animal, a plant, or a fungus. In some embodiments, the eukaryotic cell is an APC, such as, but not limited to a dendritic cell, a macrophage, an epithelial cell, or an artificially generated APC from a human or an animal. In some embodiments, the modified-nucleotide-capped RNA encodes a tumor antigen (i.e., a tumor-specific antigen) or an antigen from a bacterial, viral or fungal pathogen or from a eukaryotic cell that is infected by a bacterial, viral or fungal pathogen (i.e., a pathogen-specific antigen). Thus, some embodiments of the invention comprise a modified-nucleotide-capped RNA-loaded antigen-presenting cell (APC) that presents on its surface a tumor-specific antigenic epitope or a pathogen-specific antigenic epitope encoded by the RNA, wherein the epitope induces T cell proliferation.

Methods and Kits for In Vivo Expression of Prokaryotic Bacterial mRNA in Eukaryotes The present invention also provides methods for synthesizing a modified-nucleotide-capped RNA by capping of uncapped RNA comprising primary RNA transcripts or RNA having a 5'-diphosphate using a capping enzyme system and a modified cap nucleotide that provides a method for expressing one or more prokaryotic (e.g., bacterial) mRNA transcripts in a eukaryotic cell. Thus, in some preferred embodiments, the method is used to express or screen for expression of prokaryotic mRNA that encodes a desired enzymatic activity or polypeptide in a eukaryotic cell, said method comprising: (i) providing a sample containing prokaryotic mRNA, a capping enzyme system, a modified cap nucleotide, and a eukaryotic cell; (ii) contacting the prokaryotic mRNA with the capping enzyme system and the modified cap nucleotide under conditions wherein modified-nucleotide-capped RNA is synthesized; (iii) transforming the eukaryotic cell with the modified-nucleotide-capped RNA and incubating said transformed eukaryotic cell in a medium and under conditions that sustain said eukaryotic cell; and (iv) detecting or screening for the presence of the enzymatic activity or polypeptide in the eukaryotic cell. However, the invention is not limited to the use of a modified cap nucleotide for expressing prokaryotic mRNA in a eukaryotic cell. The method can be used with any cap nucleotide that is a substrate for the capping enzyme system, including a cap nucleotide or a cap nucleotide that is not a modified cap nucleotide (e.g., GTP). Thus, in some preferred embodiments, the method is used to express or screen for expression of prokaryotic mRNA that encodes a desired enzymatic activity or polypeptide in a eukaryotic cell, said method comprising: (i) providing a sample containing prokaryotic mRNA, a capping enzyme system, a cap nucleotide, and a eukaryotic cell; (ii) contacting the prokaryotic mRNA with the capping enzyme system and the cap nucleotide under conditions wherein capped RNA is synthesized; (iii) transforming a eukaryotic cell with the modified-nucleotide-capped RNA and incubating said transformed eukaryotic cell in a medium and under conditions that sustain said eukaryotic cell; and (iv) detecting or screening for the presence of the enzymatic activity or polypeptide in the eukaryotic cell. Thus, the present invention encompasses the use of a cap nucleotide that is not a modified cap nucleotide in all of the embodiments of the present invention that comprise expressing a prokaryotic primary RNA (e.g., bacterial or mycoplasmal mRN) in a eukaryotic cell, unless said embodiment requires the use of a modified cap nucleotide that comprises a chemical moiety for capture or labeling of the modified cap nucleotide. In some embodiments of the above methods for expressing a prokaryotic primary RNA in a eukaryotic cell, the modified-nucleotide-capped RNA (or capped RNA) synthesized using the method has a cap 0 structure, whereas in other embodiments, the modified-nucleotide-capped RNA (or capped RNA) synthesized has a cap I structure (i.e., it has a 2'-O-methyl group on the penultimate nucleotide. In preferred embodiments, the modified-nucleotide-capped RNA (or capped RNA) that is used to transform the eukaryotic cell in step (ii) additionally comprises a poly(A) tail on the 3'-terminus. The method provides a powerful way to identify and screen for prokaryotic mRNA having a desired enzymatic activity or effect in a eukaryotic cell, or for producing a polypeptide in the eukaryotic cell that has a beneficial effect or useful application (e.g., for expressing an antigen in an antigen-presenting cell loaded with the modified-nucleotide-capped RNA (or capped RNA), as described elsewhere herein. For example, but without limitation, the method can be used for screening all prokaryotic mRNA from one or more prokaryotic organisms (e.g., bacterium) for the desired enzymatic activity or effect.

In this embodiment, the uncapped RNA that is capped using the capping enzyme system comprises one or more prokaryotic mRNA transcripts (e.g., bacterial mRNA), and the method additionally comprises transforming a eukaryotic cell with the modified-nucleotide-capped RNA and assaying or screening for the activity or effects of the proteins encoded by said one or more prokaryotic mRNA transcripts in the eukaryotic cell. In some embodiments, the modified-nucleotide-capped RNA that is used to transform the eukaryotic cell comprises prokaryotic bacterial mRNA that is capped with a capping enzyme system using a modified cap nucleotide comprising a modified 2'- or 3'-deoxyguanosine-5'-triphosphate wherein the respective 2'- or 3'-deoxy position of the sugar moiety is substituted by a moiety comprising an amino group, an azido group, a fluorine group, or a methoxy group, or a modified guanosine-5'-triphosphate wherein the O6 oxygen of the guanine base is modified by being substituted with an alkyl group. In some embodiments, the modified cap nucleotide is selected from the group consisting of $O^6$-Me-GTP, 2'-amino-2'-dGTP, 2'-azido-2'-dGTP, 2'-fluoro-2'-dGTP, 2'-OMe-GTP, 3'-amino-3'-dGTP, 3'-OMe-GTP, and 3'-dGTP. In some embodiments wherein the modified-nucleotide-capped RNA comprises a poly(A) tail or has a cap I structure, the modified cap nucleotide is 2'-dGTP. The invention is also not limited to use of a modified cap nucleotide or to use of a modified-nucleotide-capped RNA. Thus, in some embodiments, any nucleotide (e.g., GTP) that is a substrate for the capping enzyme system is used to synthesize capped prokaryotic mRNA having a poly(A) tail for screening for expression of prokaryotic mRNA in a eukaryotic cell. In preferred embodiments that comprise synthesizing modified-nucleotide-capped RNA, the modified-nucleotide-capped RNA comprising prokaryotic bacterial mRNA that is used to transform the eukaryotic cell has a 3'-poly(A) tail. In some embodiments, which are preferred, the 3'-polyadenylated modified-nucleotide-capped RNA comprising prokaryotic bacterial mRNA that is used to transform the eukaryotic cell additionally has a 2'-O-methyl group on the 5'-penultimate nucleotide (i.e., the cap of the modified-nucleotide-capped RNA has a cap I structure). In some embodiments, the prokaryotic mRNA that is used to synthesize the modified-nucleotide-capped RNA is first amplified using an in vitro transcription or RNA amplification reaction. In some embodiments, the prokaryotic mRNA is fractionated using subtractive hybridization, digestion, and RNA amplification. In some preferred embodiments, the prokaryotic mRNA is fractionated using the cap-dependent subtraction method of the present invention. In some such embodiments, a poly(A) tail is synthesized on the 3'-terminus of amplified prokaryotic mRNA or the modified-nucleotide-capped RNA by in vitro transcription of a DNA template that encodes the prokaryotic mRNA and the poly(A) tail. The invention also comprises a composition of a modified-nucleotide-capped RNA comprising prokaryotic bacterial mRNA that is made using any of the methods of the invention.

Based on the above description, those with knowledge in the art will know how to use the method for a variety of applications and formats. The method can be used to screen mRNA from any of the vast diversity of prokaryotic organisms, whether previously cultured or not, for expression of protein activities that may be beneficial in a eukaryote for therapeutic or commercial applications. For example, but without limitation, the present invention contemplates using the method to screen for expression of prokaryotic mRNA in eukaryotes in order to identify a protein activity that will effectively complement a protein activity that is absent or deleted or mutated so as to result in a disease, susceptibility or metabolic problem in a human or other eukaryote. In other embodiments, the method is used to screen for an enzymatic activity that is absent in a metabolic pathway that is expressed in a eukaryotic cell. In some embodiments, the enzymatic activity of the metabolic pathway that is absent is an enzymatic activity encoded by a gene that is mutated in the eukaryotic cell. In other embodiments, the metabolic pathway comprises genes from another organism that are expressed in the eukaryotic cell and the gene that encodes the missing enzymatic activity is not present or is not sufficiently expressed in the eukaryotic cell. In some embodiments, the metabolic pathway comprising genes from another organism that is expressed in the eukaryotic cell is expressed from genes that are cloned in a vector, such as a plasmid, cosmid, BAC, fosmid, transposon, phage, or other DNA vector. Still further, in some embodiments, the present invention contemplates using the method to screen for expression of prokaryotic mRNA in a eukaryote in order to identify a protein activity that will be useful for a commercial process, such as to provide an enzymatic activity that will more efficiently convert specific types of biomass to ethanol, n-butanol or other desired chemical compounds. Once primary prokaryotic mRNA transcripts are identified with the desired activity, cDNA corresponding to the mRNA that encodes the activity is cloned, genetically engineered, and expressed in the appropriate fungal, plant or other eukaryotic organism for the intended commercial purpose. Although much work has been carried out in the prior art on using DNA from prokaryotes in order to identify genes with useful activities, little or no work has been performed to use prokaryotic mRNA transcripts to identify such useful activities. The present invention provides methods for doing so, which the present inventors contemplate are much more efficient and productive than previous methods of screening for DNA for useful activities. This is because modified-nucleotide-capped and polyadenylated prokaryotic bacterial mRNA, prepared using the methods of the present invention, is likely to be expressed in eukaryotes without additional modification of the mRNA, whereas DNA requires complicated additional genetic manipulations, such as addition of appropriate promoters, expression of tRNAs optimal for codon usage in the organism, and use of other regulatory elements in order to obtain expression of the gene in the eukaryote.

It is not currently known in the art to use a capping enzyme system and a cap nucleotide to make a composition comprising capped prokaryotic mRNA, or to additionally make a composition comprising capped prokaryotic mRNA having a poly(A) tail on its 3'-terminus for expressing said capped and polyadenylated prokaryotic mRNA in a eukaryotic cell. Therefore, the methods and kits of the invention for expressing prokaryotic (e.g., bacterial) mRNA in a eukaryotic cell are not limited to the use of a modified cap nucleotide or use of a modified-nucleotide-capped RNA. In some embodiments, any nucleotide (e.g., GTP) that is a substrate for the capping enzyme system is used to synthesize capped prokaryotic RNA that is used in the method to transform the eukaryotic cell and to screen for expression. Thus, the invention further provides a general method for expressing prokaryotic (e.g., bacterial) mRNA in a eukaryotic cell and screening the prokaryotic mRNA for expression of a desired enzymatic activity or structural protein in a eukaryotic cell, said method comprising: (i) providing an uncapped prokaryotic RNA comprising primary RNA transcripts or RNA having a 5'-diphosphate, a capping enzyme system, and a cap nucleotide comprising a nucleotide that can be used by the capping enzyme system to cap the uncapped RNA; (ii) contacting the prokaryotic RNA with the capping enzyme system and the cap nucleotide under conditions wherein capped prokaryotic RNA is synthesized; (iii) treating the capped prokaryotic RNA under conditions wherein capped prokaryotic RNA having a poly(A) tail on its 3'-terminus is obtained; (iv) transforming a eukaryotic cell with the capped prokaryotic RNA having a poly(A) tail and incubating said transformed eukaryotic cell in a medium and under conditions that sustain viability; and (v) screening for the presence of the enzymatic activity or protein in the eukaryotic cell. In some embodiments, the step of treating the capped prokaryotic RNA in step (iii) comprises contacting the prokaryotic RNA or the capped prokaryotic RNA with poly(A) polymerase and ATP under conditions wherein the poly(A) tail is synthesized on its 3'-terminus. In some preferred embodiments, the prokaryotic RNA is bacterial mRNA. In some embodiments, the prokaryotic RNA that is used to synthesize the capped prokaryotic RNA is first amplified using an in vitro transcription or RNA amplification reaction. In some embodiments, the prokaryotic RNA is fractionated using subtractive hybridization, digestion, and RNA amplification. In some preferred embodiments, the prokaryotic RNA is fractionated using the cap-dependent subtraction method of the present invention. In some such embodiments, a poly(A) tail is synthesized on the 3'-terminus of amplified prokaryotic RNA or amplified and capped prokaryotic RNA by in vitro transcription of a DNA template that encodes the amplified prokaryotic RNA and the poly(A) tail. In some embodiments, the invention also comprises a composition of a capped prokaryotic RNA having a poly(A) tail that is made using any of the methods of the invention.

The invention further comprises use of any and all methods of the invention in human or animal cells or in vivo in animals for research purposes in order to investigate the effects of such method for purposes, such as, but not limited to, therapeutic purposes.

Methods and Kits for Cap-Dependent Capture (CDC) and Cap-Dependent Subtraction (CDS): Capture, Isolation, Purification, and Subtraction of Uncapped RNA A. Summary of Cap-Dependent Capture (CDC)

One embodiment of the invention provides a method for capturing, isolating and/or purifying uncapped RNA comprising primary RNA or RNA having a 5'-diphosphate in a sample. Thus, one embodiment is a method for "cap-dependent capture" ("CDC") of uncapped RNA comprising primary RNA transcripts or RNA having a 5'-diphosphate, the method comprising: (i) providing a sample comprising the uncapped RNA; a capping enzyme system; a modified cap nucleotide, wherein the modified cap nucleotide contains a chemical binding moiety to facilitate binding to an affinity-tag-binding molecule; and a surface, to which the affinity-tag-binding molecule is attached; (ii) contacting the uncapped RNA with the capping enzyme system and the modified cap nucleotide under conditions wherein modified-nucleotide-capped RNA is synthesized; (iii) contacting the modified-nucleotide-capped RNA with reagents and under conditions that facilitate binding of the modified cap nucleotide to the surface to which the affinity-tag-binding molecule is attached; and (iv) contacting the modified-nucleotide-capped RNA to the surface to which the affinity-tag-binding molecule is attached under conditions wherein the modified-nucleotide-capped RNA is bound to the surface, thereby capturing the modified-nucleotide-capped RNA. In some embodiments of the cap-dependent capture method, the chemical binding moiety of the modified cap nucleotide provided in step (i) comprises an affinity tag that is capable of binding the affinity-tag-binding molecule and step (iii) comprises incubating the modified-nucleotide-capped RNA in a buffer and under conditions that facilitate binding of the modified cap nucleotide to surface to which the affinity-tag-binding molecule is attached. In some other embodiments of the cap-dependent capture method, the modified cap nucleotide provided in step (i) contains a chemical binding moiety comprising an amino, an azido, or a thiol group and step (iii) comprises contacting the modified-nucleotide-capped RNA with an affinity tag reagent under conditions wherein the affinity tag is chemically joined to the chemical binding moiety, and further incubating the modified-nucleotide-capped RNA in a buffer and under conditions that facilitate binding of the modified cap nucleotide to the surface to which the affinity-tag-binding molecule is attached. Thus, one embodiment of the invention comprises a kit for cap-dependent capture (CDC), the kit comprising: (i) a capping enzyme system; (ii) a modified cap nucleotide, wherein the modified cap nucleotide contains a chemical binding moiety to facilitate binding to an affinity-tag-binding molecule; and (iii) a surface, to which the affinity-tag-binding molecule is attached. In some embodiments of the kit for CDC, the chemical binding moiety of the modified cap nucleotide comprises an affinity tag that is capable of binding the affinity-tag-binding molecule. In other embodiments of the kit for CDC, the chemical binding moiety of the modified cap nucleotide comprises an amino, an azido, or a thiol group, and the kit additionally comprises: (iv) an affinity tag reagent that is capable of reacting with the respective amino, azido, or thiol group of the modified cap nucleotide, thereby chemically joining the affinity tag to the chemical binding moiety of the modified cap nucleotide. In preferred embodiments of the methods and kits for cap-dependent capture, the affinity tag is biotin and the affinity-tag-binding molecule is streptavidin or avidin.

In some preferred embodiments of the cap-dependent capture method, the sample comprising the uncapped RNA also comprises other nucleic acids which are not primary RNA transcripts or RNA having a 5'-diphosphate, and method further comprises the step of: (v) separating the modified-nucleotide-capped RNA that is bound to the surface from the other nucleic acids which are not primary RNA transcripts or RNA having a 5'-diphosphate. In some preferred embodiments, the step of separating the modified-nucleotide-capped RNA that is bound to the surface from the other nucleic acids which are not primary RNA transcripts or RNA having a 5'-diphosphate comprises washing the surface to which the modified-nucleotide-capped RNA is bound. Thus, in some embodiments of the kit for CDC, the kit additionally comprises: (v) a solution for washing the surface to which the modified-nucleotide-capped RNA is bound.

In some embodiments, the method for cap-dependent capture further comprises the step of: (vi) contacting the modified-nucleotide-capped RNA that is bound to the surface with a protein or biochemical reagent under conditions wherein the triphosphate between the modified cap nucleotide and the 5'-penultimate nucleotide of the modified-nucleotide-capped RNA is cleaved, thereby de-capping the modified-nucleotide-capped RNA and releasing the de-capped RNA therefrom. In some preferred embodiments, the protein or biochemical reagent that cleaves the triphosphate is a pyrophosphatase or decapping enzyme. In some preferred embodiments, the protein or biochemical reagent that cleaves the triphosphate is selected from the group consisting of tobacco acid pyrophosphatase, *Saccharomyces cerevisiae* decapping enzyme, and human decapping enzyme. Thus, the method provides a substantially purified de-capped RNA from the captured modified-nucleotide-capped RNA that is bound to the surface. The substantially purified de-capped RNA is useful for additional analysis and use. Thus, in some embodiments of the kit for CDC, the kit additionally comprises: (vi) a protein or biochemical reagent that is capable of specifically cleaving the triphosphate in the modified-nucleotide-capped RNA between the modified cap nucleotide and the 5'-penultimate nucleotide of the modified-nucleotide-capped RNA without cleaving other positions in the modified-nucleotide-capped RNA. In some preferred embodiments of the kit, the protein or biochemical reagent that is capable of specifically cleaving the triphosphate selected from the group consisting of tobacco acid pyrophosphatase, *Saccharomyces cerevisiae* decapping enzyme, and human decapping enzyme.

Thus, method for cap-dependent capture (CDC) of uncapped RNA is an embodiment of the basic method comprising contacting an uncapped RNA comprising primary RNA transcripts or RNA having a 5'-diphosphate with a capping enzyme system and a modified cap nucleotide under condition wherein the uncapped RNA is capped and a modified-nucleotide-capped RNA is synthesized, the method further comprising capturing the modified-nucleotid-capped RNA synthesized. In these embodiments, the method relies on binding the modified cap nucleotide, which requires that it can be specifically joined through a chemical moiety on the cap nucleotide to an affinity tag. Thus, in some embodiments of this method, the modified cap nucleotide comprises a guanine nucleoside-5'-triphosphate wherein the 2'- or 3'-position of the sugar comprises an amino, an azido, or a thiol group, or the 6-position of the guanine base is a thiol, and the method further comprises the step of contacting the modified cap nucleotide or the modified-nucleotide-capped RNA synthesized with the affinity tag reagent under conditions wherein the affinity tag is chemically joined to the respective amino, azido, or thiol group thereof. In some embodiments of the cap-dependent capture method or kit, the modified cap nucleotide comprises: (a) 2'- and/or 3'-deoxyguanosine-5'-triphosphate having a 2' or 3' substituent consisting of an amino, an azido, or a thiol group; or (b) a 6-thioguanine nucleoside-5'-triphosphate consisting of 6-thio-GTP, 6-thio-2'-dGTP, or 6-thio-3'-dGTP. In some preferred embodiments of the method or kit, the modified cap nucleotide is selected from among: 2'-amino-2'-dGTP; 3'-amino-3'-dGTP; 2'-azido-2'-dGTP; 3'-azido-3'-dGTP; 2'-mercapto-2'-dGTP (i.e. 2'-SH-2'-dGTP); 3'-mercapto-3'-dGTP; 2'-amino-2',3'-ddGTP 3'-amino-2',3'-ddGTP; 2'-azido-2',3'-ddGTP; 3'-azido-2',3'-ddGTP; 2'-mercapto-2',3'-dGTP; 3'-mercapto-2',3'-ddGTP; 6-thio-GTP (i.e., 6-mercapto-GTP); 6-thio-2'-dGTP; and 6-thio-3'-dGTP. Thus, in some embodiments of the method, a composition comprising modified-nucleotide-capped RNA having the affinity tag is obtained, which compositions are also part of the invention.

The cap-dependent capture methods can be used for capturing, isolating and/or purifying any uncapped RNA comprising primary RNA or RNA having a 5'-diphosphate in a sample, including such uncapped RNA that is in a sample that also includes other nucleic acids that are not primary RNA transcripts or RNA having a 5'-diphosphate.

B. Summary of Cap-Dependent Subtraction (CDS)

In some embodiments wherein the method for cap-dependent capture (CDC) is used, the method additionally comprises steps for subtracting (or removing) those RNAs that are present in or derived from a first sample comprising one or more cells of a first type or condition that are also present in a second sample comprising one or more cells of a second type or condition; thus, this method, which is referred to herein as "cap-dependent subtraction" or "CDS", is useful for obtaining a "subtraction library" of RNA molecules that are only present in the first sample, but are not present in the second sample. The method for cap-dependent subtraction comprises: (i) using the method of cap-dependent capture (CDC) to capture modified-nucleotide-capped RNA comprising RNA derived from a first sample comprising one or more cells of a first type or condition on a surface; (ii) contacting RNA derived from a second sample comprising one or more cells of a second type or condition with one or more primers that anneal to the RNA and an RNA-dependent DNA polymerase under conditions wherein first-strand cDNA that is complementary to the RNA from the second sample is synthesized, provided that, the first-strand cDNA has such a polarity or complementarity that, if the same RNA is present in the first sample, it will be complementary to the first-strand cDNA prepared from the RNA derived from the second sample; and (iii) contacting the captured modified-nucleotide-capped RNA comprising RNA derived from the first sample with the first-strand cDNA prepared from the RNA derived from the second sample under conditions wherein the first-strand cDNA from the second sample anneals to complementary captured modified-nucleotide-capped RNA from the first sample; and (iv) contacting the nucleic acids in step (iii) with RNase H under conditions wherein RNA that is annealed to DNA is digested, thereby subtracting from the captured modified-nucleotide-capped RNA derived from the first sample those modified-nucleotide-capped RNA molecules or nucleic acid sequences that are also present in the RNA derived from the second sample. Thus, one embodiment of the invention comprises a kit for cap-dependent subtraction (CDS), the kit comprising: (i) the components of the kit for cap-dependent capture, including the capping enzyme system, the modified cap nucleotide, and the surface, to which the affinity-tag-binding molecule is attached; and additionally comprising: (ii) an RNA-dependent DNA polymerase and one or more primers for synthesis of first-strand cDNA derived from the second sample; and (iii) RNase H. In some embodiments of the components for CDC, the chemical binding moiety of the modified cap nucleotide comprises an affinity tag that is capable of binding the affinity-tag-binding molecule. In other embodiments of the components for CDC, the chemical binding moiety of the modified cap nucleotide comprises an amino, an azido, or a thiol group, and the kit additionally comprises the affinity tag reagent that is capable of reacting with the respective amino, azido, or thiol group of the modified cap nucleotide, thereby chemically joining the affinity tag to the chemical binding moiety of the modified cap nucleotide. In preferred embodiments of the methods and kits for cap-dependent subtraction, the affinity tag is biotin and the affinity-tag-binding molecule is streptavidin or avidin.

In some preferred embodiments, the cap-dependent subtraction method further comprises the step of: (v) washing the surface to which the captured modified-nucleotide-capped RNA derived from the first sample is bound under conditions wherein the RNA that was digested by RNase H is removed and wherein other nucleic acids, including the first-strand cDNA prepared from the RNA derived from the second sample is removed. Thus, in some embodiments of the kit for CDS, the kit additionally comprises a solution for washing the surface to which the modified-nucleotide-capped RNA is bound.

In some preferred embodiments, the cap-dependent subtraction method further comprises the step of: (vi) contacting the captured modified-nucleotide-capped RNA derived from the first sample that remains bound to the surface with a protein or biochemical reagent under conditions wherein the triphosphate between the modified cap nucleotide and the 5'-penultimate nucleotide of the modified-nucleotide-capped RNA is cleaved, thereby de-capping the modified-nucleotide-capped RNA derived from the first sample and releasing the de-capped RNA derived from the first sample. Thus, some embodiments of the kit for CDS additionally comprise a pyrophosphatase or decapping enzyme. In some embodiments, the pyrophosphatase or decapping enzyme is selected from among tobacco acid pyrophosphatase and yeast or human decapping enzyme.

In the embodiments of cap-dependent subtraction, the de-capped RNA derived from the first sample that is released comprises those RNA molecules in the first sample which are not present in the second sample or which, if they are present in the second sample, are present in substantially lower quantity than in the first sample. In some embodiments, the first-strand cDNA prepared using RNA derived from the second sample is prepared from RNA amplified in an RNA amplification reaction, whereby the amount of first-strand cDNA that is prepared therefrom is in significant excess over the amount of the captured modified-nucleotide-capped RNA derived from the first sample, thereby increasing the probability that the captured modified-nucleotide-capped RNA derived from the first sample that is not digested by RNase H during the method is present only in the first sample or, is present in significantly larger amount in the first sample. In some embodiments wherein the method for cap-dependent subtraction (CDS) is used, the uncapped RNA derived from the first sample or first cell and/or the RNA derived from the second sample or second cell that used to synthesize the first-strand cDNA for the CDS method are synthesized using an in vitro RNA amplification reaction. In preferred embodiments, the in vitro RNA amplification reaction is a sense RNA amplification reaction that synthesizes uncapped RNA products comprising amplified sense RNA, also called "sense RNA", wherein the sequence is not different from the sequence of the RNA (e.g., from a cell, tissue, organ, or other biological sample) that is amplified using said sense RNA amplification method. In some preferred embodiments, the sense RNA amplification method is performed as described in U.S. Patent Application No. 20050153333 of Sooknanan; U.S. Patent Application No. 20030186237 of Ginsberg, Stephen; U.S. Patent Application No. 20040197802 of Dahl and Jendrisak; and U.S. Patent Application No. 20040171041 of Dahl et al.; or in Ozawa, T et al. (Biotechniques 40: 469-478, 2006). In some embodiments of a kit of the invention, the kit additionally comprises one or more enzymes or reagents for performing a sense RNA amplification reaction, including, but not limited to, a sense RNA amplification reaction as described above.

Thus, the cap-dependent subtraction (CDS) method provides a way to obtain a population of RNA molecules that is specific for the type of cell (i.e., "type-specific") or for the condition(s) to which it is subjected (i.e., "condition-specific"). This population of RNA molecules (sometimes referred to "subtracted RNA") is useful for further analysis or use. By way of example, but without limitation, the subtracted RNA can be identified (e.g. by analysis on an Affymetrix, Agilent, Illumina, or NimbleGen Systems microarray chip). If the subtracted RNA is from a cell with a condition, such as a cancer cell, or a cell from another organic disease, or a cell that is infected with a bacterial, mycoplasmal, fungal, or viral pathogen, it comprises a population of potential pharmaceutical drug targets, which, if further validated, can be used to develop pharmaceuticals to relieve symptoms or potentially cure the disease. Of course, a validated condition-specific target can also be used to develop human or animal diagnostic tests, assays and kits. The subtracted RNA is also useful for research purposes. For example, in one embodiment, subtracted RNA from a cancer stem cell is compared with subtracted RNA from normal cells of the same type and/or other cancer cells which are not stem cells from the cancer lesion in order to understand the progression of the cancer and develop therapies and treatments. In still another embodiment, the subtracted RNA is used for synthesis of capped and polyadenylated RNA, which is further used for making an RNA-loaded antigen-presenting cell (APC) for use as a vaccine to prevent or treat a disease (as discussed elsewhere, herein); for example, in some embodiments, subtracted RNA from the cancer stem cell from a tumor from a patient is used to make capped and polyadenylated RNA for use in transforming a dendritic cell prepared from the same patient, wherein the dendritic cell that is loaded with the tumor-specific RNA presents tumor-specific antigens. The tumor antigen-presenting dendritic cells are used to make a vaccine to attempt to induce a cell-mediated immune response in the patient. In still another embodiment, the tumor antigen-presenting dendritic cells are used to make cytotoxic T-lymphocytes (CTLs) in culture, and the CTLs are used to make a vaccine to treat the patient.

In some preferred embodiments, the protein or biochemical reagent that cleaves the triphosphate is a pyrophosphatase or decapping enzyme. In some preferred embodiments, the protein or biochemical reagent that cleaves the triphosphate is selected from the group consisting of tobacco acid pyrophosphatase, *Saccharomyces cerevisiae* decapping enzyme, and human decapping enzyme. Thus, the method provides a substantially purified de-capped RNA from the captured modified-nucleotide-capped RNA that is bound to the surface. The substantially purified de-capped RNA is useful for additional analysis and use. Thus, in some embodiments of the kit for CDC, the kit additionally comprises: (vi) a protein or biochemical reagent that is capable of specifically cleaving the triphosphate in the modified-nucleotide-capped RNA between the modified cap nucleotide and the 5'-penultimate nucleotide of the modified-nucleotide-capped RNA without cleaving other positions in the modified-nucleotide-capped RNA. In some preferred embodiments of the kit, the protein or biochemical reagent that is capable of specifically cleaving the triphosphate selected from the group consisting of tobacco acid pyrophosphatase, *Saccharomyces cerevisiae* decapping enzyme, and human decapping enzyme.

The methods for cap-dependent capture (CDC) and for cap-dependent subtraction (CDS) are very amenable to automation. Thus, in some embodiments, one or both of these methods is automated using a robot that is capable of robotic aliquoting, mixing, washing, temperature-controlled incubation, and liquid collection and transfer.

C. Detailed Description of Cap-Dependent Capture, Including Use for Capture, Isolation, and Purification of Prokaryotic Bacterial mRNA and Products from Transcription and RNA Amplification Reactions In some embodiments, wherein the method for cap-dependent capture (CDC) is used, the uncapped RNA comprises primary RNA transcripts from a prokaryotic or eukaryotic biological sample. In some preferred embodiments wherein the method for cap-dependent capture (CDC) is used, the uncapped RNA comprises prokaryotic (e.g., bacterial or mycoplasmal) primary RNA transcripts from a biological sample. In some embodiments wherein the CDC method is used to capture prokaryotic primary RNA transcripts, the sample contains both prokaryotic and eukaryotic mRNA. In some embodiments, the sample contains both one or more prokaryotic mRNA molecules and one or more eukaryotic mRNA molecules. The CDC method can be used to capture the prokaryotic mRNA in the sample without capturing the eukaryotic mRNA because the 5'-end of mRNA from a bacterial prokaryote has a 5'-triphosphate and is usually not capped, whereas the 5'-end of mRNA from a eukaryote is usually capped. Thus, the method can be used to capture prokaryotic (e.g., bacterial or mycoplasmal) mRNA in a sample that also contains capped eukaryotic mRNA. Thus, one embodiment of the invention is a method for selectively capturing or isolating prokaryotic bacterial mRNA, the method comprising (i) providing uncapped RNA comprising prokaryotic bacterial mRNA, a capping enzyme system, a modified cap nucleotide, and a surface, to which an affinity-tag-binding molecule is attached; (ii) contacting the uncapped RNA with the capping enzyme system and the modified cap nucleotide under conditions wherein the prokaryotic bacterial mRNA is capped and modified-nucleotide-capped RNA, which comprises the prokaryotic bacterial mRNA, is synthesized; and (iii) binding modified-nucleotide-capped RNA to the surface, whereby the modified-nucleotide-capped RNA, which comprises the prokaryotic bacterial mRNA, is captured. In some embodiments of this method, the modified-nucleotide-capped RNA synthesized has an affinity tag. In some embodiments of the method, the modified-nucleotide-capped RNA synthesized does not have an affinity tag and the method additionally provides an affinity tag reagent and the method further comprises the step of (iv) contacting the modified-nucleotide-capped RNA with the affinity tag reagent under conditions wherein the affinity tag is joined to the modified cap nucleotide therein, and modifiednucleotide-capped RNA that has an affinity tag is obtained. In some preferred embodiments, the method further comprises the step of: (v) contacting the modified-nucleotide-capped RNA that has the affinity tag with the surface to which the affinity-tag-binding molecule is attached under conditions wherein the modified-nucleotide-capped RNA is captured.

In some embodiments, the affinity-tag-binding molecule is attached to a surface selected from among: a glass slide, a dipstick, an array or microarray chip, a magnetic bead, a gold particle, a quantum dot, a microchannel in glass, silica or another material, a well of a tube, a well of a microtiter plate, or another surface known in the art that is capable of being used for attaching an appropriate affinity-tag-binding molecule. Many methods are known in the art for binding an affinity-tag-binding molecule to a surface, which can be used for the present invention. In some preferred embodiments of the above methods, the affinity tag is biotin and the affinity-tag-binding molecule is streptavidin or avidin. In some embodiments wherein an affinity tag reagent used, it is a biotinylation reagent. Thus, in some embodiments wherein the modified-nucleotide-capped RNA comprising biotin is bound to the surface to which streptavidin or avidin is attached, the prokaryotic mRNA is bound or captured, and thereby isolated from the mixture of nucleic acids and other molecules in the sample. The method can be used for a variety of applications. For example, but without limitation, in some embodiments, the prokaryotic mRNA is mRNA of a bacterial pathogen that is in the presence of mRNA of a eukaryotic host cell, and the method enables capture, isolation and purification of the mRNA of the bacterial pathogen, e.g., for further identification, analysis, and use. Thus, in some embodiments, the method for capturing the pathogenic bacterial mRNA can comprise a part of a molecular diagnostic method, assay or test; for example, the pathogenic bacterial mRNA on the surface, for example consisting of a dipstick, an array or microarray chip, magnetic beads, the inside of a tube, or the wells of a microtiter plate, can be annealed or hybridized to a labeled nucleic acid probe that is specific for the pathogen, thereby enabling detection and identification of the presence of the pathogen. In some embodiments, the molecular diagnostic method, assay or test can be configured to permit quantification of the amount of the pathogenic mRNA present in the sample, which can thereby indicate the quantity of the pathogen bacteria present in the sample. Without limitation, in still other embodiments, the captured or isolated prokaryotic mRNA that is released from the surface is amplified using a method known in the art for synthesizing amplified sense RNA having the same sequence as the prokaryotic mRNA, and this amplified sense RNA is contacted with a capping enzyme system and a cap nucleotide under conditions wherein it is capped, and contacted with a poly(A) polymerase and ATP under conditions wherein a poly(A) tail is added to the 3'-terminus, thereby obtaining 5'-capped amplified sense RNA having a 3'-poly(A) tail; in some embodiments the cap nucleotide is a modified cap nucleotide; in other embodiments, the amplified sense RNA is capped using a dinucleotide cap analog in an in vitro transcription reaction that is part of the sense RNA amplification method. In some preferred embodiments, the invention further comprises using the 5'-capped amplified sense RNA having a 3'-poly(A) tail to make a vaccine to prevent or treat a condition using methods described elsewhere herein. For example, but without limitation, in one preferred embodiment, the 5'-capped amplified sense RNA having a 3'-poly(A) tail that is synthesized using prokaryotic mRNA from a pathogenic bacterium or from a sample from a human or animal patient infected with the bacterium is used for transforming an antigen-presenting cell (APC), such as a dendritic cell, a macrophage, an epithelial cell, or an artificial APC, and using said transformed APC to make the vaccine. Alternatively, in some embodiments, said transformed APC is used as described elsewhere herein to make a cytotoxic T-lymphocyte (CTL) for use as a vaccine to prevent or treat a human or animal patient with the pathogen-infected condition.

As a further example wherein the cap-dependent capture (CDC) method can be used, in some embodiments, the uncapped RNA in the sample comprises prokaryotic mRNA from a plant root nodule that is infected with a symbiotic nitrogen-fixing *Rhizobium* bacterium, which prokaryotic mRNA is also in the presence of the eukaryotic plant mRNA. Since the plant eukaryotic mRNA is already capped, the Rhizobial mRNA can be selectively captured using the CDC method.

Although most eukaryotic mRNA has a poly(A) tail that can be used for selective synthesis of cDNA from the eukaryotic mRNA, which is a step in many RNA amplification methods (e.g., which are used to make labeled target RNA for use in gene expression analysis (e.g., using a microarray from Affymetrix, Agilent, Illumina, or NimbleGen Systems), most prokaryotic bacterial mRNA does not have a poly(A) tail that is capable of being used for such purposes. Thus, the present invention provides a novel method for selective capture and isolation of prokaryotic (e.g., bacterial) mRNA even in the presence of eukaryotic mRNA. Thus, the CDC method, when used in combination with methods known in the art, is enabling and extremely useful for analyzing gene expression by both the prokaryote and by the eukaryote using the same cell, tissue, organ, or other biological sample, thereby providing much better understanding of what is occurring when during the infection process. Thus, the cap-dependent capture (CDC) method has important applications for agriculture, human and animal medicine, and biomedical research.

In some embodiments wherein the method for cap-dependent capture (CDC) is used, the uncapped RNA comprises primary RNA transcripts or RNA having a 5'-diphosphate that is used for the method is the product of an in vitro transcription reaction using an RNA polymerase. In some embodiments, the RNA polymerase is a wild-type or mutant T7-type RNA polymerase. In some embodiments the T7-type RNA polymerase is selected from the group consisting of T7 RNA polymerase, T3 RNA polymerase, and SP6 RNA polymerase.

In some embodiments wherein the method for cap-dependent capture (CDC) is used, the uncapped RNA that is used for the method comprises primary RNA transcripts or RNA having a 5'-diphosphate that are products of an in vitro RNA amplification reaction. In some preferred embodiments, the in vitro RNA amplification reaction is a sense RNA amplification reaction that synthesizes uncapped RNA products comprising amplified sense RNA, also called "sense RNA", wherein the sequence is not different from the sequence of the RNA (e.g., from a cell, tissue, organ, or other biological sample) that is amplified using said sense RNA amplification method. Thus, in some preferred embodiments, the uncapped RNA comprising primary RNA transcripts or RNA having a 5'-diphosphate that is used for the method is a product of a sense RNA amplification reaction, such as, but not limited to, a method that synthesizes sense RNA as described in U.S. Patent Application No. 20050153333 of Sooknanan; U.S. Patent Application No. 20030186237 of Ginsberg, Stephen; U.S. Patent Application No. 20040197802 of Dahl and Jendrisak; and U.S. Patent Application No. 20040171041 of Dahl et al.; or in Ozawa, T et al. (Biotechniques 40: 469-478, 2006). In some embodiments of a kit of the invention, the kit additionally comprises one or more enzymes or reagents for performing a sense RNA amplification reaction, including, but not limited to, a sense RNA amplification reaction as described above.

However, in some embodiments, the uncapped RNA that is used for the CDC method is a product of an anti-sense RNA amplification reaction, such as, but not limited to an anti-sense RNA amplification reaction described in Murakawa et al., DNA 7:287-295, 1988; Phillips and Eberwine, Methods in Enzymol. Suppl. 10:283-288, 1996; Ginsberg et al., Ann. Neurol. 45:174-181, 1999; Ginsberg et al., Ann. Neurol. 48:77-87, 2000; VanGelder et al. Proc. Natl. Acad. Sci. USA 87:1663-1667, 1990; Eberwine et al., Proc. Natl. Acad. Sci. USA 89:3010-3014, 1992; U.S. Pat. Nos. 5,021,335; 5,168, 038; 5,545,522; 5,514,545; 5,716,785; 5,891,636; 5,958,688; 6,291,170; and PCT Patent Applications WO 00/75356 and WO 02/065093. In some embodiments of a kit of the invention, the kit additionally comprises one or more enzymes or reagents for performing an anti-sense RNA amplification reaction, including, but not limited to, an anti-sense RNA amplification reaction as described above.

The RNA that is amplified in the RNA amplification reaction (e.g., in either a sense RNA amplification reaction or an anti-sense RNA amplification reaction) in order to obtain uncapped RNA for use in the cap-dependent capture (CDC) method can be from one of a variety of sources. In some embodiments, the RNA that is amplified is from a biological sample, such as a cell, tissue, or organ of a human, plant, animal, bacterium, virus, or fungus, or from a preparation of RNA prepared therefrom using an RNA extraction or purification method or kit known in the art. In other embodiments, the RNA that is amplified to obtain the uncapped RNA for subsequent use in the CDC method is de-capped RNA obtained from a prior round of the CDC method, wherein the de-capped RNA comprises RNA that is released from the prior round of CDC by contacting the captured modified-nucleotide-capped RNA with a pyrophosphatase. In still other embodiments, the RNA that is amplified to obtain the uncapped RNA for subsequent use in the CDC method is de-capped RNA obtained from a prior round of the cap-dependent subtraction ("CDS") method described elsewhere herein; in this embodiment, the RNA that is amplified comprises "type-specific" or "condition-specific" RNA, from which RNA that is in common with RNA in another sample has been subtracted.

Based on the above description, it will be clear that the methods of the invention comprising contacting an uncapped RNA with a capping enzyme system and a modified cap nucleotide whereby modified-nucleotide-capped RNA is synthesized (including the CDC method) can be used with any uncapped RNA comprising primary RNA transcripts or RNA having a 5'-diphosphate, whether the uncapped RNA is obtained from an in vivo or biological source, or from an in vitro source. In fact, with respect to RNA obtained in vitro, each round of in vitro transcription or RNA amplification provides new uncapped RNA comprising primary RNA transcripts or RNA having a 5'-diphosphate which can be capped with a modified cap nucleotide using the method of the invention. The particular modified cap nucleotide can be the same for capping RNA from each round of in vitro transcription or a different modified cap nucleotide can be used for capping the uncapped RNA obtained from each round. By way of example, but without limitation, in some embodiments, 2'-amino-2'-dGTP is used as the modified cap nucleotide for capping primary mRNA transcripts from a first round of in vitro transcription or RNA amplification, permitting isolation of the modified-nucleotide-capped RNA obtained using the CDC method, and then another modified cap nucleotide (e.g., $O^6$-Me-GTP) is used for capping primary mRNA transcripts from a second round of in vitro transcription or RNA amplification, permitting higher efficiency translation of the RNA into protein in a eukaryotic cell (e.g., preferably after also polyadenylating the modified-nucleotide-capped RNA using poly(A) polymerase).

In some embodiments of the method in which prokaryotic bacterial mRNA is captured, isolated, purified and released by de-capping using the CDC methods of the invention, the method further comprises tailing the prokaryotic mRNA, such as by contacting the mRNA with poly(A) polymerase and ATP under conditions wherein a poly(A) tail is added to the 3'-termini. In some embodiments of the method in which prokaryotic mRNA is captured, isolated, purified and released by de-capping using the methods of the invention, the method further comprises adding a terminal sequence tag to the 3' termini of the released mRNA. In other embodiments, the method further comprises contacting the released mRNA with an RNA-dependent DNA polymerase and a primer under conditions wherein first-strand cDNA is synthesized and then, a tag is added to the 3' termini of the first-strand cDNA using the terminal tagging method described by Sooknanan in U.S. Patent Application Nos. 20050153333. In still other embodiments of the method in which prokaryotic mRNA is captured, isolated, purified and released by de-capping using the method of the invention, the method further comprises synthesizing first-strand cDNA by reverse transcription of the mRNA and tailing the first-strand cDNA by contacting the cDNA with a terminal transferase, such as calf thymus terminal deoxynucleotidyl transferase, in the presence of at least one deoxyribonucleoside-5'-triphosphate under terminal transferase reaction conditions. In some embodiments of the method in which a terminal sequence tag and/or a tail is added to the 3' termini of prokaryotic mRNA and/or cDNA derived by reverse transcription of the mRNA, the method further comprises amplifying the prokaryotic mRNA using an RNA amplification reaction. In preferred embodiments, the RNA amplification reaction synthesizes sense RNA. In other embodiments, the RNA amplification reaction synthesizes anti-sense RNA.

In some embodiments of the kit or method wherein the modified cap nucleotide has a 2' or 3' substituent consisting of an amino or an azido group or a thiol substituent on the 6-position of the guanine base, the kit or method additionally provides: an affinity tag reagent; and an affinity-tag-binding molecule, which is either free or attached to a surface; and the method additionally comprises the steps of: (i) contacting the modified-nucleotide-capped RNA with the affinity tag reagent under conditions wherein the affinity tag is chemically joined to the modified cap nucleotide of the modified-nucleotide-capped RNA, whereby modified-nucleotide-capped RNA having an affinity tag is obtained; and (ii) contacting the modified-nucleotide-capped RNA having the affinity tag with the affinity-tag-binding molecule under conditions wherein the modified-nucleotide-capped RNA having the affinity tag is bound, and the modified-nucleotide-capped RNA is captured, isolated or labeled. In some embodiments of the kit or method wherein the affinity tag comprises biotin, the affinity-tag-binding molecule is streptavidin or avidin, either free or attached to a surface and/or attached to another molecule, including, but not limited to a fluorescent or other detectable label.

In some embodiments of the kit or method, the affinity tag having the reactive moiety is a biotinylation reagent. Any biotinylation reagent known in the art that reacts with the amino, azido, or thiol group on the 2'- or 3'-position of the sugar or the thiol group on the 6 position of the guanine base of the respective modified cap nucleotide can be used in the methods and kits of the invention. Without limitation, some biotinylation reagents that can be used are described in "Avidin-Biotin Chemistry: A Handbook", by D. Savage et al., Pierce Chemical Company, 1992 and in "Handbook of Fluorescent Probes and Research Products", Ninth Edition, by R. P. Hoagland, Molecular Probes, Inc. Thus, without limitation, in some embodiments of the kit or method wherein the modified cap nucleotide comprises a 2'- or 3' thiol group, or 6-thioguanine, the biotinylation reagent comprises a thiol-reactive iodoacetamidyl-, iodoacetyl-, or maleimidyl-moiety. In some other embodiments of the kit or method wherein the modified cap nucleotide comprises a 2'- or 3'-amino or azido group, the affinity tag reagent is comprises a 6-[(+)-biotinamidocaproyl]-group or a 6-[(+)-biotinamidocaproylamido]-caproyl-group that has a reactive moiety comprising an N-hydroxysuccinimidyl (i.e., "NHS") ester that is capable of reacting with the amino group, or a reactive moiety comprising an alkynyl group that is capable of reacting with the azido group. For example, in some embodiments of the kit or method wherein the 2' or 3' substituent of the modified cap nucleotide is an amino group, the affinity tag reagent is biotin-X—X—NHS (also called biotin-LC-LC-NHS or 6-[(+)-biotinamidocaproylamido]-caproic acid N-hydroxysuccinimide ester) or biotin-X—NHS (also called biotin-LC-NHS). In other embodiments, a different biotinylation known in the art with a shorter or longer side chain and/or with a different reactive moiety is used. In some embodiments of the kit or method wherein the 2' or 3' substituent of the modified cap nucleotide is an azido group, the reactive moiety of the affinity tag is a reactive alkynyl group which is capable of joining the affinity binding molecule to the azido group via a 1,3-dipolar cycloaddition; in embodiments of the method, the affinity tag is joined to the modified cap nucleotide of the modified-nucleotide-capped RNA via a 1,2,3-triazole moiety. Affinity tag reagents having a reactive moiety consisting of an alkynyl group which can be used for the kits and methods of the present invention are known in the art (e.g., see Breinbauer, R and Kohn, M, Chem Bio Chem 4: 1147-1149, 2003), and those with knowledge in the art will understand how to obtain an affinity tag reagent having a reactive alkynyl group for other applications using such described methods. By way of example, but without limitation, the invention comprises a method for obtaining an affinity tag reagent having a reactive alkynyl group (e.g., a biotinylation reagent having a reactive alkynyl group), the method comprising reacting a compound having an affinity tag reagent having an amine-reactive moiety (e.g., biotin-X—X—NHS) with a molecule having a primary amine and an alkynyl group, thereby obtaining the affinity tag reagent having a reactive alkynyl group (e.g., biotin-X—X—NH-alkyne). Similarly, bioconjugation techniques for using such affinity tag reagents having a reactive alkynyl group (e.g., for bioconjugation to a modified-nucleotide-capped RNA having a modified cap nucleotide with a 2' or 3' azido group) are known in the art (e.g., see Breinbauer, R and Kohn, M, Chem Bio Chem 4: 1147-1149, 2003), which can be used in the kits and methods of the invention.

Thus, some embodiments of the invention comprise a method comprising: (i) contacting an uncapped RNA comprising primary RNA transcripts or RNA having a 5'-phosphate with a capping enzyme and a modified cap nucleotide containing an amino, azido or thiol group under conditions wherein a modified-nucleotide-capped RNA comprising a modified cap nucleotide having a reactive amino, azido or thiol group is synthesized. In some embodiments, the method further comprises one or more of the following steps: (ii) contacting the modified-nucleotide-capped RNA with an affinity tag reagent that is capable of chemically joining the affinity tag to the respective amino, azido or thiol group of the modified-nucleotide-capped RNA under conditions wherein modified-nucleotide-capped RNA having the affinity tag is synthesized; (iii) contacting the modified-nucleotide-capped RNA having the affinity tag to a surface to which an affinity-tag-binding molecule that is capable of binding the affinity tag, thereby binding and capturing or isolating the modified-nucleotide-capped RNA having the affinity tag; (iv) washing the surface to which the modified-nucleotide-capped RNA having the affinity tag is bound, thereby removing contaminants, including nucleic acids, that are not bound and purifying the modified-nucleotide-capped RNA having the affinity tag which is bound to the surface; and (v) contacting the surface to which the modified-nucleotide-capped RNA having the affinity tag is bound with an enzyme or reagent that cleaves the RNA of the modified-nucleotide-capped RNA from the bound modified cap nucleotide having the affinity tag, thereby releasing the purified RNA for further analysis and use.

Thus in some specific embodiments, the invention provides a kit for capturing or isolating uncapped RNA comprising primary RNA transcripts or RNA having a 5'-diphosphate, the kit comprising a capping enzyme system and a modified cap nucleotide selected from among: 2'-amino-2'-dGTP; 3'-amino-3'-dGTP; 2'-amino-2'-ddGTP; 3'-amino-3'-ddGTP; 2'-azido-2'-dGTP; 3'-azido-3'-dGTP; 2'-azido-2'-ddGTP; 3'-azido-3'-ddGTP; 2'-mercapto-2'-dGTP (i.e. 2'-SH-2'-dGTP); 3'-mercapto-3'-dGTP; 2'-mercapto-2',3'-dGTP; 3'-mercapto-2',3'-ddGTP; 6-thio-GTP (i.e., 6-mercapto-GTP); 6-thio-2'-dGTP; and 6-thio-3'-dGTP. The invention also provides a method for capturing and isolating uncapped RNA comprising primary RNA transcripts or RNA having a 5'-diphosphate, the method comprising: (i) providing an uncapped RNA comprising primary RNA transcripts or RNA having a 5'-diphosphate; a capping enzyme system; and a modified cap nucleotide selected from among 2'-amino-2'-dGTP, 3'-amino-3'-dGTP, 2'-amino-2'-ddGTP, 3'-amino-3'-ddGTP, 2'-azido-2'-dGTP, 3'-azido-3'-dGTP, 2'-azido-2'-ddGTP, 3'-azido-3'-ddGTP, 2'-mercapto-2'-dGTP; 3'-mercapto-3'-dGTP; 2'-mercapto-2',3'-dGTP; 3'-mercapto-2',3'-ddGTP; 6-thio-GTP, 6-thio-2'-dGTP and 6-thio-3'-dGTP; (ii) contacting the uncapped RNA with the capping enzyme system and the modified cap nucleotide under conditions wherein the modified-nucleotide-capped RNA is synthesized; (iii) contacting the modified-nucleotide-capped RNA with a biotinylation reagent (e.g., respectively, biotin-NHS ester or biotin-X—NHS ester or biotin-X—X—NHS ester or biotin-X—X-sulfo-NHS ester; biotin-X—X-propyne; and biotin-maleimide or biotin iodoacetamide) under conditions wherein the respective amino, azido, or thiol group is biotinylated and a biotinylated modified-nucleotide-capped RNA is obtained; (iv) contacting the biotinylated modified-nucleotide-capped RNA with streptavidin or avidin (e.g., that is attached to a surface) under conditions wherein the biotinylated modified-nucleotide-capped RNA is bound (e.g., to the surface); and (v) separating the bound biotinylated modified-nucleotide-capped RNA from unbound molecules (e.g., by washing). In some embodiments, the method further comprises the steps of: (vi) contacting the bound biotinylated modified-nucleotide-capped RNA with a pyrophosphatase (e.g., tobacco acid pyrophosphatase) under pyrophosphatase reaction conditions or a decapping enzyme (e.g., yeast or human decapping enzyme) under decapping enzyme reaction conditions, whereby the biotinylated modified-nucleotide-capped RNA that is bound (e.g., to a surface) is de-capped and the de-capped RNA is released; and (vii) obtaining the de-capped RNA that is released. Thus, in some embodiments, the kit further comprises a pyrophosphatase (e.g., tobacco acid pyrophosphatase) or a decapping enzyme (e.g., yeast or human decapping enzyme).

In some other specific embodiments, modified-nucleotide-capped RNA, prepared from a uncapped RNA comprising prokaryotic mRNA using a vaccinia capping enzyme system and 2'-amino-dGTP, is reacted with biotin-X—X—NHS ester (EPICENTRE Biotechnologies, Madison, Wis., USA) in the presence of 1-methyl-imidazole as a catalyst. The 2'-amino group of the modified cap nucleotide of the modified-nucleotide-capped RNA is thereby derivatized with a biotin affinity tag molecule, which is used to capture the biotinylated modified-nucleotide-capped RNA using streptavidin that is attached to a surface. In some embodiments, the surface is a magnetic bead, a dipstick, a membrane, the surface of the wells of a microtiter plate, an array or microarray slide of chip, or another solid or porous surface. In some embodiments, the biotinylated modified-nucleotide-capped RNA that is so captured is released by incubating with tobacco acid pyrophosphatase in 1× reaction buffer as described by the supplier (EPICENTRE Biotechnologies, Madison, Wis., USA), or by incubating with yeast or human decapping enzyme using conditions known in the art. The biotinylated modified-nucleotide-capped RNA can also be labeled by binding to streptavidin or avidin that is covalently attached to a detectable molecule, including, without limit, a visible, fluorescent, luminescent, or infrared fluorescent molecule, such as, but not limited to, phycoerythrin or another phycobiliprotein, fluorescein, rhodamine, Cy3, Cy5, or an Alexa dye, or another dye, or to streptavidin or avidin that is covalently attached to an enzyme that is detectable using a substrate, such as, but not limited to, a substrate that results in a visible, fluorescent, luminescent, or infrared fluorescent signal under enzymatic reaction conditions. The binding of the labeled streptavidin or avidin affinity-tag-binding molecule to the biotinylated modified-nucleotide-capped RNA provides a detection method for uses such as, but not limited to, detecting a nucleic acid sequence as part of a diagnostic assay or for assay of gene expression on an array or microarray.

In other specific embodiments of the method in which the modified cap nucleotide is a 2'-amino- or 3'-amino-modified deoxyguanosine-5'-triphosphate (i.e., 2'-amino-2'-dGTP or 3'-amino-3'-dGTP), the method further comprises the step of reacting the modified-nucleotide-capped RNA with a reactive detectable dye under conditions wherein the amino group is labeled with the dye under conditions wherein detectable modified-nucleotide-capped RNA is obtained. Thus, in some embodiments of the method in which the modified cap nucleotide is a 2'-amino- or 3'-amino-modified deoxyguanosine-5'-triphosphate (i.e., 2'-amino-2'-dGTP or 3'-amino-3'-dGTP), the method further comprises reacting the modified-nucleotide-capped RNA with a reactive detectable dye, such as, but not limited to, a fluorescent dye, a luminescent dye, a visible dye, or infrared fluorescent dye, such as selected from the group consisting of a N-hydroxysuccinimidyl ester of a Cy dye, a rhodamine dye, a fluorescein dye, and another dye that is known in the art. Thus, the method of the present invention also provides a way to label uncapped RNA comprising primary RNA transcripts or RNA having a 5'-diphosphate with a detectable dye.

In embodiments of the method in which the modified cap nucleotide is a 2'-azido- or 3'-azido-modified deoxyguanosine-5'-triphosphate (i.e., 2'-azido-2'-dGTP or 3'-azido-3'-dGTP), the method further comprises reacting the modified-nucleotide-capped RNA with a compound containing an alkynyl or acetylene moiety under conditions wherein the alkynyl moiety reacts with the azido group of the modified capped nucleotide under conditions wherein a derivatized modified-nucleotide-capped RNA is obtained. The reagent can provide a moiety for binding and capturing the modified-nucleotide-capped RNA or for labeling the modified-nucleotide-capped RNA with a detectable dye or it can provide another functionality. Detectable dyes having a reactive alkynyl group, such as, but not limited to, fluorescein dyes (Wang, Q et al., J. Am Chem. Soc. 125: 3192-3193, 2003) and rhodamine dyes (Speers, A E et al., J. Am Chem. Soc. 124: 4686-4687, 2003) are known in the art, which can be used in embodiments of kits and methods of the invention. In other embodiments, a detectable molecule having an alkynyl group is made using conventional synthesis techniques known in the art (e.g., see Breinbauer, R and Kohn, M, Chem Bio Chem 4: 1147-1149, 2003; Campbell, D A and Szardenings, A K, Curr. Opin. Chem. Biol. 7: 296-303, 2003), and the invention includes use of any such detectable molecules in the kits and methods of the invention. The invention also includes the use of techniques known in the art for coupling such detectable molecules having a reactive alkynyl group, such as, but not limited to fluorescein, rhodamine, or other dyes having an alkynyl group, to an azido substituent (e.g., see Wang, Q et al., J. Am Chem. Soc. 125: 3192-3193, 2003; Speers, A E et al., J. Am Chem. Soc. 124: 4686-4687, 2003; Breinbauer, R and Kohn, M, Chem Bio Chem 4: 1147-1149, 2003; Campbell, D A and Szardenings, A K, Curr. Opin. Chem. Biol. 7: 296-303, 2003), wherein the azido substituent is the 2' or 3' azido substituent of a modified cap nucleotide in a modified-nucleotide-capped RNA.

By way of example, but without limitation, in one embodiment, one hundred molar equivalents of modified-nucleotide-capped RNA, prepared from uncapped RNA comprising primary RNA transcripts or RNA having a 5'-diphosphate using a capping enzyme system and 2'-azido-dGTP as a modified cap nucleotide, is reacted with 117 equivalents of an alkynyl fluororescein in the presence of 50 equivalents of $CuSO_4$ and 100 equivalents of tris(carboxethyl)phosphine (TCEP) as described by Wang, Q et al. (J. Am. Chem. Soc. 125: 3192, 2003). The 2'-azido group of the modified cap nucleotide of the modified-nucleotide-capped RNA is thereby labeled with fluorescein dye. In another embodiment, one molar equivalent of modified-nucleotide-capped RNA, prepared from uncapped RNA derived from primary RNA using a capping enzyme system and 2'-azido-dGTP as a modified cap nucleotide, is reacted with 1.2 equivalents of an alkynyl rhodamine in the presence of 0.5 equivalent of $CuSO_4$ and one equivalent of TCEP as described by Speers, A E et al. (J. Am. Chem. Soc. 124: 4686, 2003). The 2'-azido group of the modified cap nucleotide of the modified-nucleotide-capped RNA is thereby labeled with rhodamine dye. The flourescein- or rhodamine-labeled modified-nucleotide-capped RNA provides a detection method for uses such as, but not limited to, detecting a nucleic acid sequence as part of a diagnostic assay or for assay of gene expression on an array or microarray, or for any of the other many applications known in the art where a labeled nucleic is useful.

In some embodiments of the method wherein the modified cap nucleotide has a 2' or 3' azido group, the modified-nucleotide-capped RNA consists of one or more prokaryotic mRNA molecules, including, but not limited to, all prokaryotic mRNA molecules in the sample. Since mRNA from a eukaryotic cell is already capped, prokaryotic mRNA in a sample that also contains eukaryotic mRNA is preferentially capped with a modified cap nucleotide by a capping enzyme system using a method and/or kit of the invention. In other embodiments, the modified-nucleotide-capped RNA consists of one or more uncapped RNAs comprising primary RNA transcripts or RNAs having a 5'-diphosphate from an in vitro transcription reaction, including one or more uncapped RNAs comprising primary RNA transcripts or RNAs having a 5'-diphosphate obtained from an RNA amplification reaction, such as an RNA amplification reaction described in the references cited above. In preferred embodiments the one or more uncapped RNAs comprise sense RNA. In some embodiments of this aspect of the invention, wherein the reagent has an affinity tag or capture moiety (e.g., a biotinylation reagent), the method further comprises: contacting the modified-nucleotide-capped RNA with the reagent, wherein the affinity tag is joined to the modified-nucleotide-capped RNA; and contacting the affinity tag-joined modified-nucleotide-capped RNA with an affinity tag binding molecule that has affinity for and binds to the reagent and that is directly or indirectly, attached to a surface, whereby the affinity tag-joined modified-nucleotide-capped RNA is isolated. Thus, in one embodiment, the method is used to isolate one or more prokaryotic mRNA molecules or one or more uncapped RNAs comprising primary RNA transcripts or RNAs having a 5'-diphosphate from an in vitro transcription reaction. In some embodiments, the one or more prokaryotic mRNA molecules is in a sample comprising both prokaryotic and eukaryotic mRNA. For example, but without limitation, in some embodiments, the prokaryotic mRNA is mRNA of a bacterial pathogen that is in the presence of mRNA of a eukaryotic host cell. In other embodiments, as a further example, the mRNA is mRNA from a nitrogen-fixing *Rhizobium* bacterium which is in the presence of mRNA from a legume root nodule. Since bacterial mRNA generally does not have a poly(A), which is commonly used to isolate eukaryotic mRNA, the method provides a novel method by which to isolate prokaryotic mRNA. Once prokaryotic mRNA is obtained using this embodiment of the method of the invention, the invention further comprises tailing the prokaryotic mRNA, such as by contacting the isolated mRNA with poly(A) polymerase under reaction conditions or using the method described by Sooknanan in U.S. Patent Application Nos. 20050153333, and further amplifying the prokaryotic mRNA using an RNA amplification method, such as a method cited herein above. In preferred embodiments, the RNA amplification reaction synthesizes sense RNA. In other embodiments, the RNA amplification reaction synthesizes anti-sense RNA.

D. Detailed Description of the Cap-Dependent Subtraction Method to Obtain Condition-Specific RNA In some embodiments, the method further comprises the steps of: annealing to the modified-nucleotide-capped RNA that is bound by the affinity-tag-binding molecule an excess of cDNA prepared from cells different from those used to obtain the modified-nucleotide-capped RNA; and treating the bound modified-nucleotide-capped RNA to which the cDNA is annealed with an RNase H, wherein modified-nucleotide-capped RNA to which the cDNA is annealed is digested and modified-nucleotide-capped RNA to which no cDNA is annealed is not digested and remains bound to the affinity-tag-binding molecule, thereby subtracting the modified-nucleotide-capped RNA that is homologous to the cDNA. Thus, in some embodiments, the invention provides a method for subtracting from the population of all mRNA molecules derived from a first cell that is of a first type or that is under a first condition those mRNA molecules that are also present in a second cell of a second type or that are under a second condition, thereby obtaining a population of mRNA molecules that are present only in the first cell, but absent in the second cell, the method comprising: (i) obtaining modified-nucleotide-capped RNA by contacting uncapped RNA comprising primary RNA transcripts or RNA having a 5'-diphosphate that is derived from the first cell with a capping enzyme system and a modified cap nucleotide consisting of a 2' and/or 3' deoxyguanosine-5'-triphosphate having a 2' or 3' amino, azido, or thiol (mercapto) substituent, under conditions wherein modified-nucleotide-capped RNA is synthesized from the mRNA from the first cell; (ii) reacting the 2' or 3' amino, azido, or thiol substituent with an affinity tag reagent that reacts therewith, thereby obtaining modified-nucleotide-capped RNA having the affinity tag on the amino, azido, or thiol substituent; (iii) preparing first-strand cDNA by reverse transcription of mRNA derived from the second cell using an RNA-dependent DNA polymerase or reverse transcriptase and a primer, such as, but not limited to an oligo(dT) or a random sequence primer; (iv) annealing the first-strand cDNA prepared from mRNA from the second cell to the modified-nucleotide-capped RNA from the first cell under hybridization conditions; (v) capturing the modified-nucleotide-capped RNA having the affinity tag on a surface by binding the affinity tag with an affinity-tag-binding molecule that is attached to a surface, thereby attaching the modified-nucleotide-capped RNA from the first cell to the surface; and (vi) treating the surface-attached modified-nucleotide-capped RNA from the first cell to which the cDNA from the second cell is annealed with RNase H, wherein the RNA to which the cDNA is annealed is digested, and subtracted modified-nucleotide-capped RNA that is attached to the surface is obtained. In some embodiments of the method, step #(iv) is performed prior to step #(v), whereas in other embodiments step #(iv) is performed after step #(v). In some embodiments of any of the above embodiments, the affinity tag having the reactive moiety is a biotinylation reagent having a reactive moiety consisting of an N-hydroxysuccinimidyl ester or an acylating or alkylating moiety for modified cap nucleosides having an amino substituent or an alkynyl moiety for modified cap nucleosides having an azido substituent; and the affinity-tag-binding molecule that is attached to a surface is avidin or streptavidin. In some embodiments, the method further comprises the step of treating the subtracted modified-nucleotide-capped RNA that is attached to the surface with a pyrophosphatase or decapping enzyme, thereby releasing the subtracted RNA consisting of RNA from the first cell from which RNA that is in common with RNA from the second cell has been removed or subtracted. In some embodiments, the pyrophosphatase is tobacco acid pyrophosphatase. In some embodiments, the decapping enzyme is yeast or human decapping enzyme. The invention also comprises kits for performing the above methods. In one embodiment, the kit comprises: (a) a capping enzyme system; (b) a modified cap nucleotide consisting of: (i) a 2' or 3' deoxyguanosine-5'-triphosphate comprising a 2' or 3' amino, azido, or thiol substituent, (ii) 6-thioguanosine-5'-triphosphate (i.e., 6 mercaptoguanosine-5'-triphosphate), or (iii) 6-thioguanine-2'- or 3'-deoxynucleoside-5'-triphosphate; (c) an affinity tag reagent; and (d) an affinity-tag-binding molecule that is attached to a surface. In some embodiments of the kit, affinity tag reagent consists of a biotin affinity tag having a reactive group consisting of, either, an N-hydroxysuccinimidyl ester or another acylating or alkylating moiety if the modified cap nucleotide has an amino substituent, or, an alkynyl moiety if the modified cap nucleotide has an azido substituent or, a maleimidyl moiety if the modified cap nucleotide has a thiol group; and the affinity-tag-binding molecule that is attached to a surface consists of avidin or streptavidin. In some of any of the above embodiments of kits, the kit further comprises RNase H. In addition, any of the above kits can also have one or more of the following reagents: a reverse transcriptase and/or a primer for preparing first-strand cDNA from mRNA from the second cell; and/or a hybridization solution for annealing the cDNA to the modified-nucleotide-capped RNA. The modified cap nucleotide in any of the above embodiments is selected from the group consisting of 2'-amino-2'-deoxyguanosine-5'-triphosphate, 3'-amino-3'-deoxyguanosine-5'-triphosphate, 2'-azido-2'-deoxyguanosine-5'-triphosphate, and 3'-azido-3'-deoxyguanosine-5'-triphosphate. The invention also comprises the subtracted RNA obtained using the above methods or kits.

The invention also provides kits and methods for labeling uncapped RNA comprising primary RNA transcripts or RNA having a 5'-diphosphate, whether such transcripts are obtained from a biological sample, such as a cell or tissue, or are synthesized in vitro, such as in an in vitro transcription or RNA amplification reaction, with a detectable molecule, such as, but not limited to, a visible, fluorescent, luminescent, or infrared fluorescent dye, or an enzyme that is detectable using a substrate, such as, but not limited to, a substrate that results in a visible, fluorescent, luminescent, or infrared fluorescent signal under enzymatic reaction conditions. For example, but without limitation, some embodiments provide a kit for indirect labeling comprising: a modified cap nucleotide selected from the group consisting of a guanine nucleoside-5'-triphosophate having 2' or 3' substituent consisting of an amino or an azido group; an affinity tag reagent; and an affinity-tag-binding molecule that is labeled with the detectable molecule. Some embodiments provide a method for indirect labeling of the uncapped RNA comprising primary RNA transcripts or RNA having a 5'-diphosphate comprising: (i) providing an uncapped RNA comprising primary RNA transcripts or RNA having a 5'-diphosphate, a capping enzyme system, a modified cap nucleotide having 2' or 3' substituent consisting of an amino or an azido group, an affinity tag reagent, and an affinity-tag-binding molecule that is labeled with the detectable molecule; (ii) contacting the uncapped RNA comprising primary RNA transcripts or RNA having a 5'-diphosphate with the capping enzyme system and the modified cap nucleotide under conditions wherein the uncapped RNA comprising primary RNA transcripts or RNA having a 5'-diphosphate is capped and a modified-nucleotide-capped RNA is synthesized; (iii) contacting the modified-nucleotide-capped RNA with the affinity tag having the reactive moiety under conditions wherein modified-nucleotide-capped RNA having a modified cap nucleotide that is joined to the affinity tag is obtained; and (iv) contacting the affinity tag that is joined to the modified cap nucleotide of the modified-nucleotide-capped RNA with the labeled affinity-tag-binding molecule under binding conditions, whereby the modified-nucleotide-capped RNA is labeled. The uncapped RNA comprising primary RNA transcripts or RNA having a 5'-diphosphate can be from a biological source or from an in vitro transcription reaction, including an RNA amplification reaction. In some embodiments, the uncapped RNA comprising primary RNA transcripts or RNA having a 5'-diphosphate is in a mixture that also includes other nucleic acids that are not uncapped RNA comprising primary RNA transcripts or RNA having a 5'-diphosphate. In some embodiments, the uncapped RNA comprising primary RNA transcripts or RNA having a 5'-diphosphate is mRNA, including prokaryotic mRNA. In some embodiments in which the primary RNA is from an RNA amplification reaction, the RNA amplification reaction is a sense RNA amplification reaction, such as, but not limited to a sense RNA amplification reaction referenced herein above. However, in some embodiments, the RNA amplification reaction used to obtain the primary RNA is an anti-sense RNA amplification reaction, such as, but not limited to an anti-sense RNA amplification reaction referenced herein above. In some embodiments of the kit or method, the affinity tag having the reactive moiety is a biotinylation reagent. In some embodiments of the kit or method wherein the 2' or 3' substituent of the modified cap nucleotide is an amino group, the reactive moiety is a biotinylation reagent. The biotinylation reagent can have any amine-reactive chemical moiety known in the art, such as, but not limited to, an acylating moiety, such as an N-hydroxysuccinimidyl (i.e., NHS) ester, or an alkylating moiety. In some embodiments of the kit or method wherein the 2' or 3' substituent of the modified cap nucleotide is an amino group, the affinity tag reagent is biotin-XX—NHS (also called biotin-LC-LC-NHS) or biotin-X—NHS (also called biotin-LC-NHS). In some embodiments of the kit or method wherein the 2' or 3' substituent of the modified cap nucleotide is an azido group, the reactive moiety of the affinity tag is a reactive alkynyl group which is capable of joining the affinity binding molecule to the azido group via a 1,3-dipolar cycloaddition; in embodiments of the method, the affinity tag is joined to the modified cap nucleotide of the modified-nucleotide-capped RNA via a 1,2,3-triazole moiety. In some embodiments of the kit or method wherein the affinity tag comprises biotin, the affinity-tag-binding molecule is labeled streptavidin or avidin that is labeled with a phycobiliprotein, a dye or any other detectable molecule known in the art.

The invention also comprises kits and methods for releasing the label from the labeled modified-nucleotide-capped RNA. For example, some embodiments of the kit additionally comprise a pyrophosphatase, such as, but not limited to tobacco acid pyrophosphatase, or a decapping enzyme, such as, but not limited to yeast or human decapping enzyme. Some embodiments of the method further comprise the step of contacting the labeled modified-nucleotide-capped RNA that is labeled with the pyrophosphatase, such as tobacco acid pyrophosphatase, or with the decapping enzyme, such as yeast or human decapping enzyme, whereby the labeled modified cap nucleotide is cleaved from the RNA and the label is released.

The invention also provides kits and methods for direct labeling of uncapped RNA comprising primary RNA transcripts or RNA having a 5'-diphosphate, whether uncapped RNA comprising primary RNA transcripts or RNA having a 5'-diphosphate is obtained from a biological sample, such as a prokaryotic cell, or a eukaryotic cell or tissue that is infected by a prokaryote, or are synthesized in vitro, such as in an in vitro transcription or RNA amplification reaction, with a detectable molecule, such as, but not limited to, a visible, fluorescent, luminescent, or infrared fluorescent dye. Some embodiments provide a kit for direct labeling of uncapped RNA comprising primary RNA transcripts or RNA having a 5'-diphosphate, the kit comprising: a modified cap nucleotide selected from the group consisting of a guanine nucleoside-5'-triphosophate having 2' or 3' substituent consisting of an amino or an azido group; and a detectable molecule having a reactive moiety. Some embodiments provide a method for direct labeling of the uncapped RNA comprising primary RNA transcripts or RNA having a 5'-diphosphate, the method comprising: (i) providing an uncapped RNA comprising primary RNA transcripts or RNA having a 5'-diphosphate, a capping enzyme system, a modified cap nucleotide having 2' or 3' substituent consisting of an amino or an azido group, and a detectable molecule having a reactive moiety; (ii) contacting the uncapped RNA comprising primary RNA transcripts or RNA having a 5'-diphosphate with the capping enzyme system and the modified cap nucleotide under conditions wherein the uncapped RNA comprising primary RNA transcripts or RNA having a 5'-diphosphate is capped and a modified-nucleotide-capped RNA is synthesized; and (iii) contacting the modified-nucleotide-capped RNA with the detectable molecule having a reactive moiety under conditions wherein the detectable molecule reacts with the modified cap nucleoside of the modified-nucleotide-capped RNA and the RNA is thereby labeled. The primary RNA can be from a biological source or from an in vitro transcription reaction, including an RNA amplification reaction. In preferred embodiments, the RNA amplification reaction used to obtain the primary RNA is a sense RNA amplification reaction, such as, but not limited to a sense RNA amplification reaction referenced herein above. However, in some embodiments, the RNA amplification reaction used to obtain the primary RNA is an anti-sense RNA amplification reaction, such as, but not limited to an anti-sense RNA amplification reaction referenced herein above. In some embodiments of the kit or method wherein the 2' or 3' substituent of the modified cap nucleotide is an amino group, the reactive moiety is an acylating group, such as an N-hydroxysuccinimidyl (i.e., NHS) ester, or an alkylating group. A wide variety of detectable molecules having a reactive group that can react with the 2' or 3' amino substituent of the modified cap nucleotide are known in the art, including, but not limited to visible, fluorescent, luminescent, and infrared fluorescent dyes, such as Cy dyes, fluorescein dyes, rhodamine dyes and the like, and the invention includes the use of any such detectable molecule in the kits or methods of the invention. In some embodiments of the kit or method wherein the 2' or 3' substituent of the modified cap nucleotide is an azido group, the reactive moiety of the detectable molecule is a reactive alkynyl group which is capable of joining the detectable molecule to the azido group via a 1,3-dipolar cycloaddition; in embodiments of the method, the detectable molecule is joined to the modified cap nucleotide of the modified-nucleotide-capped RNA via a 1,2,3-triazole moiety. Dye molecules having a reactive moiety consisting of an alkynyl group, which can be used for the kits and methods of the present invention, are known in the art (e.g., see Breinbauer, R and Kohn, M, Chem Bio Chem 4: 1147-1149, 2003 and references therein), and those with knowledge in the art will understand how to readily obtain or make a dye molecule having a reactive alkynyl group using what is known. In preferred embodiments, the reactive detectable dye does not label greater than ten percent of RNA molecules that do not have the modified cap nucleoside with the respective amino, azido, or thiol substituent. More preferably, the reactive detectable dye labels less than five percent or less than one percent of the RNA molecules that do not have the modified cap nucleoside with the respective amino, azido, or thiol group. Most preferably, the reactive detectable dye labels less than one percent of the RNA molecules that do not have the modified cap nucleoside with the respective amino, azido, or thiol group.

The invention also comprises kits and methods for releasing the label from the labeled modified-nucleotide-capped RNA. For example, some embodiments of the kit additionally comprise a pyrophosphatase, such as, but not limited to tobacco acid pyrophosphatase, or a decapping enzyme, such as, but not limited to yeast or human decapping enzyme. Some embodiments of the method further comprise the step of contacting the labeled modified-nucleotide-capped RNA with a pyrophosphatase, such as tobacco acid pyrophosphatase, or a decapping enzyme, such as, but not limited to yeast or human decapping enzyme, whereby the labeled modified cap nucleotide is cleaved from the RNA and the label is removed.

The kits and methods for labeling uncapped RNA comprising primary RNA transcripts or RNA having a 5'-diphosphate, and in some embodiments, for releasing the labeled modified cap nucleotide from labeled modified-nucleotide-capped RNA can be used as assays for detecting the presence and quantifying the amount of one or more uncapped RNAs comprising primary RNA transcripts or RNA having a 5'-diphosphate in a sample. Thus, some embodiments of the method additionally comprises the step of measuring the amount of label attached to the modified-nucleotide-capped RNA or measuring the amount of label released from the modified-nucleotide-capped RNA in a sample upon treatment with a pyrophosphatase or a decapping enzyme, thereby detecting and/or quantifying the amount of modified-nucleotide-capped RNA present in the sample. In some embodiments, the labeled modified-nucleotide-capped RNA is used as labeled target for hybridization to microarrays of oligonucleotides or polynucleotides corresponding to genes and/or transcripts for a particular cell, tissue or organism (e.g., Affymetrix or Illumina microarrays).

Cap-Labeling: Methods and Kits for Labeling Uncapped RNA

Still other embodiments of the invention provide a cap-labeling method for labeling uncapped RNA comprising primary RNA or RNA having a 5'-diphosphate in a sample, the method comprising: (i) providing a sample comprising the uncapped RNA; a capping enzyme system; a modified cap nucleotide, wherein the modified cap nucleotide contains a chemical binding moiety to facilitate binding to an affinity-tag-binding molecule; and the affinity-tag-binding molecule to which a detectable label is attached; (ii) contacting the uncapped RNA with the capping enzyme system and the modified cap nucleotide under conditions wherein modified-nucleotide-capped RNA is synthesized; (iii) contacting the modified-nucleotide-capped RNA with reagents and under conditions that facilitate binding of the modified cap nucleotide to the affinity-tag-binding molecule to which the detectable label is attached; and (iv) contacting the modified-nucleotide-capped RNA to the affinity-tag-binding molecule to which the detectable label is attached, thereby labeling the modified-nucleotide-capped RNA. In some embodiments of this cap-labeling method, the chemical binding moiety of the modified cap nucleotide provided in step (i) comprises an affinity tag that is capable of binding the affinity-tag-binding molecule to which the detectable label is attached and step (iii) comprises incubating the modified-nucleotide-capped RNA in a buffer and under conditions that facilitate binding of the modified cap nucleotide to the affinity-tag-binding molecule to which the detectable label is attached. In some other embodiments of the cap-labeling method, the modified cap nucleotide provided in step (i) contains a chemical binding moiety comprising an amino, an azido, or a thiol group and step (iii) comprises contacting the modified-nucleotide-capped RNA with an affinity tag reagent under conditions wherein the affinity tag is chemically joined to the chemical binding moiety, and further incubating the modified-nucleotide-capped RNA in a buffer and under conditions that facilitate binding of the modified cap nucleotide to the affinity-tag-binding molecule to which the detectable label is attached. Thus, one embodiment of the invention comprises a kit for cap-labeling, the kit comprising: (i) a capping enzyme system; (ii) a modified cap nucleotide, wherein the modified cap nucleotide contains a chemical binding moiety to facilitate binding to an affinity-tag-binding molecule; and (iii) the affinity-tag-binding molecule to which a detectable label is attached. In some embodiments of the kit for cap-labeling, the chemical binding moiety of the modified cap nucleotide comprises an affinity tag that is capable of binding the affinity-tag-binding molecule. In other embodiments of the kit for cap-labeling, the chemical binding moiety of the modified cap nucleotide comprises an amino, an azido, or a thiol group, and the kit additionally comprises: (iv) an affinity tag reagent that is capable of reacting with the respective amino, azido, or thiol group of the modified cap nucleotide, thereby chemically joining the affinity tag to the chemical binding moiety of the modified cap nucleotide. In preferred embodiments of the methods and kits for cap-labeling, the affinity tag is biotin and the affinity-tag-binding molecule is streptavidin or avidin.

The biotinylated modified-nucleotide-capped RNA is labeled by binding to streptavidin or avidin that is covalently attached to a detectable molecule, including, without limit, a visible, fluorescent, luminescent, or infrared fluorescent molecule, such as, but not limited to, phycoerythrin or another phycobiliprotein, fluorescein, rhodamine, Cy3, Cy5, or an Alexa dye, or another dye, or to streptavidin or avidin that is covalently attached to an enzyme that is detectable using a substrate, such as, but not limited to, a substrate that results in a visible, fluorescent, luminescent, or infrared fluorescent signal under enzymatic reaction conditions. The binding of the labeled streptavidin or avidin affinity-tag-binding molecule to the biotinylated modified-nucleotide-capped RNA provides a detection method for uses such as, but not limited to, detecting a nucleic acid sequence as part of a diagnostic assay or for assay of gene expression on an array or microarray.

In some embodiments, the method for cap-labeling further comprises the step of: (v) contacting the modified-nucleotide-capped RNA that is bound to the surface with a protein or biochemical reagent under conditions wherein the triphosphate between the modified cap nucleotide and the 5'-penultimate nucleotide of the modified-nucleotide-capped RNA is cleaved, thereby de-capping the modified-nucleotide-capped RNA and releasing the label therefrom. In some preferred embodiments, the protein or biochemical reagent that cleaves the triphosphate is a pyrophosphatase or decapping enzyme. In some preferred embodiments, the protein or biochemical reagent that cleaves the triphosphate is selected from the group consisting of tobacco acid pyrophosphatase, *Saccharomyces cerevisiae* decapping enzyme, and human decapping enzyme. Thus, in some embodiments of the kit for cap-labeling, the kit additionally comprises: (v) a protein or biochemical reagent that is capable of specifically cleaving the triphosphate in the modified-nucleotide-capped RNA between the modified cap nucleotide and the 5'-penultimate nucleotide of the modified-nucleotide-capped RNA without cleaving other positions in the modified-nucleotide-capped RNA. In some preferred embodiments of the kit, the protein or biochemical reagent that is capable of specifically cleaving the triphosphate selected from the group consisting of tobacco acid pyrophosphatase, *Saccharomyces cerevisiae* decapping enzyme, and human decapping enzyme.

In still another embodiment for labeling uncapped RNA, the basic method of the invention is a direct method for labeling uncapped RNA, the method comprising: (i) providing a capping enzyme system, and a modified cap nucleotide; and (ii) contacting the uncapped RNA with a capping enzyme system and a modified cap nucleotide under conditions wherein a modified-nucleotide-capped RNA is synthesized. In this embodiment, the modified cap nucleotide itself comprises a guanine nucleoside-5'-triphosphate wherein the detectable label is joined to a position comprising the 2'- or 3'-amino, azido, or thiol group of the sugar, or to the O6-position of the guanine base, or to the S6-position of the thioguanine base. A kit of this embodiment comprises: (i) the capping enzyme system; and (ii) the modified cap nucleotide comprising the detectable label.

In specific embodiments of the method in which the modified cap nucleotide comprises a 2'- or 3'-amino-, azido-, or mercapto-modified deoxyguanosine-5'-triphosphate (e.g., 2'-amino-2'-dGTP, 3'-amino-3'-dGTP, 2'-amino-2',3'-ddGTP, 3'-amino-2',3'-ddGTP, 2'-azido-2'-dGTP, 3'-azido-3'-dGTP, 2'-azido-2',3'-ddGTP, 3'-azido-2',3'-ddGTP, 2'-mercapto-2'-dGTP, 3'-mercapto-3'-dGTP, 2'-mercapto-2',3'-ddGTP, 3'-mercapto-2',3'-ddGTP), the method further comprises the step of reacting the modified-nucleotide-capped RNA with a reactive detectable dye under conditions wherein the amino, azido, or mercapto group is labeled with the dye under conditions wherein detectable modified-nucleotide-capped RNA is obtained. Thus, in some embodiments of the method in which the modified cap nucleotide is an amino-modified deoxyguanosine-5'-triphosphate, the method further comprises reacting the modified-nucleotide-capped RNA with a reactive detectable dye, such as, but not limited to, a fluorescent dye, a luminescent dye, a visible dye, or infrared fluorescent dye, such as selected from the group consisting of a N-hydroxysuccinimidyl ester of a Cy dye, a rhodamine dye, a fluorescein dye, and another dye that is known in the art. In some embodiments wherein the modified cap nucleotide is an azido-modified deoxyguanosine-5'-triphosphate, the method further comprises reacting the modified-nucleotide-capped RNA with a detectable dye having a reactive alkyne moiety. In some embodiments wherein the modified cap nucleotide is a mercapto-modified deoxyguanosine-5'-triphosphate, the method further comprises reacting the modified-nucleotide-capped RNA with a detectable dye having a reactive moiety, such as a maleimidyl moiety. Thus, the method of the present invention also provides a way to label uncapped RNA comprising primary RNA transcripts or RNA having a 5'-diphosphate with a detectable dye. Any detectable molecule known in the art can be used in the present invention. Examples of some detectable molecules which can be used are described in "Handbook of Fluorescent Probes and Research Products", Ninth Edition, by R. P. Hoagland, Molecular Probes, Inc.

Kits

The present invention also provides kits comprising a capping enzyme system and a modified cap nucleotide of the present invention. Additionally, the present invention provides kit having one or more components useful, sufficient, and/or necessary for carrying out any of the methods described herein. In some embodiments, the kit comprises poxvirus capping enzyme and a modified cap nucleotide. In some embodiments, the kit comprises vaccinia virus capping enzyme system and a modified cap nucleotide of the present invention. Some embodiments of the kit comprise a vaccinia virus capping enzyme system purified from vaccinia virions, whereas other embodiments of the kit comprise a vaccinia virus capping enzyme system from a recombinant source. The present invention includes embodiments of the kit, wherein the modified cap nucleotide is a 2'- or 3'-modified nucleotide. In some embodiments of the kit of the invention, the modified cap nucleotide is a guanine nucleoside-5'-triphosphate wherein the 2'- or 3'-position of the ribose sugar moiety is substituted with a group such as, but not limited to, an O-methyl group, an amino group, an azido group or a fluorine group. By way of example, but without limitation, in some embodiments of the kit, the modified cap nucleotide is selected from the group consisting of: guanine 3'-O-methyl-ribonucleoside-5'-triphosphate; guanine 2'-O-methyl-ribonucleoside-5'-triphosphate; guanine 2'-amino-2'-deoxyribonucleoside-5'-triphosphate; guanine 3'-amino-3'-deoxyribonucleoside-5'-triphosphate; guanine 2'-azido-2'-deoxyribonucleoside-5'-triphosphate; guanine 3'-azido-3'-deoxyribonucleoside-5'-triphosphate; or guanine 2'-fluoro-2'-deoxyribonucleoside-5'-triphosphate. In some embodiments of the kit, the modified cap nucleotide is guanine 2'-deoxyribonucleoside-5'-triphosphate or guanine 3'-deoxyribonucleoside-5'-triphosphate.

In some embodiments of the kit, the modified cap nucleotide is a guanine nucleoside-5'-triphosphate wherein the base is modified. By way of example, but without limitation, in some embodiments of the method, the modified cap nucleotide is selected from the group consisting of $N^1$-methylguanine-ribonucleoside-5'-triphosphate and $O^6$-methylguanine-ribonucleoside-5'-triphosphate. The kit of the invention is not limited to these modified cap nucleotides. The modified cap nucleotide in the kit can be any modified guanine nucleoside-5'-triphosphate that is compatible with the enzymatic activities of the capping enzyme systems of the present invention.

In some embodiments, the kit further comprises S-adenosyl-methionine or S-adenosyl-ethionine. In some embodiments, the co-factor (e.g., S-adenosyl-methionine) is used with an enzyme having guanine-7-methyltransferase activity, such as, but not limited to, the guanine-7-methyltransferase that comprises the vaccinia capping enzyme system.

In some embodiments, the kit further comprises an mRNA (nucleoside-2'-O—) methyltransferase. In some embodiments, the mRNA (nucleoside-2'-O—) methyltransferase activity is encoded by poxvirus DNA. In some embodiments, the mRNA (nucleoside-2'-O—) methyltransferase activity is encoded by vaccinia virus DNA. In such embodiments, the kit can also further comprise S-adenosyl-methionine.

In some embodiments, the kit further comprises a poly(A) polymerase and other reagents, including ATP, for polyadenylation of RNA.

In some embodiments, the kit further comprises a cell-free extract for in vitro translation. In some embodiments, the cell-free extract is selected from the group consisting of an animal, a plant, a yeast, and a human cell-free extract. In some embodiments, the cell-free extract is selected from the group consisting of a rabbit reticulocyte lysate, a wheat germ lysate, a *drosophila* embryo lysate, and a human reticulocyte lysate, wherein the human reticulocytes are derived from human stem cells in culture. In some embodiments, the human reticulocytes are prepared from embryonic stem cells. In other embodiments, the human reticulocytes are prepared from adult stem cells from a patient with a condition. In other embodiments, the human reticulocytes are prepared from adult stem cells from a donor.

In some embodiments, the kit further comprises reagents for transformation or transfection of a eukaryotic cell. Thus, in some embodiments, the kit further comprises reagents for transfection methods, such as, but not limited to, cationic lipids for lipid-mediated transfection, or solutions for electroporation, or calcium phosphate transfection. In preferred embodiments, the kit further comprises reagents for transformation or transfection of a dendritic cell, a macrophage cell, an immune system cell, an epithelial cell, or an artificially generated APC.

In some embodiments wherein the modified cap nucleotide is 2'-amino-2'-dGTP or 3'-amino-3'-dGTP, the kit further comprises a biotinylation reagent. By way of example, but without limitation, in some embodiments, the biotinylation reagent is biotin-X—X—NHS or biotin-X—NHS. In some such embodiments, the kit can further comprise streptavidin or avidin. In some embodiments, the streptavidin or avidin is attached to a surface. In other such embodiments, the kit can further comprise a reactive fluorescent, infrared fluorescent, visible, or other detectable dye, such as, but not limited to, an N-hydroxysuccinimidyl ester of a Cy dye, a fluorescein dye, a rhodamine dye or an Alexa dye. In other embodiments, the reagent compound in the kit can comprise an affinity tag other than biotin that has a moiety for binding the modified-nucleotide-capped RNA with an affinity-tag-binding molecule or a detectable dye for labeling the modified-nucleotide-capped RNA with the dye, or it can provide another functionality. In some embodiments, the kit additionally comprises an affinity-tag-binding molecule, which is either free or attached to a surface.

In some embodiments wherein the modified cap nucleotide in the kit is 2'-azido-2'-dGTP or 3'-azido-3'-dGTP, the kit further comprises a reagent compound containing an alkynyl or acetylene moiety that can react with the azido group of the modified capped nucleotide, thereby forming a modified-nucleotide-capped RNA that is derivatized with the reagent compound. The reagent compound can comprise an affinity tag having a moiety for binding the modified-nucleotide-capped RNA with an affinity-tag-binding molecule or a detectable dye for labeling the modified-nucleotide-capped RNA with the dye, or it can provide another functionality. In some embodiments, the kit additionally comprises an affinity-tag-binding molecule, which is either free or attached to a surface. In other embodiments, the kit can further comprise a reactive (e.g., having an alkynyl group) fluorescent, infrared fluorescent, visible, or other detectable dye, such as, but not limited to, a Cy dye, a fluorescein dye, a rhodamine dye or an Alexa dye having an alkynyl group.

In some embodiments in which the kit comprises a modified cap nucleotide other than an amino- or azido-modified dGTP, the kit further comprises a reagent compound that has a reactive moiety or an affinity binding molecule, which moiety or affinity binding molecule can react with or bind with the modified capped nucleotide under conditions wherein a derivatized modified-nucleotide-capped RNA is obtained. The reagent compound can also provide another moiety for binding and capturing or for labeling the modified-nucleotide-capped RNA with a detectable dye, or it can provide another functionality.

In some such embodiments, the kit can further comprise streptavidin or avidin, which is either free or attached to a surface. In other such embodiments, the kit can further comprise a reactive detectable dye, such as, but not limited to, a fluorescent dye selected from the group consisting of a N-hydroxysuccinimidyl ester of a Cy dye.

In some embodiments, the kit comprises an RNase. In some embodiments the RNase is RNase I or RNase A. In some embodiments, the kit further comprises an RNase H. In some embodiments, the kit comprises a buffer. In some embodiments, the kit comprises reagents for in vitro transcription of RNAs. In some embodiments, the kit comprises reagents for using the capped RNA of the present invention in RNA vaccine applications (e.g., buffers, cells, transfection reagents, control reagents, etc.).

In some embodiments, the kit further comprises a cell (e.g., a dendritic or macrophage cell) that is transformed or transfected with modified-nucleotide-capped RNA having either a cap 0 or a cap I structure, which modified-nucleotide-capped RNA is preferably also polyadenylated. In some embodiments the cell has been transformed or transfected with modified-nucleotide-capped RNA that is prepared using RNA from an in vitro transcription reaction or an RNA amplification reaction, and then capped with a modified cap nucleotide, and polyadenylated using methods of the present invention.

In some embodiments, the present invention provides a kit for catalyzing formation of a modified-nucleotide-capped RNA comprising: a polypeptide sequence for full-length vaccinia virus capping enzyme, or an enzymatically active portion thereof, and a modified cap nucleotide. In some embodiments, the kit additionally comprises one or more of a ribonuclease inhibitor, an amino acid mixture, ATP, S-adenosylmethionine for methylation (e.g., of guanine residues), and/or magnesium salt.

In some embodiments, the present invention provides a kit for producing protein (e.g., from a DNA template via sequential transcription, catalyzed formation of a modified-nucleotide-capped RNA, and translation), the kit comprising: (a) a polypeptide sequence for vaccinia virus capping enzyme, and a modified cap nucleotide; (b) a cell-free cell extract (e.g., eukaryotic cell-free extract from plant, animal or yeast cells); (c) ribonucleotide triphosphates; and (d) RNA polymerase. In some embodiments, the kit is configured to generate RNA from any DNA template. In some embodiments, the DNA template is downstream of a T7, T3 or SP6 RNA polymerase promoter. In some embodiments, the DNA template includes sequence in a linearized plasmid, cDNA, a double-stranded oligo, or PCR product.

In some embodiments, the present invention provides a kit for producing protein (e.g., from an uncapped RNA template via coupled catalyzed formation of modified-nucleotide-capped RNA and translation), the kit comprising: (a) a polypeptide sequence for vaccinia virus capping enzyme, and a modified cap nucleotide; and (b) cell-free extract (e.g., eukaryotic cell-free extract from plant, animal or yeast cells). In some embodiments, the cell-free extract is rabbit reticulocyte lysate. In some embodiments, the cell-free extract is *drosophila* embryo extract. In some embodiments, the cell-free extract is wheat germ extract. In some embodiments, the cell-free extract is a human reticulocyte lysate. In some embodiments, the cell-free extract is synthetic (e.g., not eukaryotic cell-derived).

In some embodiments, all kit components are present within a single container (e.g., vial or tube). In some embodiments, each kit component is located in a single container (e.g., vial or tube). In some embodiments, one or more kit components are located in a single container (e.g., vial or tube) with other components of the same kit being located in a separate container (e.g., vial or tube). For example, in some embodiments, a kit comprises a container comprising a solution of modified cap nucleotide and one or more other containers, wherein one of the other containers comprises a poxvirus capping enzyme. In some embodiments, a kit comprises instructions for use of the kit. In some embodiments, a kit of the present invention comprises reagents (e.g., poly(A) polymerase and/or ATP) for polyadenylation of RNA. In some embodiments, a kit of the present invention comprises ribonucleoside 5'-triphosphates (e.g., ATP, CTP, GTP, or UTP (e.g., each in their own container or, as a premixed solution of all four).

In some embodiments, a kit of the present invention comprises a solution of the modified cap nucleotide. In some embodiments, a kit comprises a buffer. In some embodiments, a kit of the present invention comprises or is used with biotin-labeled nucleoside triphosphates and/or aminoallyl-labeled nucleoside triphosphates. In some embodiments, a kit of the present invention comprises a radiolabeled agent (e.g., $^3$H-methyl-S-adenosyl-L-methionine, $^{14}$C-methyl-S-adenosyl-L-methionine, or $\alpha$-$^{32}$P-GTP). In some embodiments, a kit of the present invention comprises an RNase inhibitor. In some embodiments, a kit of the present invention may include a DNase (e.g., DNase I, e.g., RNase-free DNase I, including DNase I from bovine pancreas). In some embodiments, a kit comprises components for an RNA amplification reaction (e.g., for amplification of mRNA from laser capture microdissection or "LCM" samples or from other samples of limited quantity).

The uncapped RNAs comprising primary RNA transcripts or RNAs having a 5'-diphosphate that are capped using a method or kit of the invention can be of any length. For example, in some embodiments, RNA capped by the compositions and methods of the present invention is 0-0.1 kB in length. In some embodiments, the RNA is between 0.1-0.5 kB in length. In some embodiments, the RNA is between 0.5-1.0 kB in length. In some embodiments, the RNA is between 1-2 kB in length. In some embodiments, the RNA is between 2 kB-10 kB in length. In some embodiments, the RNA is between 0.1 kB-10 kB in length. In some embodiments, the RNA is longer than 10 kB in length.

In some embodiments, the present invention provides nucleic acids encoding one or more enzymatic activities of a capping enzyme system, together with plasmids, vectors and/or cells for genetic complementation assays in order to identify, screen, correct and/or monitor a genetic defect in the capping pathway. In some embodiments, the nucleic acid sequence encodes poxvirus capping enzyme and also comprises vector expression sequences and/or regulatory element sequences. In some embodiments, the nucleic acid sequence encodes vaccinia virus capping enzyme and also comprises vector expression sequences and/or regulatory element sequences. In some embodiments, the nucleic acid encoding one or more activities of a capping enzyme system (e.g., a nucleic acid sequence that encodes vaccinia virus capping enzyme) are in an artificial transposon, such as an EZ-Tn5 transposon or a HyperMu transposon. In some embodiments, said artificial transposon comprises a synaptic complex between the transposon and a transposase that recognizes the transposon recognition sequences in said transposon (i.e., a "transposome"), such as an EZ-Tn5 or HyperMu transposome.

All publications and patents mentioned in the above specification are herein incorporated by reference. Various modifications and variations of the described compositions and methods of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the present invention.

EXAMPLES

The following examples are provided in order to demonstrate and further illustrate certain preferred embodiments and aspects of the present invention and are not to be construed as limiting the scope thereof.

A. Methods
Method 1. Reaction Mixture for Evaluation of Nucleoside-5'-Triphosphates as Substrates for Capping Enzyme: Synthesis of Capped RNA Having a Cap 0 Structure, but Lacking an N$^7$-Methyl Group in the Cap Nucleotide In order to evaluate the ability of a nucleoside-5'-triphosphate to be used as a modified cap nucleotide substrate by capping enzyme for synthesis of modified-nucleotide-capped RNA having a cap 0 structure lacking a 7-methylguanine in the cap nucleotide, capping enzyme reactions were prepared that contained: 1 μg of a 51-base primary RNA transcript (prepared by in vitro transcription of a T7 promoter-containing double-stranded DNA template using a AmpliScribe™ T7-Flash™ Transcription Kit according to the protocol provided with the kit from EPICENTRE Biotechnologies, Madison, Wis., USA) as substrate; 1× Capping Enzyme Buffer (50 mM Tris-HCl, pH 8.0; 6 mM KCl; 1.25 mM $MgCl_2$); 1 mM of each respective nucleoside-5'-triphosphate tested; 0.1 μg of vaccinia capping enzyme (10 GTPase units); and water to a final reaction volume of 20 μl. One GTPase unit catalyzes release of one nanomole of inorganic phosphate from GTP in 10 minutes at 37° C. under standard assay conditions.

Method 2. Reaction Mixture for Evaluation of Nucleoside-5'-Triphosphates as Substrates for Capping Enzyme Systems for Synthesis of Capped RNA or Modified-Nucleotide-Capped RNA Having a Cap 0 Structure with an $N^7$-Methyl Group in the Cap Nucleotide In order to evaluate the ability of a nucleoside-5'-triphosphate to be used as a modified cap nucleotide substrate by a capping enzyme system for synthesis of modified-nucleotide-capped RNA having a cap 0 structure with a 7-methyl group in the base of the cap nucleotide, capping enzyme reactions were prepared as described in Method 1 above, except that the reaction mixture additionally contained: 0.25 μCi ($^{14}$C-methyl)-S-adenosyl-L-methionine (specific activity: 55 Ci/mmol).

Method 3. Capping Enzyme System Reactions.

Unless otherwise stated, each capping enzyme reaction prepared as described in Method 1 was incubated at 37° C. for 30 minutes. Unless otherwise stated, each capping enzyme reaction prepared as described in Method 2 was incubated at 37° C. for 2 hours. All reactions were stored at −20° C. until analyzed.

Method 4. PAGE Analysis of Results of Capping Enzyme System and Other Reactions.

An aliquot corresponding to 0.1 μg of RNA (i.e., 2 μl) from each completed capping enzyme reaction was subjected to denaturing polyacrylamide gel electrophoresis on a 20% polyacrylamide, 8 M Urea, 1×TBE gel. The gel was run at 510 volts for 4 hours, then stained by ethidium bromide and photographed.

Method 5. Autoradiography of PAGE Gels.

When assays using radioactive S-adenosyl-L-methionine were performed according to Method 2 or Method 7, the PAGE gel was subsequently dried down and exposed to film for 7-10 days in order to visualize radioactively-labeled reaction products by autoradiographic detection.

Method 6. Preparation of Modified-Nucleotide-Capped RNA Having a Modified Cap Nucleotide with an $N^7$-Methyl Group as Substrates for Synthesis by mRNA (Nucleoside-2'-O—) Methyltransferase of Modified-Nucleotide-Capped RNA Having a Cap I Structure.

In order to assay for the ability of a modified-nucleotide-capped RNA (or a standard unmodified $m^7$G-capped RNA control) having a cap 0 structure, wherein the cap nucleotide has a methyl group on the $N^7$-position of the nucleic acid base, to be converted to a modified-nucleotide-capped RNA having a cap I structure (i.e., having a 2'-O-methyl group on the penultimate nucleotide at the 5-end), 6 μg of a 51-base primary RNA transcript was capped in the presence of either GTP or a modified nucleoside-5'-triphosphate selected from the group consisting of $N^1$-methyl-GTP, $O^6$-methyl-GTP, 3'-OMe-GTP, 2'-OMe-GTP, 2'-dGTP, 2'-F-dGTP, 2'-amino-dGTP, and 2'-azido-dGTP in a capping enzyme reaction mixture as described in Method 1, except that the capping enzyme reaction additionally contained 1 mM unlabeled S-adenosyl-L-methionine. The reaction mixture was incubated at 37° C. for two hours. The reaction products were analyzed as described in Method 4. The 51-base primary RNA transcript was converted by the capping enzyme system into a 52-base capped RNA, as determined by PAGE analysis of the reaction products using 51-base and 52-base size marker electrophoresis standards. The reaction containing capped RNA was stored at −20° C. until used.

Method 7. Reaction Mixture for Evaluation of Modified-Nucleotide-Capped RNAs Having Different Modified Cap Nucleotides as Substrates for mRNA (Nucleoside-2'-O—) Methyltransferase In order to evaluate the ability of a modified-nucleotide-capped RNA having a cap 0 structure to serve as a substrate for 2'-O-methylation of the penultimate nucleotide at the S-end, two μg of each 52-base modified-nucleotide-capped RNA (or the unmodified $m^7$G-capped RNA control), prepared as described in Method 6, was incubated in a reaction mixture consisting of 1× Reaction Buffer (50 mM Tris-HCl, pH 8.0; 6 mM KCl; 1.25 mM $MgCl_2$) with 0.220-0.275 μg of vaccinia mRNA (nucleoside-2'-O—) methyltransferase which additionally contained 0.25 μCi ($^{14}$C-methyl)-S-adenosyl-L-methionine (specific activity: 55 Ci/mmol).

Method 8. Assay for Removal of a Modified Cap Nucleotide from a Modified-Nucleotide-Capped RNA by Tobacco Acid Pyrophosphatase.

Two μg of a 52-base unmodified $m^7$G-capped RNA or a modified-nucleotide-capped RNA obtained in Method 6 was treated with tobacco acid pyrophosphatase (TAP) in 1× reaction buffer as described by the supplier (EPICENTRE Biotechnologies, Madison, Wis., USA). The TAP-treated reaction product was analyzed by denaturing polyacrylamide gel electrophoresis on a 20% polyacrylamide, 8 M Urea, 1×TBE gel. The gel was run at 510 volts for 4 hours, then stained by ethidium bromide and photographed.

Method 9. Polyadenylation of Modified-Nucleotide-Capped RNA Using Poly(A) Polymerase.

One μg of a 52-base unmodified $m^7$G-capped RNA or a modified-nucleotide-capped RNA obtained as described in Method 6 is incubated in the presence of 4 units of A-Plus™ Poly(A)-Polymerase and 1 mM ATP in 1× reaction buffer (50 mM Tris-HCL, pH 8.0, 250 mM NaCl, and 10 mM $MgCl_2$, as described by the supplier (EPICENTRE Biotechnologies, Madison, Wis., USA). The polyadenylated reaction product is analyzed by denaturing polyacrylamide gel electrophoresis on a 20% polyacrylamide, 8 M Urea, 1×TBE gel. The gel is run at 510 volts for 4 hours, and then is stained by ethidium bromide and photographed.

Method 10. Synthesis of Modified-Nucleotide-Capped Polyadenylated RNAs with a Cap 0 or a Cap I Structure and Control Capped RNAs from a Primary Transcript Obtained by In Vitro Transcription of a DNA Template Comprising a Gene Located Downstream of a T7 RNA Polymerase Promoter.

pRL-SV40 DNA (Promega, Madison, Wis., USA) was digested to completion with Xba I endonuclease (New England BioLabs, Ipswich, Mass., USA) as per manufacturer's instructions. The resultant linear double-stranded DNA contains the coding region (gene) for *Renilla* luciferase downstream of a phage T7 RNA polymerase promoter. The DNA was used as a template for in vitro transcription using an AmpliScribe™ T7-Flash™ Transcription Kit (EPICENTRE Biotechnologies, Madison, Wis., USA) as per manufacturer's instructions to produce an ~953-base run-off RNA transcript. One hundred and twenty micrograms (120 μg) of purified *Renilla* luciferase RNA was poly(A)-tailed using an A-Plus™ Poly(A)-Tailing Kit (EPICENTRE Biotechnologies, Madison, Wis., USA) as per manufacturer's instructions except the total reaction volume was 200 µl and the incubation was carried out for 60 minutes. Primary RNA transcripts having poly(A)-tails that were estimated to be 150-200 A's long were obtained based on gel analysis using size standards. A 7.5-µg sample of the purified T7-transcribed poly(A)-tailed RNA primary transcript of the *Renilla* luciferase gene was then capped in a reaction mixture containing 1 mM of one of each of the nucleoside-5'-triphosphates tested in 1× capping buffer (50 mM Tris-HCl, pH 8.0; 6 mM KCl; 1.25 mM $MgCl_2$) with 1 mM S-adenosyl-methionine (SAM) and 0.2 µg of vaccinia capping enzyme (20 GTPase units) (EPICENTRE Biotechnologies, Madison, Wis., USA) for 3 hours at 37° C. This treatment produces capped poly(A)-tailed RNA having a cap 0 structure on the 5'-end. Similarly, in other reactions, a 7.5-µg sample of the purified T7-transcribed poly(A)-tailed RNA primary transcript of the *Renilla* luciferase gene was capped in a reaction mixture containing 1 mM of one of each respective nucleoside-5'-triphosphate tested in 1× capping buffer (50 mM Tris-HCl, pH 8.0; 6 mM KCl; 1.25 mM $MgCl_2$) and 1 mM S-adenosyl-methionine (SAM) and 0.2 µg of vaccinia mRNA (nucleoside-2'-O—)methyltransferase (EPICENTRE Biotechnologies, Madison, Wis., USA) for 3 hours at 37° C. This treatment produces capped poly(A)-tailed RNA having a cap I structure on the 5'-end of the RNA. The RNA was purified by phenol-chloroform extraction, ammonium acetate precipitation, 70% ethanol wash, and resuspended in RNase-free water to a final concentration of 0.2-0.5 µg/µl.

Method 11. Assays of In Vivo Translation of Modified-Nucleotide-Capped RNA in Cells HeLa cells (ATCC, Manassas, Va., USA), a cervical carcinoma cell line, and BDCM cells (ATCC, Manassas, Va., USA), a lymphoblast cell line with characteristics of dendritic cells, were grown under standard conditions in complete growth medium containing DMEM with 4.5 g/L of glucose, 584 mg/L of L-glutamine, and 110 mg/L of sodium pyruvate (Mediatech Inc., Herndon, Va., USA), 10% fetal bovine serum, 100 U/ml penicillin and 100 µg/ml streptomycin. Cells were dispensed into 12-well plates and grown for 24 hours before transfection. mRNA transfections were performed by lipofection. Transfection reaction mixes were prepared in reduced serum media OptiMem® I (Invitrogen Corp, Carlsbad, Calif., USA). The transfection mixes for HeLa cells contained 0.25 µg of each in vitro-transcribed *Renilla* luciferase mRNA, 0.5 µl mRNA Boost Reagent and 1 µl TransIT®-mRNA Reagent (Minis Bio Corp, Madison, Wis., USA) in serum-containing media and was incubated with the cells for approximately 18 hours. The transfection mixes for BDCM cells contained 0.5 µg of each in vitro-transcribed *Renilla* luciferase mRNA, 2.5 µl mRNA Boost Reagent and 0.5 µl TransIT®-mRNA Reagent (Minis Bio Corp, Madison, Wis., USA) in serum-containing media and was incubated with the cells for 8 hours. Cells were harvested by scraping and were lysed in Passive Lysis Buffer (Promega, Fitchburg, Wis., USA). Aliquots of lysed cell extracts were assayed for luminescence with the Luciferase Assay System (Promega, Fitchburg, Wis., USA) as per manufacturer's instructions on a Luminoskan Ascent Luminometer (Thermo Electron Corp., Waltham, Mass., USA). Relative light units (RLU) per transfection were normalized by the amount of protein in each sample. Total protein content was assayed for each extract with Coomassie Plus Bradford assay reagent (Pierce, Rockford, Ill., USA) as per manufacturer's instructions.

Method 12. Assays of In Vitro Translation of Modified-Nucleotide-Capped RNA in Cell-Free Extracts For in vitro translation assays in rabbit reticulocyte lysates, 0.5 µg of each *Renilla* luciferase mRNA was denatured at 65° C. for 5 minutes and subsequently translated with the Flexi® Rabbit Reticulocyte Lysate System (Promega, Fitchburg, Wis., USA) as per manufacturer's instructions for 90 minutes at 30° C. For in vitro translation assays in wheat germ extracts (Promega, Fitchburg, Wis., USA), the potassium concentration was optimized to 50 mM, and 0.5 µg of each *Renilla* luciferase mRNA was denatured at 65° C. for 5 minutes and subsequently translated in the wheat germ extract for 90 minutes at 25° C. as per manufacturer's instructions. Aliquots of translation extracts were assayed for luminescence with the Luciferase Assay System (Promega, Fitchburg, Wis., USA) as per manufacturer's instructions on a Luminoskan Ascent Luminometer (Thermo Electron Corp., Waltham, Mass., USA).

Results

Experiment 1. Control Reactions Using GTP as the Capping Nucleotide±S-Adenosyl-Methionine for Capping Enzyme Reactions, and Subsequent 2'-O-Methylation and/or Polyadenylation of Unmodified G-Capped RNA or Unmodified $N^7$-Methyl-G-Capped RNA.

1A.

When GTP was used as the nucleoside-5'-triphosphate in a capping enzyme reaction mixture set up as described in Method 1, and the capping enzyme reaction was carried out as described in Method 3 and analyzed as described in Method 4, the 51-base primary RNA transcript was quantitatively converted by the capping enzyme system into a 52-base capped RNA, as determined by polyacrylamide gel electrophoretic analysis of the reaction products using 51-base and 52-base size marker electrophoresis standards. This was a control reaction and demonstrated that the capping enzyme system efficiently catalyzed capping of the primary RNA transcript into capped RNA having a cap 0 structure, wherein the cap nucleotide lacked a methyl group on the $N^7$ position of the guanine base.

1B.

When GTP was used as the nucleoside-5'-triphosphate in a capping enzyme reaction mixture that additionally contained ($^{14}$C-methyl)-S-adenosyl-L-methionine, set up as described in Method 2, and the capping enzyme reaction was carried out as described in Method 3 and analyzed as described in Method 4, the 51-base primary RNA transcript was quantitatively converted by the capping enzyme system into a 52-base capped RNA, as determined by polyacrylamide gel electrophoretic analysis of the reaction products using 51-base and 52-base size marker electrophoresis standards, and the 52-base capped RNA contained the radioactive methyl group based on autoradiography of the dried gel as described in Method 5. Thus, this control reaction demonstrated that the capping enzyme system catalyzed capping of the primary RNA transcript into capped RNA having a cap 0 structure, wherein the cap nucleotide was additionally methylated at the $N^7$ position of the guanine base by the guanine 7-methyltransferase activity of the capping enzyme. This reaction served as a control for estimating relative methylation of the $N^7$ position of the cap nucleotide of modified-nucleotide-capped RNAs.

1C.

When the unlabeled unmodified $m^7$G-capped RNA control was incubated with mRNA (nucleoside-2'-O—) methyltransferase as described in Method 7, and the product was analyzed by PAGE and autoradiography, as described in Method 4 and Method 5, a 52-base band that contained radioactivity was observed. This control reaction demonstrated that mRNA (nucleoside-2'-O—) methyltransferase catalyzed methylation of the 2'-hydroxyl of the penultimate nucleotide at the 5-end of unmodified $m^7$G-capped RNA. This reaction served as a control for estimating relative methylation of the 5'-penultimate nucleotide in modified-nucleotide-capped RNA. In separate reactions, it was also determined that, if the RNA was capped by capping enzyme using GTP in the absence of S-adenosyl-L-methionine, G-capped RNA was still a substrate for mRNA (nucleoside-2'-O—) methyltransferase-catalyzed methylation of the 2'-hydroxyl of the 5'-penultimate nucleotide, based on incorporation of the radioactive methyl group.

1D.

When the unmodified $m^7$G-capped RNA was treated with tobacco acid pyrophosphatase (TAP), as described in Method 8, a 51-base band was observed on PAGE analysis, as described in Method 4, demonstrating removal of the $m^7$G cap nucleotide.

1E.

When the unmodified $m^7$G-capped RNA was incubated with poly(A) polymerase, as described in Method 9, a poly (A) tail was added to the RNA, the length of which varied with reaction time, substrate concentration and enzyme concentration.

Experiment 2. Use of Nucleoside-5'-Triphosphates with Base Modifications as Substrates for Capping Enzyme, and Uses of Modified-Nucleotide-Capped RNA Obtained Therefrom.

2A.

ATP, $N^7$-methyl-GTP ($m^7$GTP), 2',3'-ddGTP, 7-deaza-GTP, $N^1$-methyl-GTP, 3'-amino-2',3'-ddGTP, 3'-azido-2',3'-ddGTP, and $O^6$-methyl-GTP were each used as the nucleoside-5'-triphosphate in a capping enzyme reaction mixture set up as described in Method 1, and the capping enzyme reaction was carried out as described in Method 3 and analyzed as described in Method 4. ATP, $N^7$-methyl-GTP, 2',3'-ddGTP, and 7-deaza-GTP were not substrates for the capping enzyme system, since the 51-base primary RNA transcript was not converted by the capping enzyme system into a 52-base capped RNA. However, $N^1$-methyl-GTP, 3'-amino-2',3'-ddGTP, 3'-azido-2',3'-ddGTP, and $O^6$-methyl-GTP were substrates for the capping enzyme system. The capping enzyme system quantitatively converted the 51-base primary RNA transcript to a 52-base capped RNA in a 30-minute reaction in the presence of $N^1$-methyl-GTP based on PAGE analysis. Under the same conditions, approximately 70% of the 51-base primary RNA transcript was converted by the capping enzyme system into a 52-base capped RNA in the presence of $O^6$-methyl-GTP. Thus, capping enzyme can use nucleoside triphosphates with some, but not all, guanine base modifications as substrates for synthesis of capped RNA having a cap 0 structure, wherein the cap nucleotide lacks a methyl group on the $N^7$ position of the guanine base.

2B.

When $O^6$-methyl-GTP was used as the nucleoside-5'-triphosphate in a capping enzyme reaction mixture that additionally contained ($^{14}$C-methyl)-S-adenosyl-L-methionine, set up as described in Method 2, and the capping enzyme reaction was carried out as described in Method 3 and analyzed as described in Method 4 and Method 5, the 51-base primary RNA transcript was quantitatively converted by the capping enzyme system into a radioactive 52-base capped RNA. Thus, the capping enzyme system catalyzed formation of $N^7$-methylated capped RNA having a cap 0 structure when $O^6$-methyl-GTP was used as the modified cap nucleotide. However, under the same reaction conditions with the $N^1$-methyl-GTP, a 52-base band was formed, but it did not contain any radioactivity, showing that $N^1$-methyl-G-capped RNA was not methylated. Therefore, the $N^1$-methyl-G modified cap nucleotide was not a substrate for subsequent methylation at the $N^7$ position by the capping enzyme system.

2C.

When either unlabeled $N^1$-methyl-G-capped RNA or $O^6$-methyl-G-capped RNA was incubated with mRNA (nucleoside-2'-O—) methyltransferase as described in Method 7, and the product was analyzed by PAGE and autoradiography, as described in Method 4 and Method 5, a 52-base radioactive band was observed. Thus, mRNA (nucleoside-2'-O—) methyltransferase catalyzed methylation of the 2'-hydroxyl of the 5'-penultimate nucleotide of both $N^1$-methyl-G-capped RNA and $O^6$-methyl-G-capped RNA (although, as described in 2B above, the $O^6$-methyl-G-capped RNA had an $N^7$-methyl group on the modified cap nucleotide, whereas the $N^1$-methyl-G-capped RNA did not). Thus, RNA capped with either $N^1$-methyl-G or $O^6$-methyl-G modified cap nucleotides were substrates for methylation of the 2'-hydroxyl of the 5'-penultimate nucleotide by mRNA (nucleoside-2'-O—) methyltransferase. However, the amount of radioactivity incorporated into the 52-base band using the $O^6$-methyl-G-capped RNA as the substrate indicated that the reaction with this substrate was not highly efficient.

2D.

When the $N^1$-methyl-G-capped RNA or $O^6$-methyl-G-capped RNA was treated with tobacco acid pyrophosphatase (TAP), as described in Method 8, a 51-base band was observed on PAGE analysis, as described in Method 4, demonstrating removal of the $N^1$-methyl-G or $O^6$-methyl-G cap nucleotide.

Experiment 3. Use of Nucleoside-5'-Triphosphates Having 2' and/or 3' Modifications of the Sugar Moiety as Substrates for Capping Enzyme, and Uses of Modified-Nucleotide-Capped RNA Obtained Therefrom.

3A.

The following nucleoside-5'-triphosphates having 2' and/or 3' modifications of the sugar moiety were each used as the modified cap nucleotide in a capping enzyme reaction mixture set up as described in Method 1, and the capping enzyme reaction was carried out as described in Method 3 and analyzed as described in Method 4: 2',3'-dideoxy-GTP (i.e., 2',3'-ddGTP); 2'-dGTP; 2'-OMe-GTP; 3'-OMe-GTP; 2'-F-dGTP; 2'-amino-2'-dGTP (i.e., 2'-amino-dGTP); and 2'-azido-2'-dGTP (i.e., 2'-azido-dGTP). The 2',3'-ddGTP was not a substrate for the capping enzyme system, since the 51-base primary RNA transcript was not converted by the capping enzyme system into a 52-base capped RNA. However, all of the remaining nucleoside-5'-triphosphates having 2' and/or 3' modifications of the sugar moiety were substrates for the capping enzyme system. The capping enzyme system quantitatively converted the 51-base primary RNA transcript to a 52-base capped RNA in a 30-minute reaction in the presence of 2'-dGTP, 3'-OMe-GTP, and 2'-amino-dGTP based on PAGE analysis. Under the same conditions, approximately 50-75% of the 51-base primary RNA transcript was converted by the capping enzyme system into a 52-base capped RNA in the presence of 2'-OMe-GTP, 2'-F-dGTP, and 2'-azido-dGTP; when the reaction time using these modified cap nucleotides was extended from 30 minutes to 2 hours or 6 hours, the percentage of the RNA capped increased still further, being approximately 80-100% in some experiments. Thus, capping enzyme used all of these modified nucleoside triphosphates, except the 2',3'-ddGTP as substrates for synthesis of capped RNA having a cap 0 structure, wherein the cap nucleotide lacked a methyl group on the $N^7$ position of the guanine base.

3B.

When 3'-OMe-GTP, 2'-OMe-GTP, 2'-dGTP, 2'-F-dGTP, 2'-amino-dGTP, or 2'-azido-dGTP was used as the nucleoside-5'-triphosphate in a capping enzyme reaction mixture that additionally contained ($^{14}$C-methyl)-S-adenosyl-L-methionine, set up as described in Method 2, and the capping enzyme reaction was carried out as described in Method 3 and analyzed as described in Method 4 and Method 5, 95-100% of the 51-base primary RNA transcript was converted by the capping enzyme system into a radioactive 52-base capped RNA in a 2-hour reaction. Thus, the capping enzyme system catalyzed formation of $N^7$-methylated capped RNA having a cap 0 structure when these modified cap nucleotides were used.

3C.

When unlabeled modified-nucleotide-capped RNA was prepared using 3'-OMe-GTP, 2'-OMe-GTP, 2'-dGTP, 2'-F-dGTP, 2'-amino-dGTP, or 2'-azido-dGTP as the cap nucleotide and then was incubated with mRNA (nucleoside-2'-O—) methyltransferase as described in Method 7, and the product was analyzed by PAGE and autoradiography, as described in Method 4 and Method 5, a 52-base radioactive band was observed for all of the modified-nucleotide-capped RNAs tested. Thus, modified-nucleotide-capped RNA obtained using 3'-OMe-GTP, 2'-OMe-GTP, 2'-dGTP, 2'-F-dGTP, 2'-amino-dGTP, or 2'-azido-dGTP as the modified cap nucleotides were substrates for methylation of the 2'-hydroxyl of the 5'-penultimate nucleotide by mRNA (nucleoside-2'-O—) methyltransferase. These modified-nucleotide-capped RNAs also had a methyl group on the $N^7$-position of the modified cap nucleotide from the capping enzyme reaction of Method 6. However, the mRNA (nucleoside-2'-O—) methyltransferase can also catalyze methylation of the 2'-hydroxyl of the 5'-penultimate nucleotide if the $N^7$-position of the modified cap nucleotide is not methylated. For example, when modified-nucleotide-capped RNA was prepared as described in Method 1 using 2'-F-dGTP (except that the reaction was carried out for two hours), then incubated with mRNA (nucleoside-2'-O—) methyltransferase as described in Method 7 and the product was analyzed by PAGE and autoradiography as described in Methods 4 and 5, a 52-base radioactive band was observed.

3D.

Modified-nucleotide-capped RNA was prepared as described in Method 6 using 3'-OMe-GTP, 2'-OMe-GTP, 2'-dGTP, or 2'-amino-dGTP as the modified cap nucleotide. Modified-nucleotide-capped RNA was prepared as described in Method 6, except in the absence of S-adenosyl-L-methionine, using 2'-F-dGTP as the modified cap nucleotide. When each of these modified-nucleotide-capped RNAs was treated with tobacco acid pyrophosphatase (TAP), as described in Method 8, a 51-base band was observed on PAGE analysis, as described in Method 4, demonstrating removal of the respective modified cap nucleotide. The PAGE gel obtained for the TAP decapping reaction of the modified-nucleotide-capped RNA prepared as described in Method 6 using 2'-azido-dGTP was not interpretable, so no conclusion could be made about whether this modified cap nucleotide could be removed by TAP.

Experiment 4. In Vivo Translation of Modified-Nucleotide-Capped Poly(A)-Tailed RNA Having a Cap O or Cap I Structure in HeLa and BDCM Cells.

Unmodified- or modified-nucleotide-capped poly(A)-tailed *Renilla* luciferase RNAs having either a cap 0 or a cap I structure were prepared as described in Method 10 using either GTP or one of the following modified nucleoside-5'-triphosphates: $N^1$-methyl-GTP, $O^6$-methyl-GTP, 2'-dGTP; 3'-dGTP; 2'-OMe-GTP; 3'-OMe-GTP; 2'-F-2'-dGTP (i.e., 2'-F-dGTP); 2'-azido-2'-dGTP (i.e., 2'-azido-dGTP); and 2'-amino-2'-dGTP (i.e., 2'-amino-dGTP). Each of the modified-nucleotide-capped poly(A)-tailed *Renilla* luciferase RNAs was then evaluated for in vivo translation in HeLa and BDCM Cells as described in Method 11. For each cell line, the level of translation obtained using each modified-nucleotide-capped poly(A)-tailed *Renilla* luciferase RNA was compared to the level of translation obtained using the unmodified capped poly(A)-tailed *Renilla* luciferase RNA obtained using GTP as the capping nucleotide. Thus, for each cell line, the relative level of translation obtained with the unmodified capped poly(A)-tailed *Renilla* luciferase RNA was assigned a value of 100% and the level of translation obtained with each modified-nucleotide-capped poly(A)-tailed *Renilla* luciferase RNA was assigned a relative percent translation value compared to that obtained using the unmodified capped poly(A)-tailed *Renilla* luciferase RNA. The relative percent translation value enables comparisons of the effects of different cap nucleotides on translation efficiency. However, it should be noted that the amount of in vivo translation product from capped poly(A)-tailed *Renilla* luciferase RNA, as measured by the number of relative light units (RLUs) per microgram of total protein per sample, was higher for capped RNAs having a cap I structure than for capped RNAs having the same cap nucleotide but with a cap 0 structure. For example, the RLUs measured in HeLa cells were about 2.2 times higher using GTP-capped poly(A)-tailed *Renilla* luciferase RNA having a cap I structure than for GTP-capped poly(A)-tailed *Renilla* luciferase RNA having a cap 0 structure, even though each reading was defined as 100% translation efficiency for the purpose of comparing the effects of different cap nucleotides on RNA having caps of the same cap structure on translation efficiency. However, the differences in the RLUs for GTP-capped poly(A)-tailed *Renilla* luciferase RNA having a cap I compared to a cap 0 structure was less in BDCM cells. Thus, the RLUs measured in BDCM cells were only about 1.3 times higher using GTP-capped poly(A)-tailed *Renilla* luciferase RNA having a cap I structure than using GTP-capped poly(A)-tailed *Renilla* luciferase RNA having a cap 0 structure. The presence of a cap nucleotide was important for in vivo translation. For example, no translation was detected using this assay when HeLa cells were transfected with uncapped poly(A)-tailed *Renilla* luciferase RNA.

4A. In Vivo Translation in HeLa Cells.

By comparison with the GTP-capped poly(A)-tailed *Renilla* luciferase RNA having a cap 0 structure (100% translation efficiency), the average relative translation efficiency in HeLa cells following transfection by a modified-nucleotide-capped poly(A)-tailed *Renilla* luciferase RNA having a cap 0 was as follows if the RNA was capped using: $N^1$-methyl-GTP, 3%; $O^6$-methyl-GTP, 114%; 2'-dGTP, 64%; 3'-dGTP, 45%; 2'-OMe-GTP, 86%; 3'-OMe-GTP, 47%; 2'-F-2'-dGTP (i.e., 2'-F-dGTP), 46%; 2'-azido-2'-dGTP (i.e., 2'-azido-dGTP), 66%; and 2'-amino-2'-dGTP (i.e., 2'-amino-dGTP), 172%.

The average relative translation efficiency of modified-nucleotide-capped poly(A)-tailed *Renilla* luciferase RNA having a cap I structure in HeLa cells was as follows if the RNA was capped using: $N^1$-methyl-GTP, <1%; $O^6$-methyl-GTP, 134%; 2'-dGTP, 68%; 3'-dGTP, 48%; 2'-OMe-GTP, 104%; 3'-OMe-GTP, 31%; 2'-F-2'-dGTP (i.e., 2'-F-dGTP), 54%; 2'-azido-2'-dGTP (i.e., 2'-azido-dGTP), 52%; and 2'-amino-2'-dGTP (i.e., 2'-amino-dGTP), 254%.

In subsequent experiments in which a different luciferase transcript was prepared from a firefly luciferase gene, and the transcript was subsequently capped and polyadenylated using the same methods as for the above modified-nucleotide-capped poly(A)-tailed *Renilla* luciferase RNA, the average relative translation efficiency of this modified-nucleotide-capped poly(A)-tailed luciferase RNA having a cap I structure in HeLa cells was as follows if the RNA was capped using: $N^1$-methyl-GTP, <1%; $O^6$-methyl-GTP, 146%; 2'-dGTP, 61%; 3'-dGTP, 61%; 2'-OMe-GTP, 90%; 3'-OMe-GTP, 65%; 2'-F-2'-dGTP (i.e., 2'-F-dGTP), 105%; 2'-azido-2'-dGTP (i.e., 2'-azido-dGTP), 64%; and 2'-amino-2'-dGTP (i.e., 2'-amino-dGTP), 43%.

In another set of experiments to determine the effect of the poly(A) tail length on in vivo expression, the present inventors found that the amount of in vivo translation in HeLa cells of one cap 0-type polyadenylated $m^7$G-capped *Renilla* luciferase RNA or $m_2^{7,3'-O}$G-capped *Renilla* luciferase RNA increased as the poly(A) tail length increased up to about 400 nucleotides. However, with the firefly luciferase RNA, the amount of in vivo translation in HeLa cells of the cap 0-type polyadenylated RNA did not increase if the length of the poly(A) tail was greater than about 100 to about 200 nucleotides.

4B. In Vivo Translation in BDCM Cells.

By comparison with the GTP-capped poly(A)-tailed *Renilla* luciferase RNA having a cap 0 structure (100% translation efficiency), the relative translation efficiency of modified-nucleotide-capped poly(A)-tailed *Renilla* luciferase RNA having a cap 0 structure in BDCM cells was as follows if the RNA was capped using: $O^6$-methyl-GTP, 115%; and 2'-amino-2'-dGTP (i.e., 2'-amino-dGTP), 150%. When modified-nucleotide-capped *Renilla* luciferase RNA having a cap 0 structure was prepared co-transcriptionally using an $m_2^{7,3'-O}$GpppG cap analog (ARCA) in a T7 RNA polymerase in vitro transcription reaction, and then tailed using poly(A) polymerase as described in Method 10, the relative translation efficiency of the ARCA-capped RNA in BDCM cells was 130% compared to unmodified capped poly(A)-tailed *Renilla* luciferase RNA obtained using vaccinia capping enzyme and GTP as the capping nucleotide.

The relative translation efficiency of modified-nucleotide-capped poly(A)-tailed *Renilla* luciferase RNA having a cap I structure in BDCM cells was as follows if the RNA was capped using: $O^6$-methyl-GTP, 117%; and 2'-amino-2'-dGTP (i.e., 2'-amino-dGTP), 177%. When modified-nucleotide-capped *Renilla* luciferase RNA having a cap I structure was prepared co-transcriptionally using an $m_2^{7,3'-O}$GpppG cap analog (ARCA) in a T7 RNA polymerase in vitro transcription reaction, and then tailed using poly(A) polymerase as described in Method 10, the relative translation efficiency of the ARCA-capped RNA in BDCM cells was 102% compared to unmodified capped poly(A)-tailed *Renilla* luciferase RNA obtained using vaccinia capping enzyme and GTP as the capping nucleotide.

Experiment 5. In Vitro Translation of Modified-Nucleotide-Capped Poly(A)-Tailed RNA Having a Cap 0 or Cap I Structure in Cell-Free Extracts.

Unmodified- or modified-nucleotide-capped poly(A)-tailed *Renilla* luciferase RNAs having either a cap 0 or a cap I structure were prepared as described in Method 10 using either GTP or one of the following modified nucleoside-5'-triphosphates: $N^1$-methyl-GTP, $O^6$-methyl-GTP, 2'-dGTP; 3'-dGTP; 2'-OMe-GTP; 3'-OMe-GTP; 2'-F-2'-dGTP (i.e., 2'-F-dGTP); 2'-azido-2'-dGTP (i.e., 2'-azido-dGTP); and 2'-amino-2'-dGTP (i.e., 2'-amino-dGTP). Each of the modified-nucleotide-capped poly(A)-tailed *Renilla* luciferase RNAs was then evaluated for in vitro translation in a rabbit reticulocyte lysate and a wheat germ lysate as described in Method 12. For each lysate, the level of translation obtained using each modified-nucleotide-capped poly(A)-tailed *Renilla* luciferase RNA was compared to the level of translation obtained using the unmodified capped poly(A)-tailed *Renilla* luciferase RNA obtained using GTP as the capping nucleotide. The level of translation obtained with the unmodified capped poly(A)-tailed *Renilla* luciferase RNA in each lysate was assigned a value of 100% and the level of translation obtained with each modified-nucleotide-capped poly (A)-tailed *Renilla* luciferase RNA was assigned a relative percent translation value for that lysate compared to that obtained using the unmodified capped poly(A)-tailed *Renilla* luciferase RNA. The presence of a cap nucleotide was helpful but not essential for in vitro translation, since the level of translation of uncapped poly(A)-tailed *Renilla* luciferase RNA in rabbit reticulocyte lysate and wheat germ lysate was about 50% and 32%, respectively, of that obtained using either a cap O— or a cap I-type capped poly(A)-tailed *Renilla* luciferase RNA made using vaccinia capping enzyme and GTP as the capping nucleotide.

5a. In Vitro Translation in Rabbit Reticulocyte Lysate.

By comparison with the GTP-capped poly(A)-tailed *Renilla* luciferase RNA having a cap 0 structure (100% translation efficiency), the average relative translation efficiency in rabbit reticulocyte lysate of modified-nucleotide-capped poly (A)-tailed *Renilla* luciferase RNA having a cap 0 structure was as follows if the RNA was capped using: $N^1$-methyl-GTP, 56%; $O^6$-methyl-GTP, 167%; 2'-dGTP, 118%; 3'-dGTP, 80%; 2'-OMe-GTP, 132%; 3'-OMe-GTP, 82%; 2'-F-2'-dGTP (i.e., 2'-F-dGTP), 55%; 2'-azido-2'-dGTP (i.e., 2'-azido-dGTP), 99%; and 2'-amino-2'-dGTP (i.e., 2'-amino-dGTP), 148%.

The average relative translation efficiency of modified-nucleotide-capped poly(A)-tailed *Renilla* luciferase RNA having a cap I structure in rabbit reticulocyte lysate was as follows if the RNA was capped using: $N^1$-methyl-GTP, 50%; $O^6$-methyl-GTP, 122%; 2'-dGTP, 84%; 3'-dGTP, 64%; 2'-OMe-GTP, 97%; 3'-OMe-GTP, 84%; 2'-F-2'-dGTP (i.e., 2'-F-dGTP), 107%; 2'-azido-2'-dGTP (i.e., 2'-azido-dGTP), 79%; and 2'-amino-2'-dGTP (i.e., 2'-amino-dGTP), 144%.

In subsequent experiments in which a different luciferase transcript was prepared from a firefly luciferase gene, and the transcript was subsequently capped and polyadenylated using the same methods as for the above modified-nucleotide-capped poly(A)-tailed *Renilla* luciferase RNA, the average relative translation efficiency of this modified-nucleotide-capped poly(A)-tailed luciferase RNA having a cap I structure in rabbit reticulocyte lysate was as follows if the RNA was capped using: $N^1$-methyl-GTP, 16%; $O^6$-methyl-GTP, 97%; 2'-dGTP, 128%; 3'-dGTP, 98%; 2'-OMe-GTP, 170%; 3'-OMe-GTP, 137%; 2'-F-2'-dGTP (i.e., 2'-F-dGTP), 133%; 2'-azido-2'-dGTP (i.e., 2'-azido-dGTP), 107%; and 2'-amino-2'-dGTP (i.e., 2'-amino-dGTP), 100%.

5B. In Vitro Translation in Wheat Germ Lysate.

By comparison with the GTP-capped poly(A)-tailed *Renilla* luciferase RNA having a cap 0 structure (100% translation efficiency), the relative translation efficiency in wheat germ lysate of modified-nucleotide-capped poly(A)-tailed *Renilla* luciferase RNA having a cap 0 structure was as follows if the RNA was capped using: $N^1$-methyl-GTP, 31%; $O^6$-methyl-GTP, 80%; 2'-dGTP, 54%; 2'-OMe-GTP, 36%; 3'-OMe-GTP, 39%; 2'-F-2'-dGTP (i.e., 2'-F-dGTP), 53%; 2'-azido-2'-dGTP (i.e., 2'-azido-dGTP), 41%; and 2'-amino-2'-dGTP (i.e., 2'-amino-dGTP), 90%.

The relative translation efficiency of modified-nucleotide-capped poly(A)-tailed *Renilla* luciferase RNA having a cap I structure in wheat germ lysate was as follows if the RNA was capped using: $N^1$-methyl-GTP, 31%; $O^6$-methyl-GTP, 59%; 2'-dGTP, 54%; 3'-dGTP, 31%; 2'-OMe-GTP, 47%; 3'-OMe-GTP, 43%; 2'-F-2'-dGTP (i.e., 2'-F-dGTP), 61%; 2'-azido-2'-dGTP (i.e., 2'-azido-dGTP), 42%; and 2'-amino-2'-dGTP (i.e., 2'-amino-dGTP), 110%.

We claim:

1. A composition for obtaining a modified nucleotide-capped RNA comprising:
   i) a capping enzyme system comprising an RNA guanyltransferase that exhibits motif I consisting of the amino acid sequence KxDGxx; and
   ii) a modified cap nucleotide, wherein the modified cap nucleotide:
      A) is 3'-deoxyguanosine-5'-triphosphate or comprises a modified 2'- or 3'-deoxyguanosine-5'-triphosphate, wherein the 2'- or 3'-deoxy position of the sugar moiety is substituted by a group other than a hydroxyl group or a hydrogen, in particular wherein the 2'- or 3'-deoxy position of the sugar moiety is substituted with an amino, an azido, a fluorine, a methoxy, a thiol, or a mercapto group, or wherein the $O^6$-oxygen of the guanine base is replaced with a thiol or mercapto group;
      B) comprises a modified guanosine-5'-triphosphate, wherein the 2'- or 3'-hydroxyl group of the ribose is substituted with an alkyl group, or wherein the $O^6$-oxygen of the guanine is substituted with an alkyl group or is replaced with a thiol or mercapto group; or
      C) is selected from: N1-methyl-GTP; $O^6$-methyl-GTP; 6-thio-GTP; 2'-O-methyl-GTP; 3'-O-methyl-GTP; 2'-amino-2'-dGTP; 3'-amino-3'-dGTP; 2'-azido-2'-dGTP; 3'-azido-3'-dGTP; 2'-F-2'-dGTP; 3'-F-3'-dGTP; 3'-dGTP; 2'-amino-2',3'-ddGTP; 3'-amino-2',3'-ddGTP; 2'-azido-2',3'-ddGTP; and 3'-azido-2',3'-ddGTP.

2. The composition of claim 1, wherein the RNA guanyltransferase comprises a motif I that exhibits the amino acid sequence KTDG(I/V)x, wherein the sixth amino acid of said motif I is P, G, F, S or L.

3. The composition of claim 1, further comprising uncapped RNA that exhibits a 5' diphosphate.

4. The composition of claim 1, further comprising polypeptide having RNA triphosphatase activity.

5. The composition of claim 4, further comprising uncapped RNA that exhibits a 5' triphosphate.

6. The composition of claim 5, wherein the uncapped RNA is:
   (i) a primary RNA transcript from a human, animal, plant, or fungal organism, organ, tissue, or cell, or from extracellular fluid from a patient or organism with a condition;
   (ii) primary RNA from an in vitro transcription reaction;
   (iii) obtained following fractionation of RNA from a biological source by subtractive hybridization and digestion, and RNA amplification that yields sense RNA;
   (iv) primary RNA from a prokaryotic source;
   (v) derived from a condition comprising a tumor or cancer cell; or
   (vi) derived from a pathogen, or from a eukaryotic cell that is infected by a bacterial, viral or fungal pathogen.

7. The composition of claim 1, further comprising S-adenosyl-methionine or S-adenosyl-ethionine.

8. The composition of claim 7, further comprising a polypeptide having guanine-7-methyltransferase activity.

9. The composition of claim 8, further comprising modified-nucleotide capped RNA, wherein the 5' cap nucleotide comprises a modified guanine nucleoside-5'-triphosphate of claim 1 (b).

10. The composition of claim 9, further comprising an enzyme having mRNA (nucleoside-2'-O—) methyltransferase activity.

11. The composition of claim 10, wherein the enzyme having mRNA (nucleoside-2'-O—) methyltransferase activity is:
    (i) encoded by a poxvirus DNA;
    (ii) encoded a vaccinia virus DNA;
    (iii) is purified from virions;
    (iv) is purified from a recombinant source;
    (v) is purified from *E. coli* cells that express a poxvirus gene that is cloned in a plasmid or other vector;
    (vi) is purified from *E. coli* cells that express the vaccinia gene that is cloned in a plasmid or other vector;
    (vii) is encoded by a yeast or fungal gene; or
    (viii) is encoded by a nematode, mammalian or other metazoan gene, whether from a wild-type or recombinant source.

12. The composition of claim 9, wherein the modified-nucleotide capped RNA exhibits a cap with a cap1 structure, wherein the 5' penultimate nucleotide has a 2'-O-methyl group.

13. The composition of claim 1 further comprising poly(A) polymerase.

14. The composition of claim 13, wherein said poly(A) polymerase is (i) *Escherichia coli* poly(A) polymerase; (ii) yeast poly(A) polymerase; or (iii) is recombinant poly(A) polymerase encoded by the *E. coli* pcnB gene.

15. The composition of claim 9, wherein the modified-nucleotide capped RNA further exhibits a poly(A) tail.

16. The composition of claim 12, wherein the modified-nucleotide capped RNA that exhibits a cap with a cap1 structure further exhibits a poly(A) tail.

17. The composition of claim 1, further comprising a component that improves the efficiency of capping uncapped RNA that forms a duplex involving at least the 5'-terminal nucleotide, wherein said component consists of at least one of the following: (i) dimethylglycine (betaine); (ii) a single-stranded binding protein; (iii) an RNA helicase; (iv) an RNA polymerase; or (v) a DNA polymerase.

18. The composition of claim 9, wherein the modified-nucleotide capped RNA further comprises a biotin moiety.

19. The composition of claim 12, wherein the modified-nucleotide capped RNA that exhibits a cap with a cap1 structure further comprises a biotin moiety.

20. The composition of claim 15, wherein the modified-nucleotide capped RNA that exhibits a poly(A) tail further comprises a biotin moiety.

21. The composition of claim 1, further comprising an uncapped RNA comprising a primary RNA transcript or an RNA that has a 5'-diphosphate.

* * * * *

SEQUENCE LISTING

```
<160> NUMBER OF SEQ ID NOS: 9

<210> SEQ ID NO 1
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid

<400> SEQUENCE: 1

Lys Xaa Asp Gly Xaa Xaa
1               5

<210> SEQ ID NO 2
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (5)..(5)
<223> OTHER INFORMATION: Xaa is Ile or Val
<220> FEATURE:
<221> NAME/KEY: MISC_FEATURE
<222> LOCATION: (6)..(6)
<223> OTHER INFORMATION: Xaa is Pro or Gly

<400> SEQUENCE: 2

Lys Thr Asp Gly Xaa Xaa
1               5

<210> SEQ ID NO 3
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (5)..(5)
<223> OTHER INFORMATION: Xaa is Ile or Val
<220> FEATURE:
<221> NAME/KEY: misc_feature
<222> LOCATION: (6)..(6)
<223> OTHER INFORMATION: Xaa can be any naturally occurring amino acid

<400> SEQUENCE: 3

Lys Thr Asp Gly Xaa Xaa
1               5

<210> SEQ ID NO 4
<211> LENGTH: 8
<212> TYPE: PRT
<213> ORGANISM: Artificial Sequence
<220> FEATURE:
<223> OTHER INFORMATION: Synthetic

<400> SEQUENCE: 4

Val Val Val Phe Gly Glu Ala Val
1               5
```

```
<210> SEQ ID NO 5
<211> LENGTH: 8
<212> TYPE: PRT
<213> ORGANISM: Artificial Sequence
<220> FEATURE:
<223> OTHER INFORMATION: Synthetic

<400> SEQUENCE: 5

Tyr Arg Leu Trp Cys Glu Ala Val
1               5

<210> SEQ ID NO 6
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: Xaa is Leu or Ile
<220> FEATURE:
<221> NAME/KEY: MISC_FEATURE
<222> LOCATION: (8)..(8)
<223> OTHER INFORMATION: Xaa is Ile or Val

<400> SEQUENCE: 6

Val Thr Xaa Tyr Gly Glu Ala Xaa
1               5

<210> SEQ ID NO 7
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is Val or Ile

<400> SEQUENCE: 7

Xaa Tyr Leu Tyr Ala Glu Met Arg
1               5

<210> SEQ ID NO 8
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is Val or Ile
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: MISC_FEATURE
<222> LOCATION: (4)..(4)
<223> OTHER INFORMATION: Xaa is Tyr or Phe
<220> FEATURE:
<221> NAME/KEY: MISC_FEATURE
<222> LOCATION: (8)..(8)
<223> OTHER INFORMATION: Xaa is Ile or Val

<400> SEQUENCE: 8

Xaa Xaa Leu Xaa Gly Glu Ala Xaa
1               5
```

```
<210> SEQ ID NO 9
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: Xaa is Asp or Glu
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 9

Val Leu Xaa Xaa Gly Xaa Gly Xaa Gly
1               5
```